US007507753B2

(12) United States Patent
Cho et al.

(10) Patent No.: US 7,507,753 B2
(45) Date of Patent: Mar. 24, 2009

(54) BIARYL COMPOUND AND USE THEREOF

(75) Inventors: Nobuo Cho, Tsukuba (JP); Kazuyoshi Aso, Takatsuki (JP); Satoshi Endo, Takatsuki (JP); Naoyuki Kanzaki, Ibaraki (JP); Satoshi Sasaki, Ushiku (JP)

(73) Assignee: Takeda Chemical Industries Ltd., Osaka (JP)

( * ) Notice: Subject to any disclaimer, the term of this patent is extended or adjusted under 35 U.S.C. 154(b) by 579 days.

(21) Appl. No.: 10/499,903

(22) PCT Filed: Dec. 26, 2002

(86) PCT No.: PCT/JP02/13655

§ 371 (c)(1),
(2), (4) Date: Jun. 23, 2004

(87) PCT Pub. No.: WO03/057671

PCT Pub. Date: Jul. 17, 2003

(65) Prior Publication Data
US 2005/0096359 A1 May 5, 2005

(30) Foreign Application Priority Data
Dec. 28, 2001 (JP) .............................. 2001-401303

(51) Int. Cl.
A61K 31/445 (2006.01)
C07D 211/58 (2006.01)
(52) U.S. Cl. .................. 514/329; 514/255; 514/318; 514/319; 514/326; 544/360; 546/194; 546/205; 546/208; 546/224
(58) Field of Classification Search .............. 546/224, 546/194, 205, 208; 514/329, 255, 318, 319, 514/326; 544/360
See application file for complete search history.

(56) References Cited

U.S. PATENT DOCUMENTS

| 5,053,548 | A | 10/1991 | Tanaka et al. | |
|---|---|---|---|---|
| 5,236,937 | A | 8/1993 | Bradbury et al. | |
| 5,356,893 | A | 10/1994 | Bradshaw et al. | |
| 6,350,760 | B1 | 2/2002 | Bakshi et al. | |
| 6,472,398 | B1 | 10/2002 | Palucki et al. | |
| 6,673,829 | B2 * | 1/2004 | Dorwald et al. | 514/210.2 |
| 6,919,343 | B2 * | 7/2005 | Wood et al. | 514/256 |
| 7,067,535 | B2 * | 6/2006 | Takahashi et al. | 514/329 |
| 2001/0029259 | A1 | 10/2001 | Nargund et al. | |
| 2002/0019523 | A1 | 2/2002 | Palucki et al. | |
| 2002/0103213 | A1 | 8/2002 | Hickey et al. | |
| 2002/0137664 | A1 | 9/2002 | Bakshi et al. | |
| 2003/0195212 | A1 | 10/2003 | Lundstedt et al. | |
| 2003/0207863 | A1 | 11/2003 | Fukumoto et al. | |

FOREIGN PATENT DOCUMENTS

EP 1295867 A1 3/2003

| WO | WO 96/10559 | | 4/1996 |
|---|---|---|---|
| WO | WO 01/25189 A1 | | 4/2001 |
| WO | WO 01/55109 A1 | | 8/2001 |
| WO | WO 02/55107 A2 | | 8/2001 |
| WO | WO02/24649 | * | 3/2002 |
| WO | WO 02/26710 | * | 4/2002 |

OTHER PUBLICATIONS

Boss et al. preparation of substituted . . . CA 136:279344 (2002).*
Tarui et al. "Preparation of biphenylcarboximide . . . " CA 136:85822 (2002).*
Bromidge et al. "preparation of biaryl . . . " CA 141:410692 (2004).*
Bundgaard "Design of prodrugs" p. 27-28 (1985).*
Burger "A guide to the chemical basis of drug design" p. 15 (1983).*
Cho et al. "Preparation of biaryl . . . " CA139:101034 (2003).*
D. Huszar, et al., "Targeted Disruption of the Melanocortin-4 Receptor Results in Obesity in Mice", Cell, (1997) pp. 131-141, vol. 88.
H. Wessells, et al., "Synthetic Melanotropic Peptide Initiates Erections in Men with Psychogenic Erectile Dysfunction: Double-Blind, Placebo Controlled Crossover Study", Journal of Urology, (1998) pp. 389-393, Vo. 160.
A. Catania, et al., "Alpha-Melanocyte-stimulating Hormone in Normal Human Physiology and Disease States", TEM, (2000) pp. 304-308, vol. 11, No. 8.
W. Chen, et al., "Exocrine Gland Dysfunction in MC5-R-Deficient Mice: Evidence for Coordinated Regulation of Exocrine Gland Function Melanocortin Peptides", Cell, (1997) pp. 789-798, vol. 91.
A. Vergoni, et al., "Differential Influence of a Selective Melanocortin MC4 Receptor Antagonist (HS014) on Melanocortin-Induced Behavioral Effects in Rats," European Journal of Pharmacology, (1998) pp. 95-101, vol. 362.

* cited by examiner

*Primary Examiner*—Celia Chang
(74) *Attorney, Agent, or Firm*—Hogan & Hartson LLP

(57) ABSTRACT

The present invention provides a compound having melanocortin receptor agonist activity or antagonist activity, which is a novel biaryl compound represented by the formula (I):

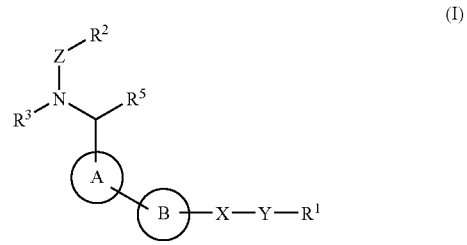

wherein ring A and ring B are optionally further substituted 6-membered aromatic rings; X is —$CONR^4$—, —$SO_2NR^4$—, —$CH_2NR^4$— ($R^4$ is a hydrogen atom, an optionally substituted hydrocarbon group, etc.), etc.; Y is a spacer having 1 to 12 atoms, etc.; Z is —$CONR^6$—, —CO— ($R^6$ is a hydrogen atom, an optionally substituted hydrocarbon group or an optionally substituted heterocyclic group), etc.; $R^1$ is an optionally substituted amino group, etc.; $R^2$ is an optionally substituted hydrocarbon group, etc.; $R^3$ is an optionally substituted hydrocarbon group, etc.; and $R^5$ is an optionally substituted hydrocarbon group, etc.; or a salt thereof.

6 Claims, No Drawings

BIARYL COMPOUND AND USE THEREOF

This application is the National Phase filing of International Patent Application No. PCT/JP02/13655, filed 26 Dec. 2002.

TECHNICAL FIELD

The present invention relates to a novel biaryl compound or a salt thereof acting on melanocortin receptor (MC-R), and the use thereof.

BACKGROUND ART

Melanocyte Stimulating Hormone (MSH, also called as melanotropin) produced by processing of proopiomelanocortin (POMC), a hypothalamic hormone, is known to be involved in skin pigmentation, inflammation, immunity, modulation of food intake and the like, and to affect memory and learning, regulation of body temperature, pain transmission, sexual behavior, affective behavior and the like. MSH has three types ($\alpha$, $\beta$ and $\gamma$) and they express a variety of physiological functions by mediation of melanocortin receptor (MC-R), which is a G protein-coupled receptor (GPCR). Five subtypes of melanocortin receptor (MC-1R, 2R, 3R, 4R and 5R) have been identified, and these are expressed in different tissues. MC-1R is mainly expressed in melanocytes, affecting skin or hair color of animal by leading to synthesis of eumelanin from phaeomelanin through control of tyrosinase. MC-2R is expressed in the adrenal gland and represents the adrenocorticotropic hormone (ACTH) receptor. MC-3R is expressed in the brain, gut, and placenta and involved in the control of food intake and thermogenesis. MC-4R is expressed in the brain, and modulates feeding behavior. MC-5R is expressed unusually in many tissues, including placenta, lung, adrenal gland, brain, white fat tissue, exocrine glands, and the like. MC-5R knockout mice have been reported to have reduced sebaceous gland lipid production, though physiological activities mediated by MC-5R are not clearly known (Cell, Vol. 91, page 789, 1997).

The MSH-melanocortin receptor system is well known to be involved in regulation of immunity, and $\alpha$-MSH is reported to antagonize the action of IL-1$\alpha$, IL-6, TNF-$\alpha$ and the like, which are inflammatory cytokines, and also to induce the production IL-10, which is an anti-inflammatory cytokine (Trends in Endocrinology and Metabolism (TEM), Vol. 11, page 304, 2000).

In recent years, it has been confirmed that melanocortin system is involved in sexual function and sexual behavior. Cyclic heptapeptide (MT-II (Melanotan-II)), a melanocortin receptor nonselective agonist has been recognized to cause erection by subcutaneous administration to male adults suffering from psychogenic erectile dysfunction (Journal of Urology (J. Urol.), Vol. 160, page 389, 1998). Furthermore, it has been reported that $\alpha$-MSH administered intracerebroventricularly to male rats, causes erection, and this action is partially suppressed by administration of HS014, a selective peptide antagonist of melanocortin type 4 receptor (MC-4R) (European Journal of Pharmacology (Eur. J. Pharmacol.), Vol. 362, page 95, 1998).

It has also been confirmed that the melanocortin system, particularly, MC-4R, exerts important actions downstream of leptin in modulating food intake. Feeding behavior is an indispensable action for life maintenance in a number of living creatures including human, and abnormality of feeding behavior may result in the failure of normal life functions, and may lead to disease in many cases. In recent years, the rapid increase of obesity due to life-style changes has been recognized as a social problem. It is well known that obesity is an important risk factor for life style diseases, such as diabetes mellitus, hypertension and arteriosclerosis, and increased body weight may result in excessive burdens on the joints, such as the knee, thus causing arthritis and/or pain. In addition, the potential population who desires to lose weight is large, as suggested by the diet boom and the like, and there have been reported many cases of feeding disorders, such as bulimia and anorexia, that are caused from genetic or mental factors, such as stress. Therefore, a drug for regulating food intake is highly demanded, and research into developing an agent for preventing or treating obesity or an agent for suppressing food intake has been underway for some time.

On the other hand, many feeding regulation factors represented by leptin, have been identified. As a feeding-increasing factor acting on hypothalamus, melanin-concentrating hormone (MCH) and orexin have recently been reported in addition to neuropeptide Y (NPY). As a feeding suppressing factor, cholecystokinin (CCK) and corticotrophin-releasing hormone (CRH) and the like are known as well as the above-described $\alpha$-melanocyte-stimulating hormone ($\alpha$-MSH).

Reports that demonstrate the involvement of melanocortin system in feeding behavior or obesity include the following:

1) $A^y$ mice and $KKA^Y$ mice in which Agouti Protein, an agonist of the MC-1R, MC-3R and-4R, is overexpressed, are used as an animal model for obesity, indicating that blocking the action of MC-1R, MC-3R and-4R by Agouti Protein can lead to hyperphagia and obesity;

2) MC-4R knockout mice exhibit a similar phenotype to $A^y$ mice and $KKA^y$ mice, and can lead to severe hyperphagia, obesity, insulin-resistant diabetes (Cell, Vol. 88, page 131, 1997);

3) MT-II, a non-selective MC-R agonist injected intracerebroventricularly in feeding-increased animal models (ob/ob mice, $A^y$ mice, $KKA^y$ mice, rats or mice which are fast, or feeding-increased by administration of NPY) suppresses food intake. Furthermore, if SHU-9119 (MC-3R and 4R antagonist; MC-1R and MC-5R agonist) is injected intracerebroventricularly at the same time, the food intake suppressing activity of MT-II disappears and hyperphagia is again induced; and 4) Chronic intraperitoneal treatment of Zucker fatty rats with HP228, an $\alpha$-NDP-MSH ($\alpha$-[Nle4,D-Phe7] MSH) derivative, has been reported to activate melanocortin receptor to attenuate food intake and body weight gain over a 12-week period.

Therefore, developments are ongoing for an antiobestic drug or feeding control drug on the basis of the new feeding-suppressing action to control the action of these feeding control factors. Presently, central appetite suppressants, such as mazindol and sibutramine are on the market. However, due to their mechanism of action, which involves inhibiting the reuptake of cerebral amines such as adrenaline and serotonin, these drugs have side effects on the cardiovascular system and the like, and may cause habituation and dependence, and are thus not sufficient to completely address the disorders.

In conclusion from the above, a drug acting on melanocortin receptors, particularly MC-R agonist, is expected to act an anti-inflammatory drug, a sexual function-improving drug, an appetite suppressant, an anti-obesity drug, and the like. MC-R antagonists are also expected to act as therapeutic drugs for anorexia and other diseases due to the increase in melanocortin system, and are also expected to be used for elucidating the physiological actions of melanocortin system.

As a substance acting on melanocortin receptor, numerous lot of peptide compounds have been reported, including MT-II, HS014, SHU-9119, Q-NDP-MSH and HP228, which are the above-described α-MSH-related peptides, as well as HS024, HS028, Ro 27-3225, Ro 27-4680 and the like. On the other hand, low molecular weight compounds, such as spiropiperidine derivatives (International Publication Nos. WO 99/64002 and WO 01/70337) and piperidine derivatives (International Publication No. WO 01/70708) are known as MC-R agonists, piperidine derivatives (International Publication No. WO 00/74679) as MC-4R agonist, and aromatic amines and amide derivatives (International Publication Nos. WO 01/55106, WO 01/55107, and WO 01/55109) as substances acting on MC-R.

On the other hand, biaryl compounds are disclosed. For example, Japanese Unexamined Patent Application Publication No. 6-107649 discloses a biphenyl compound having 5-HT (serotonin) receptor antagonistic activity and 4'-[[(methoxyacetyl)methylamino]methyl]-N-[4-methoxy-3-(4-methyl-1-piperazinyl)phenyl]-2'-methyl-[1,1'-biphenyl]-4-carboamide hydrochloride in Example 10. Japanese Unexamined Patent Application Publication No. 10-510512 (International Publication No. WO 96/10559) discloses a compound represented by the formula:

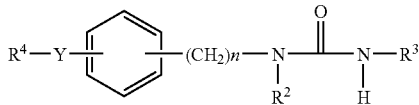

wherein $R^4$ is dialkylamino, phenyl optionally having protected amino and the like and the like; Y is a bond and the like, $R^2$ is lower alkyl and the like; $R^3$ is aryl optionally having one or more appropriate substituents and the like; and n is 0 or 1; or a salt thereof, is useful as ACAT inhibitor. However, there has been no report that a biaryl compound including these compounds acts on MC-R.

The present invention provides a novel biaryl compound or a salt thereof having the action of agonist or antagonist on melanocortin receptor (MC-R), and a drug useful as an agent for preventing or treating inflammatory diseases, such as rheumatism or sepsis, AIDS, obesity, bulimia or anorexia, or as an agent for improving sexual dysfunction or affective disorders, based on MC-R agonist /antagonist action.

DISCLOSURE OF INVENTION

As a result of extensive researches on a compound acting on melanocortin receptors (MC-R), the present inventors have first synthesized the compound represented by the following formula (I) or a salt thereof (hereinafter, called as compound (I) in some cases), and based on the structure of the compound, have found that compound (I) shows excellent MC-R agonist/antagonist activity, with low toxicity, and so is clinically useful as an agent for preventing or treating the above-described diseases. Based on these findings, the present inventors have completed the present invention.

That is, the present invention provides:

[1] A compound represented by the formula (I):

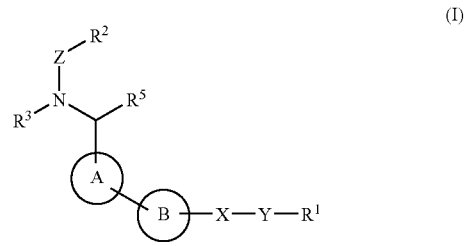

(I)

wherein ring A and ring B are optionally further substituted 6-membered aromatic rings; X is —CONR$^4$—, —SO$_2$NR$^4$—, —CH$_2$NR$^4$—, —NR$^4$CO—, —NR$^4$SO$_2$—, —NR$^4$—CO—NH—, —O—, —S—, —SO—, —SO$_2$—, —CO—, —CO$_2$—, —CH=CH— or a bond ($R^4$ is a hydrogen atom, an optionally substituted hydrocarbon group or an optionally substituted heterocyclic group); Y is a spacer having 1 to 12 atoms or a bond; Z is —CONR$^6$—, —CSNR$^6$—, —CO— or —SO$_2$— ($R^6$ is a hydrogen atom, an optionally substituted hydrocarbon group or an optionally substituted heterocyclic group); $R^1$ is an optionally substituted amino group or an optionally substituted heterocyclic group; $R^2$ is a hydrogen atom, an optionally substituted hydrocarbon group atom, an optionally substituted hydrocarbon group or an optionally substituted heterocyclic group; $R^5$ is an optionally substituted hydrocarbon group or an optionally substituted heterocyclic group (X and Y or X, Y and $R^1$ may form a ring together); or a salt thereof,

[2] The compound according to [1], wherein $R^1$ is (1) amino which may have 1 or 2 substituents selected from (a) $C_{1-10}$alkyl optionally having 1 to 3 substituents selected from (1') halogen, (2') nitro, (3') cyano, (4') oxo, (5') a hydroxy group, (6') thiol, (7') Cl$_4$alkylthio, (8') amino, (9') mono-$C_{1-4}$alkylamino, (10') di-$C_{1-4}$alkylamino, (11') 5- or 6-membered cyclic amino selected from pyrrolidine, piperazine, piperidine, morpholine, thiomorpholine, pyrrole and imidazole, (12') phenyl-$C_{1-4}$alkyl, (13') $C_{3-8}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-6}$alkyl carbamoyl, (19') $C_{3-8}$cycloalkyl carbamoyl, (20') mono-$C_{6-14}$aryl carbamoyl, (21') heterocyclic carbamoyl, (22') di-$C_{1-4}$alkyl carbamoyl, (23') $C_{1-4}$alkyl optionally substituted with halogen, $C_{3-8}$cycloalkyl or $C_{1-4}$alkoxy, (24') $C_{1-4}$alkoxy optionally substituted with halogen or $C_{1-4}$alkoxy, (25') $C_{1-4}$alkylenedioxy, (26') formyl, (27') $C_{2-4}$alkanoyl, (28') $C_{3-8}$cycloalkylcarbonyl, (29') $C_{1-4}$alkylsulfonyl, (30') $C_{1-4}$alkylsulfinyl, (31') $C_{6-14}$arylcarbonyl optionally substituted with a hydroxy group and (32') aromatic heterocyclic carbonyl (hereinafter, briefly referred to as substituent group A), (b) $C_{3-8}$cycloalkyl optionally having 1 to 3 substituents selected from the above-described substituent group A, (c) $C_{2-10}$alkenyl optionally having 1 to 3 substituents selected from the above-described substituent group A, (d) $C_{3-8}$cycloalkenyl optionally having 1 to 3 substituents selected from the above-described substituent group A, (e) $C_{2-10}$alkynyl optionally having 1 to 3 substituents selected from the above-described substituent group A, (f) $C_{6-14}$aryl optionally having 1 to 3 substituents selected from the above-described substituent group A, (g) $C_{6-14}$aryl-$C_{1-6}$alkyl optionally having 1 to 3 substituents selected from the above-described substituent group A, (h) di-$C_{6-14}$aryl-$C_{1-6}$alkyl optionally having 1 to 3 substituents selected from the above-described substituent group A, (i) tri-$C_{6-14}$aryl- $C_{1-6}$alkyl optionally having 1 to 3 substituents selected from the above-described substituent group A, (j) 5- to 8-membered aromatic heterocyclic group, or saturated or unsaturated non-aromatic heterocyclic group containing 1 to 4 hetero atoms of 1 to 3 kinds selected from an oxygen atom, a sulfur atom and a nitrogen atom and optionally having 1 to 3 substituents selected from the above-described substituent group A, (k) acyl selected from formyl, $C_{1-10}$alkylcarbonyl, $C_{3-6}$cycloalkylcarbonyl, $C_{2-10}$alkenylcarbonyl, $C_{3-8}$cycloalkenylcarbonyl, $C_{2-10}$alkynylcarbonyl, $C_{6-14}$arylcarbonyl, $C_{6-14}$aryl-$C_{1-6}$alkylcarbonyl, di-$C_{6-14}$aryl-$C_{1-6}$alkylcarbonyl, tri-$C_{6-14}$aryl-$C_{1-6}$alkylcarbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl and tri-$C_{6-14}$aryl-$C_{1-6}$alkylsulfonyl (the acyl may have 1 to 3 substituents selected from the above-described substituent group A), and (1) acyl formed by binding of 5- to 8-membered aromatic heterocyclic group, or saturated or unsaturated non-aromatic heterocyclic group containing 1 to 4 hetero atoms of 1 to 3 kinds of hetero atoms selected from an oxygen atom, a sulfur atom and a nitrogen atom to carbonyl or sulfonyl (this acyl may have 1 to 3 substituents selected from the above-described substituent group A), (2) cyclic amino optionally having 1 to 3 substituents selected from (a) halogen, (b) nitro, (c) cyano, (d) a hydroxy group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl or (3) a group formed by subtracting one hydrogen atom from a ring made by condensation of the same or different two or three rings selected from 5- to 8-membered aromatic monocyclic heterocycle, or saturated or unsaturated non-aromatic monocyclic heterocycle optionally containing 1 to 4 hetero atoms of 1 to 3 kinds of hetero atoms selected from an oxygen atom, a sulfur atom and a nitrogen atom and monocycles thereof (the heterocyclic group may have 1 to 3 substituents selected from the above-described substituent group A); $R^2$, $R^3$, $R^4$ and $R^6$ are independently (1) a hydrogen atom, (2) Clloalkyl optionally having 1 to 3 substituents selected from (1') halogen, (2') nitro, (3') cyano, (4') oxo, (5') a hydroxy group, (6') thiol, (7') $C_{1-4}$alkylthio, (8') amino group, (9') mono-$C_{1-4}$alkylamino, (10') di-$C_{1-4}$alkylamino, (11') 5- or 6-membered cyclic amino selected from pyrrolidine, piperazine, piperidine, morpholine, thiomorpholine, pyrrole, imidazole, 2-oxo-1-pyrrolidinyl, and 2-oxo-1-piperidinyl, (12') phenyl-$C_{1-4}$alkyl, (13') $C_{3-8}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-4}$alkyl carbamoyl, (19') di-$C_{1-4}$alkyl carbamoyl, (20') $C_{1-4}$alkyl optionally substituted with halogen or $C_{1-4}$alkoxy, (21') $C_{1-4}$alkoxy optionally substituted with halogen or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl [this $C_{6-14}$aryl may be substituted with a substituent selected from (1") halogen, (2") nitro, (3") cyano, (4") a hydroxy group, (5") thiol, (6") $C_{1-4}$alkylthio, (7") amino, (8") mono-$C_{1-4}$alkylamino, (9") di-$C_{1-4}$alkylamino, (10") 5- or 6-membered cyclic amino selected from pyrrolidine, piperazine, piperidine, morpholine, thiomorpholine, pyrrole and imidazole, (11") phenyl-$C_{1-4}$alkyl, (12") $C_{3-8}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl carbamoyl, (18") di-$C_{1-4}$alkyl carbamoyl, (19") $C_{1-4}$alkyl optionally substituted with halogen or $C_{1-4}$alkoxy, (20") $C_{1-4}$alkoxy optionally substituted with halogen or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl and (29") 5- or 6-membered aromatic monocyclic heterocyclic group] and (31') 5- to 8-membered aromatic heterocyclic group or saturated or unsaturated non-aromatic heterocyclic group containing 1 to 4 hetero atoms of 1 to 3 kinds selected from an oxygen atom, a sulfur atom and a nitrogen atom [these heterocyclic groups may have 1 to 3 substituents selected from (1") halogen, (2") nitro, (3") cyano, (4") oxo, (5") a hydroxy group, (6") thiol, (7") $C_{1-4}$alkylthio, (8") amino, (9") mono-$C_{1-4}$alkylamino, (10") di-$C_{1-4}$alkylamino, (11") 5- or 6-membered cyclic amino selected from pyrrolidine, piperazine, piperidine, morpholine, thiomorpholine, pyrrole and imidazole, (12") phenyl-$C_{1-4}$alkyl, (13") $C_{3-8}$cycloalkyl, (14") carboxyl, (15") $C_{1-4}$alkoxy-carbonyl, (16") $C_{7-10}$aralkyloxy-carbonyl, (17") carbamoyl, (18") mono-$C_{1-4}$alkyl carbamoyl, (19") di-$C_{1-4}$alkyl carbamoyl, (20") $C_{1-4}$alkyl optionally substituted with halogen or $C_{1-4}$alkoxy, (21") $C_{1-4}$alkoxy optionally substituted with halogen or $C_{1-4}$alkoxy, (22") $C_{1-4}$alkylenedioxy, (23") formyl, (24") $C_{2-4}$alkanoyl, (25") $C_{1-4}$alkylsulfonyl, and (26") $C_{1-4}$alkylsulfinyl] (hereinafter, briefly referred to as substituent group B), (3) $C_{3-8}$cycloalkyl optionally having 1 to 3 substituents selected from the above-described substituent group B, (4) $C_{2-10}$alkenyl optionally having 1 to 3 substituents selected from the above-described substituent group B, (5) $C_{3-8}$cycloalkenyl optionally having 1 to 3 substituents selected from the above-described substituent group B, (6) $C_{2-10}$alkynyl optionally having 1 to 3 substituents selected from the above-described substituent group B, (7) $C_{3-8}$cycloalkyl-$C_{1-6}$alkyl optionally having 1 to 3 substituents selected from the above-described substituent group B, (8) $C_{6-14}$aryl optionally having 1 to 3 substituents selected from the above-described substituent group B, (9) $C_{6-14}$aryl-$C_{1-6}$alkyl optionally having 1 to 3 substituents selected from the above-described substituent group B, (10) di-$C_{6-14}$aryl-$C_{1-6}$alkyl optionally having 1 to 3 substituents selected from the above-described substituent group B, (11) tri-$C_{6-14}$aryl-$C_{1-6}$alkyl optionally having 1 to 3 substituents selected from the above-described substituent group B, (12) the formula —X'''-G-(CH$_2$)$_n$-J [wherein X''' is $C_{1-4}$alkylene or $C_{2-4}$alkenylene, G is a bond, —O—, —S—, —CO—NH— or —NH—CO—, n is an integer of 0 to 3, J is (a) $C_{6-14}$aryl (this $C_{6-14}$aryl may have 1 to 3 substituents selected from (1") halogen, (2") nitro, (3") cyano, (4") a hydroxy group, (5") thiol, (6") $C_{1-4}$alkylthio, (7") amino, (8") mono-$C_{1-4}$alkylamino, (9") di-$C_{1-4}$alkylamino, (10") 5- or 6-membered cyclic amino selected from pyrrolidine, piperazine, piperidine, morpholine, thiomorpholine, pyrrole, imidazole, 2-oxo-1-pyrrolidinyl and 2-oxo-1-piperidinyl, (11") phenyl-$C_{1-4}$alkyl, (12") $C_{3-8}$cycloalkyl, (13") carboxyl, (14") $C_{1-4}$alkoxy-carbonyl, (15") $C_{7-10}$aralkyloxy-carbonyl, (16") carbamoyl, (17") mono-$C_{1-4}$alkyl carbamoyl, (18") di-$C_{1-4}$alkyl carbamoyl, (19") $C_{1-4}$alkyl optionally substituted with halogen or $C_{1-4}$alkoxy, (20") $C_{1-4}$alkoxy optionally substituted with halogen or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, (29") $C_{6-14}$aryl [this $C_{6-14}$aryl may be substituted with a substituent selected from (1''') halogen, (2''') nitro, (3''') cyano, (4''') a hydroxy group, (5''') thiol, (6''') $C_{1-4}$alkylthio, (7''') amino, (8''') mono-$C_{1-4}$alkylamino, (9''') di-$C_{1-4}$alkylamino, (10''') 5- or 6-membered cyclic amino selected from pyrrolidine, piperazine, piperidine, morpholine, thiomorpholine, pyrrole and imidazole, (11''') phenyl-$C_{1-4}$alkyl, (12''') $C_{3-8}$cycloalkyl, (13''') carboxyl group, (14''') $C_{1-4}$alkoxy-carbonyl, (15''') $C_{7-10}$aralkyloxy-carbonyl, (16''')

carbamoyl, (17''') mono-$C_{1-4}$alkyl carbamoyl, (18''') di-$C_{1-4}$alkyl carbamoyl, (19''') $C_{1-4}$alkyl optionally substituted with halogen or $C_{1-4}$alkoxy, (20''') $C_{1-4}$alkoxy optionally substituted with halogen or $C_{1-4}$alkoxy, (21''') $C_{1-4}$alkylenedioxy, (22''') formyl, (23''') $C_{2-4}$alkanoyl, (24''') $C_{1-4}$alkylsulfonyl, (25''') $C_{1-4}$alkylsulfinyl, (26''') sulfamoyl, (27''') mono-$C_{1-4}$alkylsulfamoyl, (28''') di-$C_{1-4}$alkylsulfamoyl and (29''') 5- or 6-membered aromatic monocyclic heterocyclic group] and (30''') 5- to 8-membered aromatic heterocyclic group, or saturated or unsaturated non-aromatic heterocyclic group containing 1 to 4 hetero atoms consisting of 1 to 3 kinds of hetero atoms selected from an oxygen atom, a sulfur atom and a nitrogen atom [these heterocyclic groups may have 1 to 3 substituents selected from the above-described substituent group A]) or (b) 5- to 8-membered aromatic heterocyclic group containing 1 to 4 hetero atoms consisting of 1 to 3 kinds of hetero atoms selected from an oxygen atom, a sulfur atom and a nitrogen atom (this aromatic heterocyclic group may have 1 to 3 substituents selected from the above-described substituent group A)], (13) a group represented by the formula —X''''-L-(CH$_2$)$_n$-M [wherein X'''' is a bond or $C_{1-4}$alkylene optionally having 1 to 3 substituents selected from the above-described substituent group B, L is (a) a bond, (b) $C_{6-10}$aryl (this $C_{6-10}$aryl may have 1 to 3 substituents selected from the above-described substituent group A), (c) 5- to 8-membered aromatic heterocyclic group containing 1 to 4 hetero atoms consisting of 1 to 3 kinds of hetero atoms selected from an oxygen atom, a sulfur atom and a nitrogen atom (this aromatic heterocyclic group may have 1 to 3 substituents selected from the above-described substituent group A), (d) —O—, (e) —S—, (f) —CO—NH— or (g) —NH—CO—, n is an integer of 0 to 3, M is an amino group, a guanidino group, a sulfamoyl group, a hydroxy group or a carbamoyl group (provided that when X'''' and L are a bond, n is not 0)] or (14) a group formed by subtracting one hydrogen atom from a ring made by condensation of the same or different two or three rings selected from 5- to 8-membered aromatic monocyclic heterocycle, or saturated or unsaturated non-aromatic monocyclic heterocycle optionally containing 1 to 4 hetero atoms of 1 to 3 kinds of hetero atoms selected from an oxygen atom, a sulfur atom and a nitrogen atom and monocycles thereof (the heterocyclic group may have 1 to 3 substituents selected from the above-described substituent group A); $R^5$ is (1) $C_{1-10}$alkyl optionally having 1 to 3 substituents selected from the above-described substituent group B, (2) $C_{3-8}$cycloalkyl optionally having 1 to 3 substituents selected from the above-described substituent group B, (3) $C_{2-10}$alkenyl optionally having 1 to 3 substituents selected from the above-described substituent group B, (4) $C_{3-8}$cycloalkenyl optionally having 1 to 3 substituents selected from the above-described substituent group B, (5) $C_{2-10}$alkynyl optionally having 1 to 3 substituents selected from the above-described substituent group B, (6) $C_{3-8}$cycloalkyl-$C_{1-6}$alkyl optionally having 1 to 3 substituents selected from the above-described substituent group B, (7) $C_{6-14}$aryl optionally having 1 to 3 substituents selected from the above-described substituent group B, (8) $C_{6-14}$aryl-$C_{1-6}$alkyl optionally having 1 to 3 substituents selected from the above-described substituent group B, (9) di-$C_{6-14}$aryl-$C_{1-6}$alkyl optionally having 1 to 3 substituents selected from the above-described substituent group B, (10) tri-$C_{6-14}$aryl-$C_{1-6}$alkyl optionally having 1 to 3 substituents selected from the above-described substituent group B, (11) the formula —X'''-G-(CH$_2$)$_n$-J [wherein X''' is $C_{1-4}$alkylene or $C_{2-4}$alkenylene, G is a bond, —O—, —S—, —CO—NH— or —NH—CO—, n is an integer of 0 to 3, J is (a) $C_{6-14}$aryl (this $C_{6-14}$aryl may have 1 to 3 substituents selected from (1'') halogen, (2'') nitro, (3'') cyano, (4'') a hydroxy group, (5'') thiol, (6'') $C_{1-4}$alkylthio, (7'') amino, (8'') mono-$C_{1-4}$alkylamino, (9'') di-$C_{1-4}$alkylamino, (10'') 5- or 6-membered cyclic amino selected from pyrrolidine, piperazine, piperidine, morpholine, thiomorpholine, pyrrole, imidazole, 2-oxo-1-pyrrolidinyl and 2-oxo-1-piperidinyl, (11'') phenyl-$C_{1-4}$alkyl, (12'') $C_{3-8}$cycloalkyl, (13'') carboxyl, (14'') $C_{1-4}$alkoxy-carbonyl, (15'') $C_{7-10}$aralkyloxy-carbonyl, (16'') carbamoyl, (17'') mono-$C_{1-4}$alkyl carbamoyl, (18'') di-$C_{1-4}$alkyl carbamoyl, (19'') $C_{1-4}$alkyl optionally substituted with halogen or $C_{1-4}$alkoxy, (20'') $C_{1-4}$alkoxy optionally substituted with halogen or $C_{1-4}$alkoxy, (21'') $C_{1-4}$alkylenedioxy, (22'') formyl, (23'') $C_{2-4}$alkanoyl, (24'') $C_{1-4}$alkylsulfonyl, (25'') $C_{1-4}$alkylsulfinyl, (26'') sulfamoyl, (27'') mono-$C_{1-4}$alkylsulfamoyl, (28'') di-$C_{1-4}$alkylsulfamoyl, (29'') $C_{6-14}$aryl [this $C_{6-14}$aryl may be substituted with a substituent selected from (1''') halogen, (2''') nitro, (3''') cyano, (4''') a hydroxy group, (5''') thiol, (6''') $C_{1-4}$alkylthio, (7''') amino, (8''') mono-$C_{1-4}$alkylamino, (9''') di-$C_{1-4}$alkylamino, (10''') 5- or 6-membered cyclic amino selected from pyrrolidine, piperazine, piperidine, morpholine, thiomorpholine, pyrrole and imidazole, (11''') phenyl-$C_{1-4}$alkyl, (12''') $C_{3-8}$cycloalkyl, (13''') carboxyl group, (14''') $C_{1-4}$alkoxy-carbonyl, (15''') $C_{7-10}$aralkyloxy-carbonyl, (16''') carbamoyl, (17''') mono-$C_{1-4}$alkyl carbamoyl, (18''') di-$C_{1-4}$alkyl carbamoyl, (19''') $C_{1-4}$alkyl optionally substituted with halogen or $C_{1-4}$alkoxy, (20''') $C_{1-4}$alkoxy optionally substituted with halogen or $C_{1-4}$alkoxy, (21''') $C_{1-4}$alkylenedioxy, (22''') formyl, (23''') $C_{2-4}$alkanoyl, (24''') $C_{1-4}$alkylsulfonyl, (25''') $C_{1-4}$alkylsulfinyl, (26''') sulfamoyl, (27''') mono-$C_{1-4}$alkylsulfamoyl, (28''') di-$C_{1-4}$alkylsulfamoyl, and (29''') 5- or 6-membered aromatic monocyclic heterocyclic group] and (30'') 5- to 8-membered aromatic heterocyclic group or saturated or unsaturated non-aromatic heterocyclic group containing 1 to 4 hetero atoms of 1 to 3 kinds selected from an oxygen atom, a sulfur atom and a nitrogen atom [these heterocyclic groups may have 1 to 3 substituents selected from the above-described substituent group A]) or (b) 5- to 8-membered aromatic heterocyclic group containing 1 to 4 hetero atoms consisting of 1 to 3 kinds of hetero atoms selected from an oxygen atom, a sulfur atom and a nitrogen atom (this aromatic heterocyclic group may have 1 to 3 substituents selected from the above-described substituent group A)], (12) a group represented by the formula —X''''-L-(CH$_2$)$_n$-M [wherein X'''' is a bond, or $C_{1-4}$alkylene optionally having 1 to 3 substituents selected from the above-described substituent group B, L is (a) a bond, (b) $C_{6-10}$aryl (this $C_{6-10}$aryl may have 1 to 3 substituents selected from the above-described substituent group A), (c) 5- to 8-membered aromatic heterocyclic group containing 1 to 4 hetero atoms consisting of 1 to 3 kinds of hetero atoms selected from an oxygen atom, a sulfur atom and a nitrogen atom (this aromatic heterocyclic group may have 1 to 3 substituents selected from the above-described substituent group A), (d) —O—, (e) —S—, (f) —CO—NH— or (g) —NH—CO—, n is an integer of 0 to 3, M is an amino group, a guanidino group, a sulfamoyl group, a carbamoyl group or a hydroxy group (provided that when X'''' and L are a bond, n is not 0)] or (13) a group formed by subtracting one hydrogen atom from a ring made by condensation of the same or different two or three rings selected from 5- to 8-membered aromatic monocyclic heterocycle, or saturated or unsaturated non-aromatic monocyclic heterocycle optionally containing 1 to 4 hetero atoms consisting of 1 to 3 kinds of hetero atoms selected from an oxygen atom, a sulfur atom and a nitrogen atom and monocycles thereof (the heterocyclic group may have 1 to 3 substituents selected from the above-described substituent group A); and Y is a saturated divalent group of (1) —(CH$_2$)$_{f1}$— (f1 is an integer of 1 to 12), (2) —(CH$_2$)$_{g1}$—

$Y^1$—$(CH_2)_{g2}$— (g1 and g2 are the same or different and an integer of 0 to 11, provided that the sum of g1 and g2 is 0 to 11. $Y^1$ is NH, O, S, SO or $SO_2$) or (3) —$(CH_2)_{h1}$—$Y^1$—$(CH_2)_{h2}$—$Y^2$—$(CH_2)_{h3}$— (h1, h2 and h3 are the same or different and an integer of 0 to 10, provided that the sum of h1, h2 and h3 is between 0 to 10. $Y^1$ and $Y^2$ are independently NH, O, S, SO or $SO_2$, provided that when h2 is 0, at least one of $Y^1$ and $Y^2$ is preferably NH.) and divalent group thereof wherein some bonds of the divalent group are converted to unsaturated bonds (this group may have a substituent selected from (a) $C_{1-10}$alkyl optionally having 1 to 3 substituents selected from the above-described substituent group B, (b) $C_{3-8}$cycloalkyl optionally having 1 to 3 substituents selected from the above-described substituent group B, (c) $C_{2-10}$alkenyl optionally having 1 to 3 substituents selected from the above-described substituent group B, (d) $C_{3-8}$cycloalkenyl optionally having 1 to 3 substituents selected from the above-described substituent group B, (e) $C_{2-10}$alkynyl optionally having 1 to 3 substituents selected from the above-described substituent group B, and (f) $C_{3-8}$cycloalkyl-$C_{1-6}$alkyl optionally having 1 to 3 substituents selected from the above-described substituent group B),

[3] The compound according to [1], wherein ring A and ring B are optionally further substituted benzene rings,

[4] The compound according to [1] represented by the following formula:

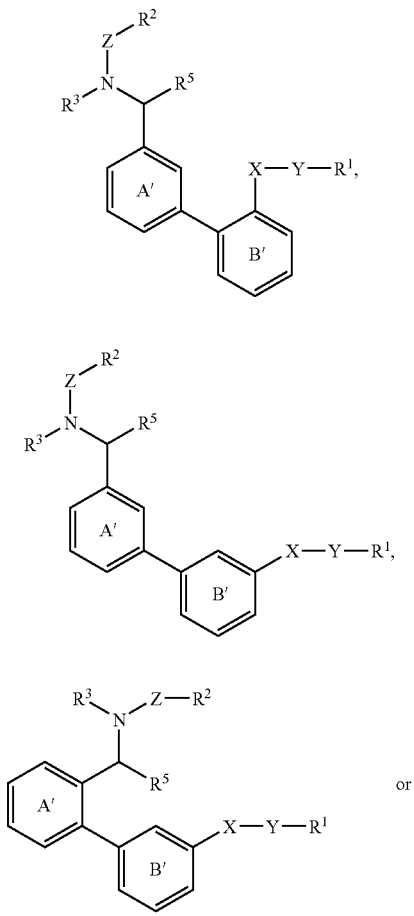

-continued

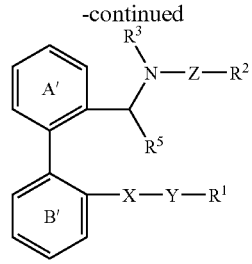

wherein ring A' and ring B' are optionally further substituted benzene rings, and the other symbols are the same as defined in [1]],

[5] The compound according to [1] represented by the following formula:

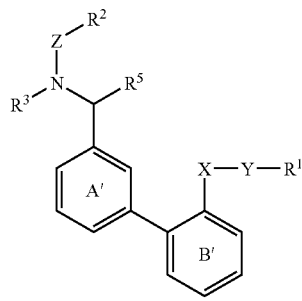

wherein ring A' and ring B' are optionally further substituted benzene rings, and the other symbols are the same as defined in [1]],

[6] The compound according to [1], wherein $R^1$ is (1) amino optionally substituted with (1') $C_{1-10}$alkyl optionally substituted with carbamoyl or (2') $C_{1-10}$alkylcarbonyl optionally substituted with amino or (2) cyclic amino; $R^2$ is (1) $C_{1-10}$alkyl optionally substituted with pyridyl or $C_{6-14}$aryloxy, (2) $C_{3-8}$cycloalkyl-$C_{1-6}$alkyl optionally substituted with $C_{1-4}$alkyl, (3) $C_{6-14}$aryl, or (4) $C_{6-14}$aryl-alkyl optionally substituted with a substituent selected from (i) halogen, (ii) $C_{1-4}$alkyl optionally halogenated and (iii) $C_{1-4}$alkoxy; $R^3$ is (1) piperidinyl optionally substituted with a substituent selected from (1') phenyl-$C_{1-4}$alkyl, (2') mono-$C_{1-6}$alkyl carbamoyl, (3') $C_{3-8}$cycloalkyl carbamoyl, (4') heterocyclic carbamoyl, (5') mono-$C_{6-14}$aryl carbamoyl, (6') $C_{1-4}$alkyl optionally substituted with $C_{3-8}$cycloalkyl, (7') $C_{2-4}$alkanoyl, (8') $C_{3-8}$cycloalkylcarbonyl, (9') $C_{6-14}$arylcarbonyl optionally substituted with a hydroxy group and (10') aromatic nitrogen-containing or aromatic oxygen-containing heterocyclic carbonyl or (2) pyrrolidinyl optionally substituted with a substituent selected from (1') phenyl-$C_{1-4}$alkyl, (2') mono-$C_{1-6}$alkyl carbamoyl, (3') $C_{3-8}$cycloalkyl carbamoyl, (4') heterocyclic carbamoyl, (5') mono-$C_{6-14}$aryl carbamoyl, (6') $C_{1-4}$alkyl optionally substituted with $C_{3-8}$cycloalkyl, (7') $C_{2-4}$alkanoyl, (8') $C_{3-8}$cycloalkylcarbonyl, (9') $C_{6-14}$arylcarbonyl optionally substituted with a hydroxy group and (10') aromatic nitrogen-containing or aromatic oxygen-containing heterocyclic carbonyl; $R^5$ is $C_{1-4}$alkyl, X is a bond, —CONH—, —NHCO— or —$CO_2$—, Y is $C_{2-4}$alkylene optionally substituted with $C_{1-6}$alkyl; Z is —CO—, or, X, Y and $R^1$ form piperazylcarbonyl together,

[7] The compound according to [1], wherein $R^1$ is amino,

[8] The compound according to [1], wherein $R^5$ is methyl,

[9] A prodrug of the compound according to [1] or a salt thereof,

[10] N-(2-aminoethyl)-3'-[1-{N-(1-benzylpiperidin-4-yl)-N-(2-naphthylacetyl)amino}ethyl][1,1'-biphenyl]-2-carboxamide, N-(2-aminoethyl)-3'-[1-{N-(1-benzylpiperidin-4-yl)-N-(4-chlorophenylacetyl)amino}ethyl][1,1'-biphenyl]-2-carboxamide, N-(2-aminoethyl)-3'-[1-{N-(1-benzylpiperidin-4-yl)-N-(3-chlorophenylacetyl)amino}ethyl][1,1'-biphenyl]-2-carboxamide, N-(2-aminoethyl)-3'-[1-{N-(1-benzylpiperidin-4-yl)-N-(4-bromophenylacetyl)amino}ethyl][1,1'-biphenyl]-2-carboxamide, N-(2-aminoethyl)-3'-[1-{N-(1-benzylpiperidin-4-yl)-N-(3,4-dichlorophenylacetyl)amino}ethyl][1,1'-biphenyl]-2-carboxamide, N-(2-aminoethyl)-3'-[1-(N-(4-chlorophenylacetyl)-N-(1-(2-indolecarbonyl)piperidin-4-yl)amino}ethyl][1,1'-biphenyl]-2-carboxamide, N-(2-aminoethyl)-3'-[1-{N-(1-(2-benzofurancarbonyl)piperidin-4-yl)-N-(4-chlorophenylacetyl)amino}ethyl][1,1'-biphenyl]-2-carboxamide, N-(2-aminoethyl)-3'-[1-{N-(4-chlorophenylacetyl)-N-(1-(4-hydroxybenzoyl)piperidin-4-yl)amino}ethyl][1,1'-biphenyl]-2-carboxamide or a salt thereof,

[11] A drug comprising the compound according to [1] or a salt thereof or a prodrug thereof,

[12] A melanocortin receptor modulator comprising a compound represented by the formula (I'):

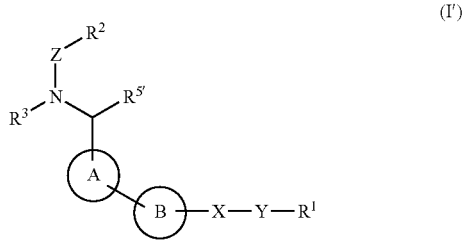

wherein ring A and ring B are optionally further substituted 6-membered aromatic rings; X is —CONR$^4$—, —SO$_2$NR$^4$—, —CH$_2$NR$^4$—, —NR$^4$CO—, —NR$^4$SO$_2$—, —NR$^4$—CO—NH—, —O—, —S—, —SO—, —SO$_2$—, —CO—, —CO$_2$—, —CH=CH— or a bond wherein R$^4$ is a hydrogen atom, an optionally substituted hydrocarbon group or an optionally substituted heterocyclic group; Y is a spacer having 1 to 12 atoms or a bond; Z is —CONR$^6$—, —CSNR$^6$—, —CO— or —SO$_2$— wherein R$^6$ is a hydrogen atom, an optionally substituted hydrocarbon group or an optionally substituted heterocyclic group; R$^1$ is an optionally substituted amino group or an optionally substituted heterocyclic group; R$^2$ is a hydrogen atom, an optionally substituted hydrocarbon group or an optionally substituted heterocyclic group; R$^3$ is a hydrogen atom, an optionally substituted hydrocarbon group or an optionally substituted heterocyclic group; and R$^5$ is a hydrogen atom, an lo optionally substituted hydrocarbon group or an optionally substituted heterocyclic group (X and Y or X, Y and R$^1$ may form a ring together)]; or a salt thereof,

[13] The modulator according to [12], which is a melanocortin receptor agonist or antagonist,

[14] An agent for preventing or treating inflammatory diseases, AIDS, obesity, bulimia or anorexia and/or an agent for improving affective disorder or sexual dysfunction comprising a compound represented by the formula (I'):

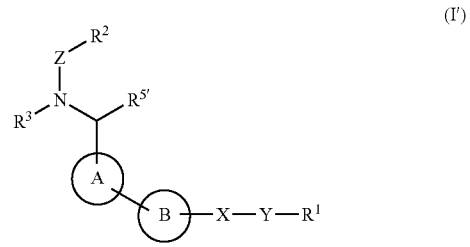

wherein ring A and ring B are optionally further substituted 6-membered aromatic rings; X is —CONR$^4$—, —SO$_2$NR$^4$—, —CH$_2$NR$^4$—, —NR$^4$CO—, —NR$^4$SO$_2$—, —NR$^4$—CO—NH—, —O—, —S—, —SO—, —SO$_2$—, —CO—, —CO$_2$—, —CH=CH— or a bond wherein R$^4$ is a hydrogen atom, an optionally substituted hydrocarbon group or an optionally substituted heterocyclic group; Y is a spacer having 1 to 12 atoms or a bond; Z is —CONR$^6$—, —CSNR$^6$—, —CO— or —SO$_2$— wherein R$^6$ is a hydrogen atom, an optionally substituted hydrocarbon group or an optionally substituted heterocyclic group; R$^1$ is an optionally substituted amino group or an optionally substituted heterocyclic group; R$^2$ is a hydrogen atom, an optionally substituted hydrocarbon group or an optionally substituted heterocyclic group; R$^3$ is a hydrogen atom, an optionally substituted hydrocarbon group or an optionally substituted heterocyclic group; and R$^5$ is a hydrogen atom, an optionally substituted hydrocarbon group or an optionally substituted heterocyclic group (X and Y or X, Y and R$^1$ may form a ring together)] or a salt thereof,

[15] The agent according to [14] for preventing or treating obesity or bulimia,

[16] A method of agonizing or antagonizing a melanocortin receptor comprising administering to a mammal an effective amount of a compound represented by the formula (I'):

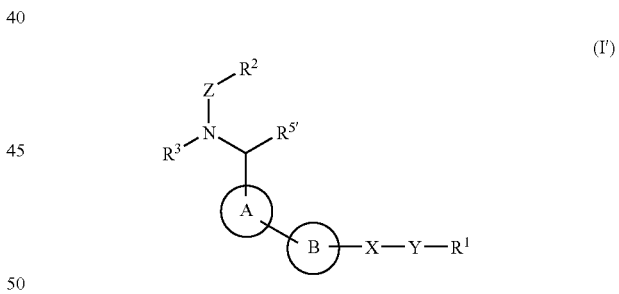

wherein ring A and ring B are optionally further substituted 6-membered aromatic rings; X is —CONR$^4$—, —SO$_2$NR$^4$—, —CH$_2$NR$^4$—, —NR$^4$CO—, —NR$^4$SO$_2$—, —NR$^4$—CO—NH—, —O—, —S—, —SO—, —SO$_2$—, —CO—, —CO$_2$—, —CH=CH— or a bond wherein R$^4$ is a hydrogen atom, an optionally substituted hydrocarbon group or an optionally substituted heterocyclic group; Y is a spacer having 1 to 12 atoms or a bond; Z is —CONR$^6$—, —CSNR$^6$—, —CO— or —SO$_2$— wherein R$^6$ is a hydrogen atom, an optionally substituted hydrocarbon group or an optionally substituted heterocyclic group; R$^1$ is an optionally substituted amino group or an optionally substituted heterocyclic group; R$^2$ is a hydrogen atom, an optionally substituted hydrocarbon group or an optionally substituted heterocyclic group; R$^3$ is a hydrogen atom, an optionally substituted hydrocarbon group or an optionally substituted heterocyclic group; and $R^{5'}$ is a hydrogen atom, an optionally substituted hydrocarbon group or an optionally substituted heterocyclic group (X and Y or X, Y and $R^1$ may form a ring together)] or a salt thereof,

[17] A method of preventing or treating inflammatory diseases, AIDS, obesity, bulimia or anorexia and/or a method of improving affective disorder or sexual dysfunction comprising administering to a mammal an effective amount of a compound represented by the formula (I'):

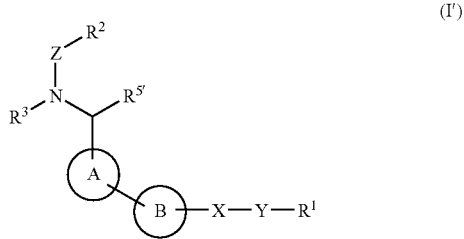

(I')

wherein ring A and ring B are optionally further substituted 6-membered aromatic rings; X is —$CONR^4$—, —$SO_2NR^4$—, —$CH_2NR^4$—, —$NR^4CO$—, —$NR^4SO_2$—, —$NR^4$—CO—NH—, —O—, —S—, —SO—, —$SO_2$—, —CO—, —$CO_2$—, —CH=CH— or a bond wherein $R^4$ is a hydrogen atom, an optionally substituted hydrocarbon group or an optionally substituted heterocyclic group; Y is a spacer having 1 to 12 atoms or a bond; Z is —$CONR^6$—, —$CSNR^6$—, —CO— or —$SO_2$— wherein $R^6$ is a hydrogen atom, an optionally substituted hydrocarbon group or an optionally substituted heterocyclic group; $R^1$ is an optionally substituted amino group or an optionally substituted heterocyclic group; $R^2$ is a hydrogen atom, an optionally substituted hydrocarbon group or an optionally substituted heterocyclic group; $R^3$ is a hydrogen atom, an optionally substituted hydrocarbon group or an optionally substituted heterocyclic group; and $R^5$ is a hydrogen atom, an optionally substituted hydrocarbon group or an optionally substituted heterocyclic group (X and Y or X, Y and $R^1$ may form a ring together)] or a salt thereof, and

[18] Use of a compound represented by the formula (I'):

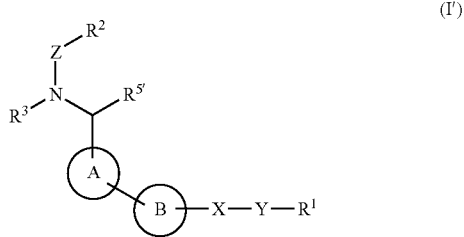

(I')

wherein ring A and ring B are optionally further substituted 6-membered aromatic rings; X is —$CONR^4$—, —$SO_2NR^4$—, —$CH_2NR^4$—, —$NR^4CO$—, —$NR^4SO_2$—, —$NR^4$—CO—NH—, —O—, —S—, —SO—, —$SO_2$—, —CO—, —$CO_2$—, —CH=CH— or a bond wherein $R^4$ is a hydrogen atom, an optionally substituted hydrocarbon group or an optionally substituted heterocyclic group; Y is a spacer having 1 to 12 atoms or a bond; Z is —$CONR^6$—, —$CSNR^6$—, —CO— or —$SO_2$— wherein $R^6$ is a hydrogen atom, an optionally substituted hydrocarbon group or an optionally substituted heterocyclic group; $R^1$ is an optionally substituted amino group or an optionally substituted heterocyclic group; $R^2$ is a hydrogen atom, an optionally substituted hydrocarbon group or an optionally substituted heterocyclic group; $R^3$ is a hydrogen atom, an optionally substituted hydrocarbon group or an optionally substituted heterocyclic group; and $R^5$ is a hydrogen atom, an optionally substituted hydrocarbon group or an optionally substituted heterocyclic group (X and Y or X, Y and $R^1$ may form a ring together)] or a salt thereof for preparing an agent for preventing or treating inflammatory diseases, AIDS, obesity, ulimia or anorexia and/or an agent for improving affective disorder or sexual dysfunction.

In the above-described formula (I), "optionally further substituted 6-membered aromatic ring" represented by ring A and ring B, refers to a benzene ring, a pyridine ring, a pyrazine ring, a pyrimidine ring, pyridazine ring and the like s that may have other substituents than the substituent clearly stated in the formula (I). Examples of the substituents (substituents other than those clearly stated in formula (I)) include an optionally substituted hydrocarbon group, an optionally substituted heterocyclic group, a nitro group, lo halogen, an optionally substituted amino group, a group represented by the formula $R^7$-Q- wherein Q is an oxygen atom or an optionally oxidized sulfur atom (for example, S, SO, $SO_2$ and the like), and $R^7$ is an optionally substituted hydrocarbon group or an optionally substituted heterocyclic group), a cyano group, optionally substituted acyl group, an optionally esterified or amidated carboxyl group and the like.

Examples of the "hydrocarbon group" in the "optionally substituted hydrocarbon group" as an optional substituent of the "optionally further substituted 6-membered aromatic ring" represented by ring A and ring B and in "an optionally substituted hydrocarbon group" represented by $R^7$, include (1) alkyl (for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$) alkyl and the like); (2) cycloalkyl (for example, $C_{3-8}$cycloalkyl such as cyclopropyl, cyclobutyl, cyclopentyl, cyclohexyl and cycloheptyl, and the like); in addition, the cycloalkyl may be condensed with a benzene ring to form indane (for example, indan-1-yl, indan-2-yl and the like), tetrahydronaphthalene (for example, tetrahydronaphthalen-5-yl, tetrahydronaphthalen-6-yl and the like) and the like (preferably, indane and the like); in addition, the cycloalkyl may be cross-linked through a straight chain having 1 or 2 carbon atoms to form a cross-linked cyclic hydrocarbon residue such as bicyclo[2.2.1]heptyl, bicyclo[2.2.2]octyl, bicyclo[3.2.1]octyl, bicyclo[3.2.2]nonyl and the like (preferably, cyclohexyl having a link of a straight chain having 1 or 2 carbon atoms and the like, more preferably, bicyclo[2.2.1]heptyl and the like); (3) alkenyl (for example, $C_{2-10}$alkenyl such as vinyl, allyl, crotyl, 2-heptenyl and 3-hexenyl, preferably lower ($C_{2-6}$)alkenyl and the like); (4) cycloalkenyl (for example, $C_{3-8}$cycloalkenyl such as 2-cycloheptenyl, 2-cyclohexenyl, 2-cycloheptenylmethyl and 2-cyclohexenylmethyl and the like); (5) alkynyl (for example $C_{2-10}$alkynyl such as ethynyl, 1-propynyl, 2-propynyl, 1-butynyl, 2-pentynyl and 3-hexynyl, preferably lower ($C_{26}$)alkynyl and the like); (6) aryl (for example, $C_{6-14}$aryl such as phenyl and naphthyl, preferably $C_{6-10}$aryl, more preferably phenyl and the like); and (7) aralkyl (for example, $C_{1-6}$alkyl having 1 to 3 $C_{6-14}$aryls, preferably, phenyl-$C_{1-4}$alkyl (for example, benzyl, phenethyl and the like) and the like); among others, alkyl is preferable, $C_{1-4}$alkyl such as methyl, ethyl and the like is more preferable, and methyl is most preferable.

The hydrocarbon group may have a substituent, and examples of the substituent include (1) halogen (for example, fluorine, chlorine, bromine, iodine and the like), (2) nitro, (3) cyano, (4) oxo (provided that it may not join the hydrocarbon group to form an acyl group), (5) a hydroxy group, (6) an optionally substituted thiol group (for example, thiol, $C_{1-4}$alkylthio and the like), (7) an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole and the like), (8) phenyl-lower ($C_{1-4}$)alkyl, (9) $C_{3-8}$cycloalkyl, (10) an optionally esterified or amidated carboxyl group (for example, carboxyl, $C_{1-4}$alkoxy-carbonyl, $C_{7-10}$aralkyloxy-carbonyl, carbamoyl, mono-$C_{1-6}$alkyl carbamoyl, $C_{3-8}$cycloalkyl carbamoyl, mono-$C_{6-14}$aryl carbamoyl, heterocyclic carbamoyl (for example, furylcarbamoyl, thienylcarbamoyl, pyridyl carbamoyl, pyrazylcarbamoyl, pyrimidylcarbamoyl and the like), di-$C_{1-4}$alkyl carbamoyl and the like), (11) $C_{1-4}$alkyl that may have halogen, $C_{3-8}$cycloalkyl or $C_{1-4}$alkoxy (for example, trifluoromethyl, methyl, ethyl, cyclohexylmethyl and the like), (12) $C_{1-4}$alkoxy that may have halogen or $C_{1-4}$alkoxy (for example, methoxy, ethoxy, trifluoromethoxy, trifluoroethoxy and the like), (13) $C_{1-4}$alkylenedioxy (for example, —O—CH$_2$—O—, —O—CH$_2$—CH$_2$—O— and the like), (14) formyl, (15) $C_{2-4}$alkanoyl (for example, acetyl, propionyl and the like), (16) $C_{3-8}$cycloalkylcarbonyl (for example, cyclopropylcarbonyl, cyclobutylcarbonyl, cyclopentylcarbonyl, cyclohexylcarbonyl, cycloheptylcarbonyl, cyclooctylcarbonyl and the like), (17) $C_{1-4}$alkylsulfonyl (for example, methanesulfonyl, ethanesulfonyl and the like), (18) $C_{1-4}$alkylsulfinyl (for example, methanesulfinyl, ethanesulfinyl and the like), (19) $C_{6-14}$arylcarbonyl optionally substituted with a hydroxy group (for example, benzoyl, 2-hydroxybenzoyl, 3-hydroxybenzoyl, 4-hydroxybenzoyl and the like) and (20) aromatic heterocyclic carbonyl (for example, furylcarbonyl, thienylcarbonyl, pyrrolylcarbonyl, pyridylcarbonyl, pyrazylcarbonyl, pyrimidylcarbonyl, pyridazylcarbonyl and the like). The number of the substituents is preferably 1 to 3.

Examples of the "heterocyclic group" in the "optionally substituted heterocyclic group" that the "optionally further substituted 6-membered aromatic ring" represented by ring A and ring B has optionally as a substituent and, in the "optionally substituted heterocyclic group" represented by $R^7$, include, for example, a group formed by subtracting one hydrogen atom from 5- to 8-membered aromatic heterocycle, saturated or unsaturated non-aromatic heterocycle (aliphatic heterocycle) and the like containing at least 1 (preferably 1 to 4, more preferably 1 or 2) hetero atoms consisting of 1 to 3 kinds (preferably 1 or 2 kinds) of hetero atoms selected from an oxygen atom, a sulfur atom, a nitrogen atom and the like.

Examples of the "aromatic heterocycle" include 5- to 8-membered (preferably 5- or 6-membered) aromatic monocyclic heterocycle (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like) and the like. Examples of the "non-aromatic heterocycle" include a 5- to 8-membered (preferably 5- or 6-membered) saturated or unsaturated monocyclic non-aromatic heterocycle (aliphatic heterocycle) such as pyrrolidine, tetrahydrofuran, tetrahydrothiophene, thiolane, dithiolane, oxathiolane, pyrroline, imidazolidine, imidazoline, pyrazolidine, pyrazoline, oxazine, oxadiazine, thiazine, thiadiazine, piperidine, morpholine, thiomorpholine, tetrahydropyran, piperazine, pyran, oxepine, thiepine and azepine and the like, or 5- to 8-membered non-aromatic heterocycle formed by saturation of some or all double bonds of the above-described aromatic monocyclic heterocycle, and the like.

In addition, examples of the "heterocyclic group" in the "optionally substituted heterocyclic group" that the "optionally further substituted 6-membered aromatic ring" represented by ring A and ring B as a substituent of, and in the "optionally substituted heterocyclic group" represented by $R^7$ include a group formed by subtracting one hydrogen atom from a condensed ring formed by condensation of two or three (preferably, two) rings selected from the above-described monocyclic heterocycle (monocyclic aromatic heterocycle and monocyclic non-aromatic heterocycle) and 5- to 8-membered cyclic hydrocarbon (5- to 8-membered (preferably 5- or 6-membered) saturated or unsaturated alicyclic hydrocarbon such as $C_{5-8}$cycloalkane, $C_{5-8}$cycloalkene and $C_{5-8}$cycloalkadiene; 6-membered aromatic hydrocarbon such as benzene; and the like), and these condensed rings may be any one of saturated condensed ring, partially unsaturated condensed ring or aromatic condensed ring.

Preferred examples of the condensed ring include a ring formed by condensation of two identical or different heterocycles (preferably, one heterocycle and one aromatic heterocycle, more preferably, two identical or different aromatic heterocycles); a ring formed by condensation of one heterocycle and one homocyclic ring (preferably, one heterocycle and one benzene ring, more preferably, one aromatic heterocycle and one benzene ring); and the like, and specific examples of such condensed ring include indole, benzothiophene, benzofuran, benzimidazole, imidazo[1,2-a]pyridine, quinoline, isoquinoline, cinnoline and the like.

The "heterocyclic group" in the "optionally substituted heterocyclic group" as a substituent of the "optionally further substituted 6-membered aromatic ring" represented by ring A and ring B, and in the "optionally substituted heterocyclic group" represented by $R^7$ may have substituents, and the substituents includes those for the "optionally substituted hydrocarbon group" as a substituent of the "optionally further substituted 6-membered aromatic ring" represented by ring A and ring B.

Examples of the "halogen" as a substituent of the "optionally further substituted 6-membered aromatic ring" represented by ring A and ring B include fluorine, chlorine, bromine, iodine and the like.

Examples of the "optionally substituted amino group" as a substituent of the "optionally further substituted 6-membered aromatic ring" represented by ring A and ring B include those for the "optionally substituted amino group" represented by $R^1$ as described below. Among others, preferred are an amino group optionally having 1 or 2 substituents selected from the "optionally substituted hydrocarbon group" (such as the "optionally substituted hydrocarbon group" as a substituent of the above-described "optionally further substituted 6-membered aromatic ring" represented by ring A and ring B), the "optionally substituted heterocyclic group" (such as the "optionally substituted heterocyclic group" as a substituent of the above-described "optionally further substituted 6-membered aromatic ring" represented by ring A and ring B) and the "optionally substituted acyl group" (such as the "optionally substituted acyl group" as a substituent of the "optionally further substituted 6-membered aromatic ring" represented by ring A and ring B to be described later). More preferred are an amino group optionally having 1 or 2 optionally substituted alkyl [for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$)alkyl and the like optionally having 1 to 3 substituents, respectively, selected from halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole), phenyl-lower ($C_{1-4}$)alkyl, $C_{3-8}$cycloalkyl, an optionally esterified or amidated carboxyl group (for example, carboxyl, $C_{1-4}$alkoxycarbonyl, lower ($C_{7-10}$)aralkyloxy-carbonyl, carbamoyl, mono-$C_{1-4}$alkyl carbamoyl, di-$C_{1-4}$alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), $C_{1-4}$alkylenedioxy (for example, —O—CH$_2$—O—, —O—CH$_2$—CH$_2$—O— and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like) and the like].

In addition, the "optionally substituted amino group" as a substituent of the "optionally further substituted 6-membered aromatic ring" represented by ring A and ring B may form a cyclic amino group by binding of the substituents of the amino to each other (for example, a cyclic amino group formed by subtracting one hydrogen atom from the ring-constituting nitrogen atom of 5- or 6-membered ring such as pyrrolidine, piperazine, piperidine, morpholine, thiomorpholine, pyrrole and imidazole, which has a bond on a nitrogen atom and the like). The cyclic amino group may have a substituent, and examples of the substituent include halogen (for example, fluorine, chlorine, bromine, iodine and the like), nitro, cyano, a hydroxy group, a thiol group, an amino group, a carboxyl group, optionally halogenated $C_{1-4}$alkyl (for example, trifluoromethyl, methyl, ethyl and the like), optionally halogenated $C_{1-4}$alkoxy (for example, methoxy, ethoxy, propoxy, butoxy, trifluoromethoxy, trifluoroethoxy and the like), formyl, $C_{2-4}$alkanoyl (for example, acetyl, propionyl and the like), $C_{1-4}$alkylsulfonyl (for example, methanesulfonyl, ethanesulfonyl and the like) and the like. The number of the substituents is preferably 1 to 3.

Examples of the "optionally substituted acyl group" as a substituent of the "optionally further substituted 6-membered aromatic ring" represented by ring A and ring B include hydrogen, a group formed by binding of the "optionally substituted hydrocarbon group" (such as the "optionally substituted hydrocarbon group" as a substituent of the above-described "optionally further substituted 6-membered aromatic ring" represented by ring A and ring B), the "optionally substituted heterocyclic group" (such as the "optionally substituted heterocyclic group" as a substituent of the above-described "optionally further substituted 6-membered aromatic ring" represented by ring A and ring B) and the like, to a carbonyl group or a sulfonyl group, and the like. The preferred examples include a group formed by binding of (1) hydrogen; (2) optionally substituted alkyl (for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$) alkyl and the like); (3) optionally substituted cycloalkyl (for example, $C_{3-8}$cycloalkyl such as cyclopropyl, cyclobutyl, cyclopentyl, cyclohexyl and cycloheptyl, and the like); (4) optionally substituted alkenyl (for example, $C_{2-10}$alkenyl such as allyl, crotyl, 2-pentenyl and 3-hexenyl, preferably lower ($C_{2-6}$)alkenyl and the like); (5) optionally substituted cycloalkenyl (for example, $C_{3-7}$cycloalkenyl such as 2-cyclopentenyl, 2-cyclohexenyl, 2-cyclopentenylmethyl and 2-cyclohexenylmethyl, and the like); (6) optionally substituted 5- or 6-membered monocyclic aromatic group (for example, phenyl, pyridyl and the like) and the like to a carbonyl group or a sulfonyl group (for example, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl and the like).

Examples of the substituent that the above-described (2) an optionally substituted alkyl, (3) an optionally substituted cycloalkyl, (4) an optionally substituted alkenyl, (5) an optionally substituted cycloalkenyl and (6) an optionally substituted 5- or 6-membered monocyclic aromatic group may have, include halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole), an optionally esterified or amidated carboxyl group (for example, carboxyl, $C_{1-4}$alkoxycarbonyl, carbamoyl, mono-$C_{1-4}$alkyl carbamoyl, di-$C_{1-4}$alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like) and the like. The number of the substituents is preferably 1 to 3.

Examples of the "optionally esterified carboxyl group" as a substituent of the "optionally further substituted 6-membered aromatic ring" represented by ring A and ring B, include a group formed by binding of hydrogen, the "optionally substituted hydrocarbon group" (such as the "optionally substituted hydrocarbon group" as a substituent of the above-described "optionally further substituted 6-membered aromatic ring" represented by ring A and ring B) and the like, to carbonyloxy group, and the like. The preferred examples include a group formed by binding of (1) hydrogen; (2) optionally substituted alkyl (for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$)alkyl and the like); (3) optionally substituted cycloalkyl (for example, $C_{3-8}$cycloalkyl such as cyclopropyl, cyclobutyl, cyclopentyl, cyclohexyl and cycloheptyl, and the like); (4) optionally substituted alkenyl (for example, allyl, crotyl, 2-pentenyl, 3-hexenyl and the like $C_{2-10}$alkenyl, preferably lower ($C_{2-6}$) alkenyl and the like); (5) optionally substituted cycloalkenyl (for example, $C_{3-8}$cycloalkenyl such as 2-cyclopentenyl, 2-cyclohexenyl, 2-cyclopentenylmethyl and 2-cyclohexenylmethyl and the like); (6) optionally substituted aryl (for example, phenyl, naphthyl and the like) and the like, to carbonyloxy group, preferably, carboxyl, lower ($C_{1-6}$)alkoxycarbonyl, aryloxycarbonyl (for example, methoxycarbonyl, ethoxycarbonyl, propoxycarbonyl, phenoxycarbonyl, naphthoxycarbonyl and the like) and the like.

Examples of the substituent that the above-described (2) an optionally substituted alkyl, (3) an optionally substituted cycloalkyl, (4) an optionally substituted alkenyl, (5) an optionally substituted cycloalkenyl and (6) an optionally substituted aryl may have, include halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole), an optionally esterified or amidated carboxyl group (for example, carboxyl, $C_{1-4}$alkoxycarbonyl, carbamoyl, mono-$C_{1-4}$alkyl carbamoyl, di-$C_{1-4}$alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like) and the like. The number of the substituents is preferably 1 to 3.

Examples of the "optionally amidated carboxyl group" as a substituent of the "optionally further substituted 6-membered aromatic ring" represented by ring A and ring B include a group formed by binding of (1) a hydroxy group; (2) an "optionally substituted amino group" (such as the "optionally substituted amino group" as a substituent of the above-described "optionally further substituted 6-membered aromatic ring" represented by ring A and ring B); and the like to, a carbonyl group, and the like.

The substituent of the 6-membered aromatic ring in the "optionally further substituted 6-membered aromatic ring" represented by ring A and ring B may be substituted at one to three (preferably, one to two) any available position of identical or different rings. In addition, when the 6-membered aromatic ring in the "optionally further substituted 6-membered aromatic ring" represented by ring A and ring B have two or more substituents, two of which may bind to each other to form, for example, lower ($C_{1-6}$)alkylene (for example, trimethylene, tetramethylene and the like), lower ($C_{1-6}$)alkyleneoxy (for example, —CH$_2$—O—CH$_2$—, —O—CH$_2$—CH$_2$— and the like), lower ($C_{1-6}$)alkylenedioxy (for example, —O—CH$_2$—O—, —O—CH$_2$—CH$_2$—O— and the like), lower ($C_{2-6}$) alkenylene (for example, —CH$_2$—CH=CH—, —CH$_2$—CH$_2$—CH=CH—, —CH$_2$—CH=CH—CH$_2$— and the like), lower ($C_{4-6}$)alkadienylene (for example, —CH=CH—CH=CH— and the like) and the like.

Examples of the substituents that the "optionally further substituted 6-membered aromatic ring" represented by ring A and ring B may have, include preferably an optionally substituted hydrocarbon group, an optionally substituted heterocyclic group, a nitro group, halogen, an optionally substituted amino group, a group represented by the formula $R^7$-Q- wherein Q is an oxygen atom or an optionally oxidized sulfur atom, and $R^7$ is an optionally substituted hydrocarbon group or an optionally substituted heterocyclic group) and the like, more preferably, an optionally substituted hydrocarbon group, an optionally substituted heterocyclic group, halogen, an optionally substituted amino group, a group represented by the formula $R^7$-Q- wherein Q is an oxygen atom or an optionally oxidized sulfur atom, and $R^7$ is an optionally substituted hydrocarbon group or an optionally substituted heterocyclic group) and the like, and particularly preferably, lower ($C_{1-4}$) alkyl, halogen and the like.

Examples of the 6-membered aromatic ring in the "optionally further substituted 6-membered aromatic ring" represented by ring A and ring B, include preferably a benzene ring and a pyridine ring having no substituents other than the clearly stated substituents, respectively, particularly preferably, a benzene ring having no substituents other than the clearly stated substituents in both of ring A and ring B.

In the above-described the formula (I), examples of the "substituent" in the "optionally substituted amino group" represented by $R^1$ include an amino group optionally having 1 or 2 substituents selected from the "optionally substituted hydrocarbon group" (such as the "optionally substituted hydrocarbon group" as a substituent of the above-described "optionally further substituted 6-membered aromatic ring" represented by ring A and ring B), the "optionally substituted heterocyclic group" (such as the "optionally substituted heterocyclic group" as a substituent of the above-described "optionally further substituted 6-membered aromatic ring" represented by ring A and ring B) and the "optionally substituted acyl group" (such as the "optionally substituted acyl group" as a substituent of the above-described "optionally further substituted 6-membered aromatic ring" represented by ring A and ring B), and the like, the "optionally substituted amino group" represented by $R^1$, may form a cyclic amino group by binding of the substituents of the amino group to each other (for example, a cyclic amino group formed by subtracting one hydrogen atom from the ring-constituting nitrogen atom of 5- or 6-membered ring such as pyrrolidine, piperazine, piperidine, morpholine, thiomorpholine, pyrrole and imidazole, which has a bond on a nitrogen atom and the like). The cyclic amino group may have a substituent, and examples of the substituent include halogen (for example, fluorine, chlorine, bromine, iodine and the like), nitro, cyano, a hydroxy group, a thiol group, an amino group, a carboxyl group, optionally halogenated $C_{1-4}$alkyl (for example, trifluoromethyl, methyl, ethyl and the like), optionally halogenated $C_{1-4}$alkoxy (for example, methoxy, ethoxy, propoxy, butoxy, trifluoromethoxy, trifluoroethoxy and the like), formyl, $C_{2-4}$alkanoyl (for example, acetyl, propionyl and the like), $C_{1-4}$alkylsulfonyl (for example, methanesulfonyl, ethanesulfonyl and the like) and the like. The number of substituents is preferably 1 to 3.

Examples of the substituent of the amino group in the "optionally substituted amino group" represented by $R^1$, include preferably (1) optionally substituted alkyl (for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$)alkyl and the like); (2) optionally substituted cycloalkyl (for example, $C_{3-8}$cycloalkyl such as cyclopropyl, cyclobutyl, cyclopentyl, cyclohexyl, cycloheptyl, cyclooctyl, and the like); the cycloalkyl may be condensed with a benzene ring to form indane (for example, indan-1-yl, indan-2-yl and the like), tetrahydronaphthalene (for example, tetrahydronaphthalen-5-yl, tetrahydronaphthalen-6-yl and the like) and the like (preferably, indane and the like); the cycloalkyl may be cross-linked through a straight chain having 1 or 2 carbon atoms to form a cross-linked cyclic hydrocarbon residue such as bicyclo[2.2.1]heptyl, bicyclo[2.2.2]octyl, bicyclo[3.2.1]octyl, bicyclo[3.2.2]nonyl and the like (preferably, cyclohexyl having a link of a straight chain having 1 or 2 carbon atoms and the like, more preferably, bicyclo[2.2.1heptyl and the like); (3) optionally substituted alkenyl (for example, allyl, crotyl, 2-pentenyl, 3-hexenyl and the like $C_{2-10}$alkenyl, preferably lower ($C_{2-6}$)alkenyl and the like); (4) optionally substituted cycloalkenyl (for example, $C_{3-7}$cycloalkenyl such as 2-cyclopentenyl, 2-cyclohexenyl, 2-cyclopentenylmethyl and 2-cyclohexenylmethyl, and the like); (5) an optionally substituted aralkyl (for example, phenyl-$C_{1-4}$alkyl (for example, benzyl, phenethyl and the like) and the like); (6) formyl or optionally substituted acyl (for example, $C_{2-4}$alkanoyl (for example, acetyl, propionyl, butyryl, isobutyryl and the like), $C_{1-4}$alkylsulfonyl (for example, methanesulfonyl, ethanesulfonyl and the like) and the like); (7) an optionally substituted aryl (for example, phenyl, naphthyl and the like); (8) an optionally substituted heterocyclic group (for example, a group formed by subtracting one hydrogen atom from 5- or 6-membered aromatic heterocycle containing one to four hetero atoms of 1 or 2 kinds selected from a nitrogen atom, a sulfur atom, an oxygen atom and the like such as furan, thiophene, pyrrole, imidazole, pyrazole, thiazole, oxazole, isothiazole, isoquinazole, tetrazole, pyridine, pyrazine, pyrimidine, pyridazine and triazole, a group formed by subtracting one hydrogen atom from 5- or 6-membered non-aromatic heterocycle containing one to four hetero atoms of 1 or 2 kinds selected from a nitrogen atom, a sulfur atom, an oxygen atom and the like such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran and tetrahydropyran, and the like.

Examples of the substituent that the above-described (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl, (7) optionally substituted aryl and (8) optionally substituted heterocyclic group may have, include halogen (for example, fluorine, chlorine, bromine, iodine and the like), $C_{1-4}$alkyl optionally substituted with halogen or $C_{1-4}$alkoxy, $C_{1-4}$alkoxy optionally substituted with halogen or $C_{1-4}$alkoxy (for example, methoxy, ethoxy, propoxy, butoxy, trifluoromethoxy, trifluoroethoxy and the like), $C_{1-4}$alkylenedioxy (for example, —O—CH$_2$—O—, —O—CH$_2$—CH$_2$—O— and the like), formyl, $C_{2-4}$alkanoyl (for example, acetyl, propionyl and the like), $C_{1-4}$alkylsulfonyl (for example, methanesulfonyl, ethanesulfonyl and the like), phenyl-lower ($C_{1-4}$)alkyl, $C_{3-8}$cycloalkyl, cyano, nitro, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole), a carboxyl group, lower ($C_{1-4}$)alkoxy-carbonyl, $C_{7-10}$ aralkyloxy-carbonyl, carbamoyl, mono-$C_{1-4}$alkyl carbamoyl, di-$C_{1-4}$alkyl carbamoyl (preferably, halogen, optionally halogenated lower ($C_{1-4}$) alkyl, optionally halogenated lower ($C_{1-4}$)alkoxy, phenyl-lower ($C_{1-4}$)alkyl, $C_{3-8}$cycloalkyl, cyano, a hydroxy group and the like) and the like. The number of the substituents is preferably 1 to 3.

Particularly preferred examples of the "optionally substituted amino group" represented by $R^1$, include an amino group optionally having 1 or 2 optionally substituted alkyls [for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$)alkyl and the like optionally having one to three substituents independently selected from halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole, and the like), an optionally esterified or amidated carboxyl group (for example, carboxyl, $C_{1-4}$alkoxycarbonyl, $C_{7-10}$aralkyloxycarbonyl, carbamoyl, mono-$C_{1-4}$alkyl carbamoyl, di-$C_{1-4}$ alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), $C_{1-4}$alkylenedioxy (for example, —O—CH$_2$—O—, —O—CH$_2$—CH$_2$—O— and the like), phenyl-lower ($C_{1-4}$) alkyl, $C_{3-8}$cycloalkyl, formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like), and the like].

Other preferred examples of the "optionally substituted amino group" in the definitions $R^1$ include an amino group optionally having $C_{1-10}$alkylcarbonyl optionally substituted with an amino group as a substituent.

In the above formula, examples of the "heterocyclic group" of the "optionally substituted heterocyclic group" in the definitions $R^1$ include a group formed by subtracting one hydrogen atom from a ring made by condensation of identical or different two or three rings selected from 5- to 8-membered aromatic monocyclic heterocycle, saturated or unsaturated non-aromatic monocyclic heterocycle (aliphatic heterocycle) and the like optionally containing one to four (preferably one to two) hetero atoms of 1 or 3 kinds (preferably, 1 or 2 kinds) selected from a nitrogen atom, a sulfur atom, an oxygen atom and the like; a monocycles thereof, and the like. In addition, the "optionally substituted heterocyclic group" represented by $R^1$ may bind to Y through any one of a nitrogen atom or a carbon atom, preferably through a nitrogen atom.

Examples of the "aromatic monocyclic heterocycle" include 5- to 8-membered (preferably 5- or 6-membered) aromatic monocyclic heterocycle (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like) and the like. Herein, examples of the "non-aromatic monocyclic heterocycle" include 5- to 8-membered (preferably 5- or 6-membered) saturated or unsaturated monocyclic non-aromatic heterocycle (aliphatic heterocycle) such as tetrahydrofuran, tetrahydrothiophene, pyrrolidine, pyrroline, imidazolidine, imidazoline, pyrazolidine, pyrazoline, oxazine, oxadiazine, thiazine, thiadiazine, piperidine, morpholine, thiomorpholine, piperazine and azepine, and the like, or 5- to 8-membered non-aromatic heterocycle formed by saturation of some or all of the double bonds in the above-described aromatic monocyclic heterocycle, and the like.

Examples of the substituent of the "heterocyclic group" as a substituent of the "optionally substituted heterocyclic group" represented by $R^1$, include such group as the substituent of the "optionally substituted hydrocarbon group" which is a substituent of the above-described "optionally further substituted 6-membered aromatic ring" represented by ring A and ring B.

Examples of the "heterocyclic group" of the "optionally substituted heterocyclic group" represented by $R^1$ include preferably 5- or 6-membered nitrogen-containing heterocyclic group, more preferably saturated 5- or 6-membered nitrogen-containing heterocyclic group, and preferably among others, pyrrolidine, piperidine, piperazine (preferably, saturated 5- or 6-membered nitrogen-containing heterocyclic group containing one nitrogen atom) and the like.

Particularly, $R^1$ is preferably (1) an amino group optionally mono- or di-substituted with (1') $C_{1-10}$alkyl optionally substituted with carbamoyl or (2') $C_{1-10}$alkylcarbonyl optionally substituted with amino, (2) a cyclic amino group such as pyrrolidine, piperidine and piperazine (preferably, saturated 5- or 6-membered cyclic amino group containing one a nitrogen atom), and the like. Among others, $R^1$ is preferably an amino group optionally mono- or di-substituted with $C_{1-10}$alkyl (for example, amino, methylamino, ethylamino, dimethylamino, diethylamino and the like), a cyclic amino group such as pyrrolidine, piperidine and piperazine (preferably, saturated 5- or 6-membered cyclic amino group containing one nitrogen atom) and the like. Especially, $R^1$ is an amino group having no substituent.

In the above the formula (I), examples of the "hydrocarbon group" of the "optionally substituted hydrocarbon group" represented by $R^2$, $R^3$, $R^4$, $R^5$ and $R^6$ include (1) alkyl (for example, $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl and decyl, preferably lower ($C_{1-6}$)alkyl and the like); (2) cycloalkyl (for example, $C_{3-8}$cycloalkyl such as cyclopropyl, cyclobutyl, cyclopentyl, cyclohexyl and cycloheptyl, and the like); in addition, the cycloalkyl may be condensed with a benzene ring to form indane (for example, indan-1-yl, indan-2-yl and the like), tetrahydronaphthalene (for example, tetrahydronaphthalen-5-yl, tetrahydronaphthalen-6-yl and the like) and the like (preferably, indane and the like); in addition, the cycloalkyl may be cross-linked through a straight chain having 1 or 2 carbon atoms to form a cross-linked cyclic hydrocarbon residue such as bicyclo[2.2.1]heptyl, bicyclo[2.2.2]octyl, bicyclo[3.2.1]octyl, bicyclo[3.2.2]nonyl and the like (preferably, cyclohexyl having a link of a straight chain having 1 or 2 carbon atoms and the like, more preferably, bicyclo[2.2.1]heptyl and the like); (3) alkenyl (for example, $C_{2-10}$alkenyl such as vinyl, allyl, crotyl, 2-pentenyl and 3-hexenyl, preferably lower ($C_{2-6}$)alkenyl and the like); (4) cycloalkenyl (for example, $C_{3-8}$cycloalkenyl such as 2-cyclopentenyl, 2-cyclohexenyl, 2-cyclopentenylmethyl and 2-cyclohexenylmethyl, and the like); (5) alkynyl (for example, $C_{2-10}$alkynyl such as ethynyl, 1-propynyl, 2-propynyl, 1-butynyl, 2-pentynyl and 3-hexynyl, preferably lower ($C_{2-6}$)alkynyl and the like); (6) cycloalkyl-alkyl (for example, $C_{3-8}$cycloalkyl-$C_{1-6}$alkyl), preferably cyclopentyl-$C_{1-4}$alkyl, cyclohexyl-$C_{1-4}$alkyl (for example, cyclopentylmethyl, cyclohexylmethyl and the like) and the like); (7) aryl (for example, $C_{6-14}$aryl such as phenyl and naphthyl, preferably $C_{1-10}$aryl, more preferably phenyl and the like); (8) aralkyl (for example, $C_{1-6}$alkyl having 1 to 3 $C_{6-14}$aryl, preferably, phenyl-$C_{1-4}$alkyl (for example, benzyl, phenethyl and the like) and the like); (9) a group represented by the formula —X'''-G-(CH$_2$)$_n$-J wherein X''' is a $C_{1-4}$alkylene group or a $C_{2-4}$alkenylene group, G is a bond, —O—, —S—, —CO—NH— or —NH—CO—, n is an integer of 0 to 3, and J is an optionally substituted aromatic ring group; or (10) a group represented by the formula —X''''-L-(CH$_2$)$_n$-M wherein X'''' is a bond or $C_{1-4}$alkylene group, L is (a) a bond, (b) an optionally substituted aromatic ring group, (c) —O—, (d) —S—, (e) —CO—NH— or (f) —NH—CO—, n is an integer of 0 to 3, and M is an amino group, a guanidino group, a sulfamoyl group, a carbamoyl group or a hydroxy group (provided that when X'''' and L are a bond, n is not 0)]; and the like.

In the above formula, examples of the optionally substituted aromatic ring group represented by J and L include optionally substituted aryl group, optionally substituted aromatic heterocyclic group and the like.

Examples of the "aryl group" in the "optionally substituted aryl group" represented by J and L, include $C_{6-14}$aryl such as phenyl and naphthyl, preferably $C_{6-10}$aryl, more preferably phenyl and the like.

Examples of the "aromatic heterocyclic group" in the "optionally substituted aromatic heterocyclic group" represented by J and L include those for the "optionally substituted aromatic heterocyclic group" in the "optionally substituted heterocyclic group" represented by $R^7$, and preferably among others, optionally substituted 5- or 6-membered aromatic monocyclic heterocyclic group. Examples of the 5- or 6-membered aromatic monocyclic heterocyclic group include furan, thiophene, pyrrole, oxazole, isoxazole, thiazole, isothiazole, imidazole, pyrazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like.

Examples of the substituent in the "optionally substituted aromatic ring group" represented by J and L include halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole, imidazole, 2-oxo-1-pyrrolidinyl and 2-oxo-1-piperidinyl, and the like), phenyl-lower ($C_{1-4}$)alkyl, $C_{3-8}$cycloalkyl, an optionally esterified or amidated carboxyl group (for example, carboxyl, $C_{1-4}$alkoxy-carbonyl, lower ($C_{7-10}$)aralkyloxy-carbonyl, carbamoyl, mono-$C_{1-4}$alkyl carbamoyl, di-$C_{1-4}$alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), $C_{1-4}$alkylenedioxy (for example, —O—CH$_2$—O—, —O—CH$_2$—CH$_2$—O— and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like), an optionally substituted sulfamoyl group (for example, sulfamoyl, mono-$C_{1-4}$alkylsulfamoyl, di-$C_{1-4}$alkylsulfamoyl and the like), an optionally substituted aryl group, an optionally substituted heterocyclic group and the like. The number of substituents is preferably 1 to 3.

Examples of the substituent in the "optionally substituted hydrocarbon group" represented by $R^2$, $R^3$, $R^4$, $R^5$ and $R^6$ include halogen (for example, fluorine, chlorine, bromine, iodine and the like), nitro, cyano, oxo (provided that it may not join the hydrocarbon group to form an acyl group), a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole, imidazole, 2-oxo-1-pyrrolidinyl and 2-oxo-1-piperidinyl and the like), phenyl-lower ($C_{1-4}$)alkyl, $C_{3-8}$cycloalkyl, an optionally esterified or amidated carboxyl group (for example, carboxyl, $C_{1-4}$alkoxy-carbonyl, $C_{7-10}$aralkyloxy-carbonyl, carbamoyl, mono-$C_{1-4}$alkyl carbamoyl, di-$C_{1-4}$alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), $C_{1-4}$alkylenedioxy (for example, —O—CH$_2$—O—, —O—CH$_2$—CH$_2$—O— and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like), an optionally substituted sulfamoyl group (for example, sulfamoyl, mono-$C_{1-4}$alkylsulfamoyl, di-$C_{1-4}$alkylsulfamoyl and the like), an optionally substituted aryl group, an optionally substituted heterocyclic group and the like. The number of substituents is preferably 1 to 3.

Examples of the "aryl group" in the "optionally substituted aryl group" as a substituent of the "optionally substituted hydrocarbon group" represented by $R^2$, $R^3$, $R^4$, $R^5$ and $R^6$ include $C_{6-14}$aryl such as phenyl and naphthyl, preferably $C_{6-10}$aryl, more preferably phenyl and the like.

Examples of the substituent that the "aryl group" may have, include halogen (for example, fluorine, chlorine, bromine, iodine and the like), nitro, cyano, a hydroxy group, an optionally substituted thiol group (for example, thiol, $C_{1-4}$alkylthio and the like), an optionally substituted amino group (for example, amino, mono-$C_{1-4}$alkylamino, di-$C_{1-4}$alkylamino, 5- or 6-membered cyclic amino such as pyrrolidine, piperazine, piperidine, morpholine, thiomorpholine, pyrrole and imidazole), phenyl-lower ($C_{1-4}$)alkyl, $C_{3-8}$cycloalkyl, an optionally esterified or amidated carboxyl group (for example, carboxyl, $C_{1-4}$alkoxy-carbonyl, $C_{7-10}$ aralkyloxycarbonyl, carbamoyl, mono-$C_{1-4}$alkyl carbamoyl, di-$C_{1-4}$ alkyl carbamoyl and the like), $C_{1-4}$alkyl optionally substituted with halogen or $C_{1-4}$alkoxy (for example, trifluoromethyl, methyl, ethyl and the like), $C_{1-4}$alkoxy optionally substituted with halogen or $C_{1-4}$alkoxy (for example, methoxy, ethoxy, trifluoromethoxy, trifluoroethoxy and the like), $C_{1-4}$alkylenedioxy (for example, —O—CH$_2$—O—, —O—CH$_2$—CH$_2$—O— and the like), formyl, $C_{2-4}$alkanoyl (for example, acetyl, propionyl and the like), $C_{1-4}$alkylsulfonyl (for example, methanesulfonyl, ethanesulfonyl and the like), $C_{1-4}$alkylsulfinyl (for example, methanesulfinyl, ethanesulfinyl and the like), an optionally substituted sulfamoyl group (for example, sulfamoyl, mono-$C_{1-4}$alkylsulfamoyl, di-$C_{1-4}$alkylsulfamoyl and the like), 5- or 6-membered aromatic monocyclic heterocycle (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like) and the like. The number of substituents is preferably 1 to 3.

Examples of the "optionally substituted heterocyclic group" as a substituent of the "optionally substituted hydrocarbon group" represented by $R^2$, $R^3$, $R^4$, $R^5$ and $R^6$ include those for the "optionally substituted heterocyclic group" represented by $R^7$, and the like.

Examples of the "optionally substituted heterocyclic group" represented by $R^2$, $R^3$, $R^4$, $R^5$ and $R^6$ include those for the "optionally substituted heterocyclic group" represented by $R^1$.

$R^2$ is preferably an optionally substituted $C_{1-10}$alkyl, optionally substituted $C_{3-8}$cycloalkyl-$C_{1-6}$alkyl, optionally substituted $C_{6-14}$aryl and optionally substituted $C_{6-14}$aryl-$C_{1-6}$alkyl.

Among others, $R^2$ is preferably (1) $C_{1-10}$alkyl that may have 5- or 6-membered aromatic heterocycle (for example, a pyridine ring) as a substituent, (2) $C_{3-8}$cycloalkyl-$C_{1-6}$alkyl that may have $C_{1-4}$alkyl as a substituent, (3) $C_{6-14}$aryl, (4) $C_{6-14}$aryl-$C_{1-6}$alkyl that may have halogen, optionally halogenated $C_{1-4}$alkyl or $C_{1-4}$alkoxy as a substituent and (5) $C_{1-10}$alkyl that has $C_{6-14}$aryloxy as a substituent, and the like.

Particularly, $R^2$ is (1) $C_{1-10}$alkyl (especially, $C_{1-6}$alkyl) that may have a pyridine ring as a substituent (for example, 2-pyridylmethyl, 2-pyridylethyl, 3-pyridylmethyl, 3-pyridylethyl and the like), (2) $C_{3-8}$cycloalkyl-$C_{1-6}$alkyl that has methyl as a substituent (for example, 2-methyl cyclopentylmethyl, 3-methyl cyclopentylmethyl, 2-cyclohexylmethyl, 3-cyclohexylmethyl, 4-cyclohexylmethyl and the like), (3) phenyl, (4) $C_{6-14}$aryl-$C_{1-6}$alkyl that may have halogen, trifluoromethyl or methoxy as a substituent (for example, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 1-naphthylmethyl, 2-naphthylmethyl and the like) and (5) phenoxymethyl and the like. Especially, $R^2$ is preferably 3-chlorobenzyl, 4-chlorobenzyl, 4-bromobenzyl, 2-naphthylmethyl and the like.

$R^3$ is preferably an optionally substituted 5- to 8-membered non-aromatic heterocyclic group (especially, 6-membered non-aromatic heterocyclic group).

Among others, $R^3$ is preferably 5- or 6-membered non-aromatic nitrogen-containing heterocyclic group (for example, pyrrolidinyl, piperidinyl, piperazinyl and the like, especially, pyrrolidinyl, piperidinyl) as a substituent of phenyl-$C_{1-4}$alkyl, mono-$C_{1-6}$alkyl carbamoyl, $C_{3-8}$cycloalkyl carbamoyl, mono-$C_{6-14}$aryl carbamoyl, heterocyclic carbamoyl, $C_{1-4}$alkyl optionally substituted with $C_{3-8}$cycloalkyl, $C_{2-4}$alkanoyl, $C_{3-8}$cycloalkylcarbonyl, $C_{6-14}$arylcarbonyl optionally substituted with a hydroxy group, and aromatic nitrogen-containing or aromatic oxygen-containing heterocyclic carbonyl and the like.

Particularly, $R^3$ is preferably pyrrolidinyl, 1-benzylpyrrolidinyl, 1-cyclohexylmethyl pyrrolidinyl, piperidinyl, 1-benzylpiperidinyl, 1-cyclohexylmethyl piperidinyl, 1-phenethylpiperidinyl, 1-benzoylpiperidinyl, 1-cyclohexanecarbonylpiperidinyl, 1-cyclohexanecarbamoylpiperidinyl, 1-phenylcarbamoylpiperidinyl, piperazinyl, 4-benzylpiperazinyl, 4-phenethylpiperazinyl, 4-phenylcarbamoylpiperazinyl, 1-(2-hydroxybenzoyl)piperidinyl, 1-(3-hydroxybenzoyl)piperidinyl, 1-(4-hydroxybenzoyl)piperidinyl and the like.

$R^5$ is preferably optionally substituted $C_{1-10}$alkyl. Among others, $R^5$ is preferably $C_{1-4}$alkyl, especially methyl.

In the above-described formula (I), X is —CONR$^4$—, —SO$_2$NR$^4$—, —CH$_2$NR$^4$—, —NR$^4$CO—, —NR$^4$SO$_2$—, —NR$^4$—CO—NH—, —O—, —S—, —SO—, —SO$_2$—, —CO—, —CO$_2$—, —CH=CH— or a bond (R$^4$ are the same as defined above), preferably, a bond, —CONR$^4$—, —SO$_2$NR$^4$—, —NR$^4$CO—, —O— and —CO$_2$— (R$^4$ are the same as defined above), more preferably, a bond, —CONR$^4$—, —NR$^4$CO— and —CO$_2$— (R$^4$ is a hydrogen atom or optionally substituted $C_{1-6}$alkyl, preferably a hydrogen atom), and most preferably, —CONH—, —NHCO— and —CO$_2$—.

In addition, a "ring" when X and Y in the above formula (I) join together to form a ring, may be saturated or unsaturated nitrogen-containing heterocycle of any ring size. Among others, the ring is preferably 3 to 8-membered nitrogen-containing heterocycle, and more preferably, saturated 3 to 8-membered nitrogen-containing heterocycle, i.e., a ring represented by the formula:

wherein ring D is a saturated 3 to 8-membered nitrogen-containing heterocycle.

Examples of the "3 to 8-membered nitrogen-containing heterocycle" include 3 to 8-membered nitrogen-containing heterocycle containing one nitrogen atom and further one to four (preferably one to two) hetero atoms consisting of 1 or 3 kinds (preferably, 1 or 2 kinds) hetero atoms selected from a nitrogen atom, a sulfur atom, an oxygen atom and the like, more specifically, 3 to 8-membered (preferably 5- or 6-membered) saturated or unsaturated (preferably saturated) monocyclic non-aromatic heterocycle (aliphatic heterocycle) such as pyrrolidine, pyrroline, imidazolidine, imidazoline, pyrazolidine, pyrazoline, oxazine, oxadiazine, thiazine, thiadiazine, piperidine, morpholine, thiomorpholine, piperazine and azepine, and the like.

In addition, the "3 to 8-membered nitrogen-containing heterocycle" may have a substituent, and examples of the substituent include such groups as the substituents of the "optionally substituted hydrocarbon group" which is a substituent of the optionally further substituted 6-membered aromatic ring" represented by the ring A and ring B.

In addition, X in the above formula (I) may bind to "optionally substituted amino group" represented by $R^1$ to form a ring, and this "ring" may be saturated or unsaturated heterocycle containing at least two nitrogen atoms of any ring size. Among others, the ring is preferably a 3 to 8-membered nitrogen-containing heterocycle, and more preferably, a saturated 3 to 8-membered nitrogen-containing heterocycle, i.e., a ring represented by the formula:

wherein $R^{1'}$ is an optionally substituted hydrocarbon group, and ring E is a saturated 3 to 8-membered nitrogen-containing heterocycle.

In the above formula, examples of the "optionally substituted hydrocarbon" represented by the $R^{1'}$ include those for the "optionally substituted hydrocarbon group" as the substituent of the "amino group" in the "optionally substituted amino group" represented by $R^1$.

Examples of the "3 to 8-membered nitrogen-containing heterocycle" include 3 to 8-membered nitrogen-containing heterocycle containing two nitrogen atoms and further one to four (preferably one to two) hetero atoms consisting of 1 or 3 kinds (preferably, 1 or 2 kinds) hetero atoms selected from a nitrogen atom, a sulfur atom, an oxygen atom and the like, more specifically, 3 to 8-membered (preferably 5- or 6-membered) saturated or unsaturated (preferably saturated) monocyclic non-aromatic heterocycle (aliphatic heterocycle) such as imidazolidine, imidazoline, pyrazolidine, pyrazoline, oxadiazine, thiadiazine, piperazine and diazepine, and the like.

In addition, the "3 to 8-membered nitrogen-containing heterocycle" may have a substituent, and examples of the substituent include such groups as the substituents in the "optionally further substituted 6-membered aromatic ring" represented by ring A and ring B.

When X, Y and $R^1$ join together to form a ring, it is preferable that X binds to the "optionally substituted amino group" represented by $R^1$ to form a 3 to 8-membered nitrogen-containing heterocycle, preferably, a 3 to 8-membered saturated nitrogen-containing heterocycle, and more preferably, piperazine ring. Specifically, it is preferable that X, Y and $R^1$ join together to form a piperazinyl-carbonyl group.

In the above formula, examples of the "spacer having 1 to 12 atoms, which constitutes a straight chain moiety" represented by Y may be any one which is a "divalent group having the straight chain moiety of 1 to 12 atoms", for example, a saturated divalent group of (1) —$(CH_2)_{f1}$— (f1 is an integer of 1 to 12, preferably 1 to 8, more preferably 1 to 6, particularly preferably 1 to 4), (2) —$(CH_2)_{g1}$—$Y^1$—$(CH_2)_{g2}$— (g1 and g2 are the same or different and an integer of 0 to 11, provided that the sum of g1 and g2 is between 0 to 11. $Y^1$ is NH, O, S, SO or $SO_2$) or (3) —$(CH_2)_{h1}$—$Y^1$—$(CH_2)_{h2}$—$Y^2$—$(CH_2)_{h3}$— (h1, h2 and h3 are the same or different and an integer of 0 to 10, provided that the sum of h1, h2 and h3 is between 0 to 10. $Y^1$ and $Y^2$ are independently NH, O, S, SO or $SO_2$, provided that when h2 is O, at least one of $Y^1$ and $Y^2$ is preferably NH.) and the like, and divalent group thereof wherein some bonds of the divalent group are converted to unsaturated bonds. Specific examples of the divalent group include —O—$(CH_2)_{k3}$— (k3 is an integer of 0 to 11), —$(CH_2)_{k3}$—O— (k3 is an integer of 0 to 11), —S—$(CH_2)_{k3}$— (k3 is an integer of 0 to 11), —$(CH_2)_{k3}$—S— (k3 is an integer of 0 to 11), —NH—$(CH_2)_{k3}$— (k3 is an integer of 0 to 11), —$(CH_2)_{k3}$—NH— (k3 is an integer of 0 to 11), —$(CH_2)_{k4}$— (k4 is an integer of 1 to 12), —CH=CH—, —C≡C—, —CO—NH—, —$SO_2$—NH— and the like.

Y is more preferably a divalent group in which carbon atom number constituting the straight chain moiety is 1 to 4, among others, $C_{1-4}$alkylene, $C_{2-4}$alkenylene, and the like, and particularly, $C_{1-4}$alkylene.

The divalent group as Y may have substituents on any available position (preferably on carbon atom), and the substituents may be any one which can bind to a divalent chain constituting a straight chain moiety, and examples of the substituents include such groups as the substituents of the above-described "optionally further substituted 6-membered aromatic ring" represented by ring A and ring B, and an oxo group and the like. The substituents are in the number of 1 to 4 (preferably, 1 or 2), the same or different, and may be substituted at any position of the divalent group. In addition, the substituents of the divalent group as Y may bind to each other to form a ring, and the examples of the "ring" include $C_{5-7}$cycloalkane such as cyclopentane, cyclohexane and cycloheptane; benzene and the like.

Preferred examples of the substituents of the divalent group as Y include lower ($C_{1-6}$)alkyl (for example, methyl, ethyl, propyl, isopropyl, butyl, isobutyl, sec-butyl, tert-butyl, pentyl, isopentyl, neopentyl, hexyl and the like), lower ($C_{3-7}$)cycloalkyl (for example, cyclopropyl, cyclobutyl, cyclopentyl, cyclohexyl, cycloheptyl and the like), formyl, lower ($C_{2-7}$)alkanoyl (for example, acetyl, propionyl, butyryl and the like), lower ($C_{1-6}$)alkoxy-carbonyl, lower ($C_{1-6}$) alkoxy, a hydroxy group, oxo and the like.

Y is preferably $C_{2-4}$alkylene optionally substituted with $C_{1-6}$alkyl.

In the above formula, Z is, for example, —$CONR^6$—, —$CSNR^6$—, —CO— or —$SO_2$— ($R^6$ is the same as defined above), and among others, preferably —$CONR^6$—, —CO— or —$SO_2$— ($R^6$ is the same as defined above), and more preferably, —CO—.

In the above-described formula (I), ring A and ring B preferably may form a benzene ring together, and the clearly stated substituents may be substituted at any available position. The compound represented by the formula (I) or a salt thereof preferably has any of the following structures.

Formulas:

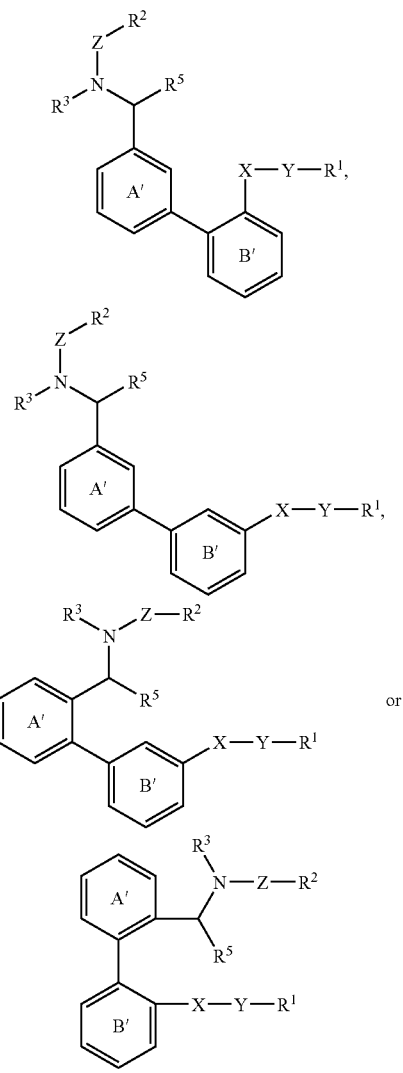

wherein ring A' and ring B' are optionally further substituted benzene rings, and the other symbols are the same as defined above.

Among others, the compound having the following structural formula:

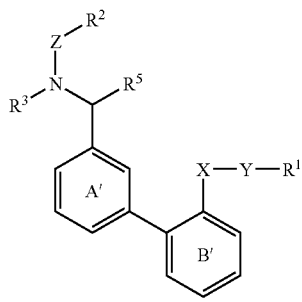

wherein ring A' and ring B' are optionally further substituted benzene rings, and the other symbols are the same as defined above; is preferable.

Particularly preferred examples of the compound represented by the formula (I) include, N-(2-aminoethyl)-3'-[1-{N-(1-benzylpiperidin-4-yl)-N-(2-naphthylacetyl)amino}ethyl][1,1'-biphenyl]-2-carboxamide, N-(2-aminoethyl)-3'-[1-{N-(1-benzylpiperidin-4-yl)-N-(4-chlorophenylacetyl)amino}ethyl][1,1'-biphenyl]-2-carboxamide, N-(2-aminoethyl)-3'-[1-{N-(1-benzylpiperidin-4-yl)-N-(3-chlorophenylacetyl)amino}ethyl][1,1'-biphenyl]-2-carboxamide, N-(2-aminoethyl)-3'-[1-{N-(1-benzylpiperidin-4-yl)-N-(4-bromophenylacetyl)amino}ethyl][1,1'-biphenyl]-2-carboxamide, N-(2-aminoethyl)-3'-[1-{N-(1-benzylpiperidin-4-yl)-N-(3,4-dichlorophenylacetyl)amino}ethyl][1,1'-biphenyl]-2-carboxamide, N-(2-aminoethyl)-3'-[1-{N-(4-chlorophenylacetyl)-N-(1-(2-indolecarbonyl)piperidin-4-yl)amino}ethyl][1,1'-biphenyl]-2-carboxamide, N-(2-aminoethyl)-3'-[1-{(N-(1-(2-benzofurancarbonyl)piperidin-4-yl)-N-(4-chlorophenylacetyl)amino}ethyl][1,1'-biphenyl]-2-carboxamide, N-(2-aminoethyl)-3'-[1-{N-(4-chlorophenylacetyl)-N-(1-(4-hydroxybenzoyl)piperidin-4-yl)amino}ethyl][1,1'-biphenyl]-2-carboxamide or salts thereof and the like.

In addition, a compound represented by the formula:

$$\text{(I')}$$

wherein ring A and ring B are optionally further substituted 6-membered aromatic rings, X is —CONR$^4$—, —SO$_2$NR$^4$—, —CH$_2$NR$^4$—, —NR$^4$CO—, —NR$^4$ SO$_2$—, —NR$^4$—CO—NH—, —O—, —S—, —SO—, —SO$_2$—, —CO—, —CO$_2$—, —CH=CH— or a bond (R$^4$ is a hydrogen atom, an optionally substituted hydrocarbon group or an optionally substituted heterocyclic group), Y is a spacer having 1 to 12 atoms or a bond, Z is —CONR$^6$—, —CSNR$^6$—, —CO— or —SO$_2$— (R$^6$ is a hydrogen atom, an optionally substituted hydrocarbon group or an optionally substituted heterocyclic group), R$^1$ is an optionally substituted amino group or an optionally substituted heterocyclic group, R$^2$ is a hydrogen atom, an optionally substituted hydrocarbon group or an optionally substituted heterocyclic group, R$^3$ is a hydrogen atom, an optionally substituted hydrocarbon group or an optionally substituted heterocyclic group, R$^{5'}$ is a hydrogen atom, an optionally substituted hydrocarbon group or an optionally substituted heterocyclic group (X and Y or X, Y and R$^1$ may form a ring together)] or a salt thereof, which contains known compounds, is a compound acting on melanocortin receptor (MC-R).

In the formula (I'), ring A, ring B, X, Y, Z, R$^1$, R$^2$, R$^3$, R$^4$ and R$^6$ are the same as defined above.

In the formula (I'), examples of the "optionally substituted hydrocarbon group" represented by R$^{5'}$ include those for the "optionally substituted hydrocarbon group" represented by R$^2$, R$^3$ and R$^4$.

Examples of a salt of the compound represented by the formula (I) or the formula (I') include preferably a pharmaceutically acceptable salt such as a salt with inorganic base, a salt with organic base, a salt with inorganic acid, a salt with organic acid, a salt with basic or acidic amino acid, etc.

Suitable examples of a salt with an inorganic base include the salt with alkali metal (e.g. sodium, potassium, etc.), alkaline earth metal (e.g. calcium, magnesium, etc.), aluminum, ammonium, etc.

Suitable examples of a salt with an organic base include a salt with trimethylamine, triethylamine, pyridine, picoline, ethanolamine, diethanolamine, triethanolamine, dicyclohexylamine, N,N'-dibenzylethylenediamine, etc.

Suitable examples of a salt with an inorganic acid include a salt with hydrochloric acid, hydrobromic acid, nitric acid, sulfuric acid, phosphoric acid, etc.

Suitable examples of a salt with an organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Suitable examples of a salt with a basic amino acid include a salt with arginine, lysine, ornithine, etc., and suitable examples of the salt with the acidic amino acid include a salt with aspartic acid, glutamic acid, etc.

The compound of the formula (I) or the formula (I') of the present invention may be hydrated or non-hydrated. When the compound of the formula (I) or the formula (I') of the present invention exists as configuration isomer, diastereomer, conformer, etc., it is possible to isolate individual isomers with a per se known separation and purification method, if desired. When the compound of the formula (I) or the formula (I') of the present invention is racemate, it can be separated into (S)-isomer and (R)-isomer with usual optical resolution and any of individual optically active substances and racemates thereof are included in the scope of the present invention.

The compound of the formula (I) or the formula (I') or a salt thereof [hereinafter, referred to as the compound of the present invention in some cases) of the present invention may be used in the form of a prodrug. The prodrug of the compound of the formula (I) or the formula (I') or a salt thereof of the present invention refers to a compound which is converted to the compound of the present invention by a reaction with an enzyme, an gastric acid, etc. under physiological conditions in the living body, that is, a compound which is converted to the compound of the present invention by enzymatic oxidation, reduction, hydrolysis, etc.; a compound which is converted to the present compound with hydrolysis by gastric acid, etc.;, etc. Examples of a prodrug of the compound of the present invention include a compound wherein an amino group of the compound of the present invention is substituted with acyl, alkyl, phosphoric acid, etc. (e.g., a compound wherein an amino group of the present compound is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc,); a compound wherein a hydroxy group of the compound of the present invention is substituted with acyl, alkyl, phosphoric acid, boric acid, etc. (e.g. a compound wherein an hydroxy group of the compound of the present invention is modified with acetyl, palmitoyl, propanoyl, pivaloyl, succinyl, fumaryl, alanyl, dimethylaminomethylcarbonyl, etc.); a compound wherein a carboxyl group of the compound of the present invention is modified with ester, amide, etc. (e.g. a compound wherein a carboxyl group of the compound of the present invention is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.);, etc. These compounds can be produced by per se known methods from the present compound.

In addition, the prodrug of the present compound may be a compound which is converted into the present compound under the physiological conditions as described in "Development of Drugs", vol. 7, Molecular Design, pp. 163-198 published in 1990 by Hirokawa Publishing Company.

In addition, the present compound may be labeled with an isotope (e.g., $^3H$, $^{14}C$, $^{35}S$, $^{125}I$, etc.) and the like.

Preparation Methods

The compound represented by the formula (I) or a salt thereof can be prepared, for example, by methods shown in the following Reaction Schemes.

Reaction Scheme 1:

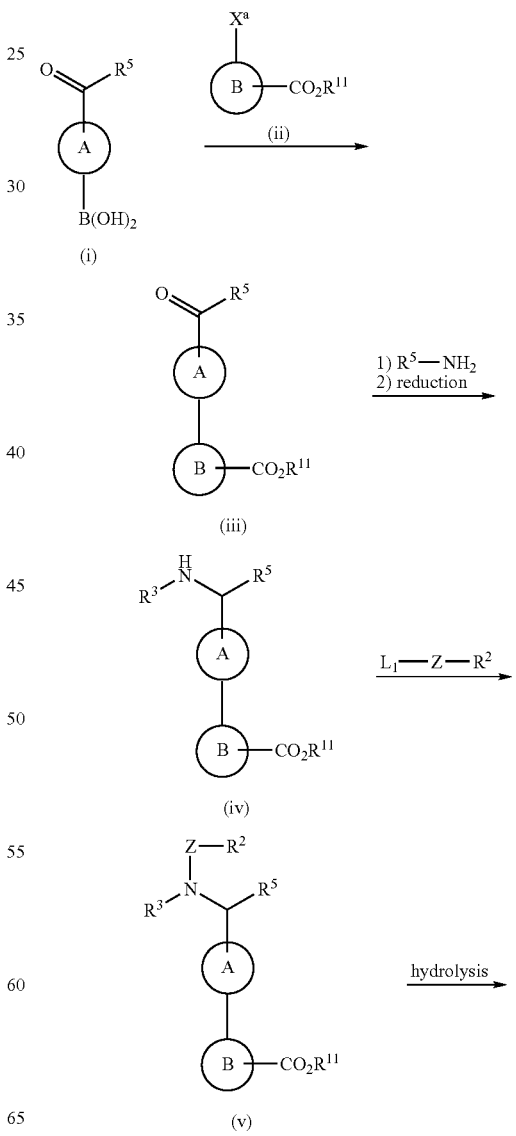

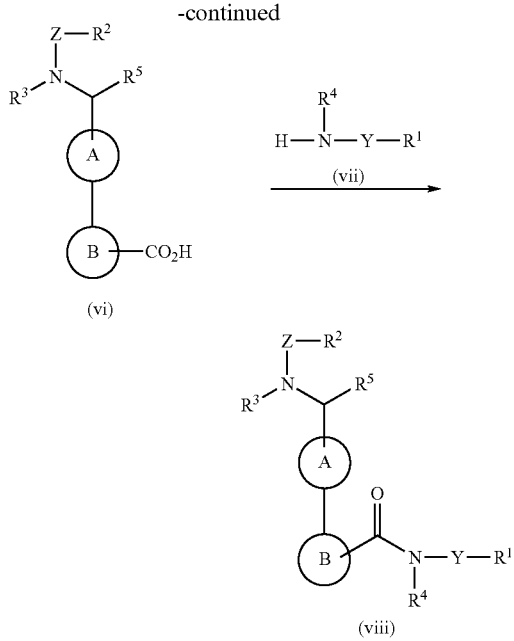

wherein $X^a$ is a leaving group (for example, halogen (fluorine, chlorine, bromine, iodine), trifluoromethanesulfonyloxy group and the like), $L_1$ is a leaving group (for example, halogen (fluorine, chlorine, bromine, iodine), trifluoromethanesulfonyloxy group and the like) or a hydroxy group, $R^{11}$"is $C_{1-4}$alkyl, and the other symbols are the same as defined above.

The compound represented by the formula (iii) or a salt thereof may be prepared by reacting the compound represented by the formula (ii) or a salt thereof with the boronic acid derivative (i), in a solvent under basic condition in the presence of transitional metal catalyst. Examples of the solvent to be used include water, alcoholic solvent (for example, methanol, ethanol, n-propanol, isopropanol and the like), ether solvent (for example, diethyl ether, tetrahydrofuran, 1,2-dimethoxyethane and the like), hydrocarbon solvent (for example, benzene, toluene, hexane, heptane and the like) and N,N-dimethylformamide. These solvents may be used alone, or if necessary, in a mixture of two or more types in appropriate ratio. Examples of the base used include alkali metal or alkali earth metal carbonate (for example, sodium carbonate, potassium carbonate and the like), alkali metal or alkali earth metal bicarbonate (for example, sodium bicarbonate, potassium bicarbonate and the like), hydroxide of alkali metal or alkali earth metal (for example, sodium hydroxide, potassium hydroxide and the like), triethylamine, 4-dimethylaminopyridine, N,N-diisopropylethylamine, triethylenediamine, 4-methyl morpholine and the like. Examples of the transitional metal catalyst used include palladium catalyst [for example, tetrakis(triphenylphosphine)palladium, 1,1-bis(diphenylphosphino)ferrocene dichloropalladium, dichlorobis(triphenylphosphine)palladium and the like] and the like. To 1 mole of the compound represented by the formula (ii) or a salt thereof, boronic acid derivative (i) is used in an amount of about 0.5 to 10 molar equivalents, preferably about 1 to 5 molar equivalents, and transitional metal catalyst in an amount of about 0.01 to 1 molar equivalents, preferably about 0.05 to 0.2 molar equivalents. The reaction temperature is about 0 to 200° C., preferably about 50 to 100° C., and the reaction time is about 0.5 to 48 hours, preferably about 1 or 24 hours.

The compound represented by the formula (iv) or a salt thereof can be prepared by reductive amination using the compound represented by the formula (iii) or a salt thereof, and the amine represented by the formula $R^3NH_2$ or a salt thereof. The reductive amination may be carried out, for example, by reacting the compound represented by the formula (iii) or a salt thereof, and the amine represented by the formula $R^3NH_2$ or a salt thereof, in a solvent such as ether solvent (for example, diethyl ether, tetrahydrofuran, dioxane and the like), hydrocarbon solvent (for example, benzene, toluene, hexane, heptane and the like), halogen solvent (for example, dichloromethane, dichloroethane, chloroform, carbon tetrachloride and the like), alcoholic solvent (for example, methanol, ethanol, n-propanol, isopropanol and the like), acetonitrile, N,N-dimethylformamide, acetic acid and the like or a mixed solvent thereof, in the presence of metal hydrogen complex (for example, sodium borohydride, sodium cyanoborohydride, sodium triacetoxyborohydride and the like). To 1 mole of the compound represented by the formula (iii) or a salt thereof, the amine represented by the formula $R^3NH_2$ or a salt thereof is used in an amount of about 0.5 to 10 molar equivalents, preferably about 1 to 5 molar equivalents, and metal hydrogen complex in an amount of about 0.5 to 10 molar equivalents, preferably about 1 to 5 molar equivalents. The reaction temperature is about 0 to 200° C., preferably about 20 to 100° C., and the reaction time is about 0.5 to 96 hours, preferably about 1 or 24 hours.

The compound represented by the formula (v) or a salt thereof can be prepared by reacting the compound represented by the formula (iv) and an acidic compound represented by the formula $L_1$-Z—$R^2$ or a reactive derivative thereof, or a salt thereof in a solvent using a condensing agent, if necessary, in presence of base. Examples of the reactive derivative of the acidic compound include acid anhydride, active ester (for example, p-nitrophenyl ester, N-hydroxysuccinimide ester, pentafluorophenyl ester, 1-hydroxybenzotriazole ester and the like), acid halide (for example, acid chloride, acid bromide and the like), imidazolide or mixed acid anhydride (for example, anhydride with methyl carbonate, anhydride with ethyl carbonate and the like) and the like. The specific examples of the reactive derivative include those wherein $L_1$ is a leaving group [for example, halogen (fluorine, chlorine, bromine, iodine and the like), methanesulfonyloxy, benzenesulfonyloxy, p-toluene sulfonyloxy and the like] and the like. Examples of the solvent used include ether solvent (for example, diethyl ether, tetrahydrofuran, dioxane and the like), hydrocarbon solvent (for example, benzene, toluene, hexane, heptane and the like), halogen solvent (for example, dichloromethane, dichloroethane, chloroform, carbon tetrachloride and the like), acetonitrile, N,N-dimethylformamide and the like. Examples of the base used include an organic base such as triethylamine, 4-dimethylaminopyridine, N,N-diisopropylethylamine, triethylenediamine and 4-methyl morpholine, alkali metal or alkali earth metal carbonate (for example, sodium carbonate, potassium carbonate and the like), alkali metal or alkali earth metal bicarbonate (for example, sodium bicarbonate, potassium bicarbonate and the like), alkali metal or alkali earth metal hydroxide (for example, sodium hydroxide, potassium hydroxide and the like) and the like. Examples of the condensing agent used include those used in peptide synthesis, specifically for example, dicyclohexylcarbodiimide, diisopropylcarbodiimide, N-ethyl-N'-3-dimethyl aminopropylcarbodiimide and a hydrochloride thereof, benzotriazol-1-yl-tris(dimethylamino)phosphonium hexafluorophosphide, benzotriazol-1-yl-trispyrrolidinophosphonium hexafluorophosphide, cyanodiethyl phosphate, diphenylphosphorylazide, N-hydroxy-5-norbornen-2,3-carboxamide and the like. These condensing agents may be used alone, or in a combination with 1-hydroxybenzotriazole, 1-hydroxy-7-azabenzotriazole and the like. To 1 mole of the compound represented by the formula (iv) or a salt thereof, the acidic compound represented by the formula $L_1$-Z—$R^2$ or a reactive derivative thereof or a salt thereof is used in an amount of about 0.5 to 10 molar equivalents, preferably about 1 to 5 molar equivalents, and condensing agent in an amount of about 0.5 to 10 molar equivalents, preferably about 1 to 6 molar equivalents. The reaction temperature is about −50 to 200° C., preferably about −20 to 100° C., and the reaction time is about 0.5 to 96 hours, preferably about 0.5 to for 72 hours, ore preferably about 1 or 24 hours.

The compound represented by the formula (vi) or a salt thereof can be prepared by treating the compound represented by the formula (v) or a salt thereof with acid or base, i.e., by reacting the compound represented by the formula (v) or a salt thereof, in a solvent such as water, ether solvent (for example, diethyl ether, tetrahydrofuran, dioxane and the like), alcoholic solvent (for example, methanol, ethanol, n-propanol, isopropanol and the like) and the like or a mixed solvent thereof, with mineral acid (for example, nitric acid, hydrochloric acid, hydrobromic acid, iodic acid, sulfuric acid and the like) or alkali metal hydroxide (for example, sodium hydroxide, potassium hydroxide, lithium hydroxide and the like) at about 0 to 150° C., preferably about 20 to 50° C. The concentrations of the acid and base are preferably about 0.1 to 10 N, and the reaction time is about 1 to for 72 hours.

The compound represented by the formula (viii) or a salt thereof can be prepared by reacting the compound represented by the formula (vi) or a reactive derivative thereof or a salt thereof, and the compound represented by the formula (vii) or a salt thereof in a solvent using a condensing agent, if necessary, in presence of base. Examples of the reactive derivative of the compound represented by the formula (vi) include acid anhydride, active ester (for example, p-nitrophenyl ester, N-hydroxysuccinimide ester, pentafluorophenyl ester, 1-hydroxybenzotriazole ester and the like), acid halide (for example, acid chloride, acid bromide and the like), imidazolide or mixed acid anhydride (for example, anhydride with methyl carbonate, anhydride with ethyl carbonate and the like) and the like. Examples of the solvent used include ether solvent (for example, diethyl ether, tetrahydrofuran, dioxane and the like), hydrocarbon solvent (for example, benzene, toluene, hexane, heptane and the like), halogen solvent (for example, dichloromethane, dichloroethane, chloroform, carbon tetrachloride and the like), acetonitrile, N,N-dimethylformamide and the like. Examples of the base used include an organic base such as triethylamine, 4-dimethylaminopyridine, N,N-diisopropylethylamine, triethylenediamine and 4-methyl morpholine, alkali metal or alkali earth metal carbonate (for example, sodium carbonate, potassium carbonate and the like), alkali metal or alkali earth metal bicarbonate (for example, sodium bicarbonate, potassium bicarbonate and the like), alkali metal or alkali earth metal hydroxide (for example, sodium hydroxide, potassium hydroxide and the like) and the like. The condensing agent used include those used in peptide synthesis, specifically for example, dicyclohexylcarbodiimide, lo diisopropylcarbodiimide, N-ethyl-N'-3-dimethyl aminopropylcarbodiimide and a hydrochloride thereof, benzotriazol-1-yl-tris(dimethyl amino)phosphonium hexafluorophosphide, benzotriazol-1-yl-trispyrrolidinophosphonium hexafluorophosphide, cyanodiethyl phosphate, diphenylphosphorylazide, and the like.

These may be used alone, or in a combination with 1-hydroxybenzotriazole, 1-hydroxy-7-azabenzotriazole and the like. To 1 mole of the compound represented by the formula (vi) or a salt thereof, the compound represented by the formula (vii) or a salt thereof is used in an amount of about 0.5 to 10 molar equivalents, preferably about 1 to 5 molar equivalents, and condensing agent in an amount of about 0.5 to 10 molar equivalents, preferably about 1 to 6 molar equivalents. The reaction temperature is about −50 to 200° C., preferably about −20 to 100° C., and the reaction time is about 0.5 to 96 hours, preferably about 0.5 to for 72 hours, more preferably about 1 or 24 hours.

Reaction Scheme 2:

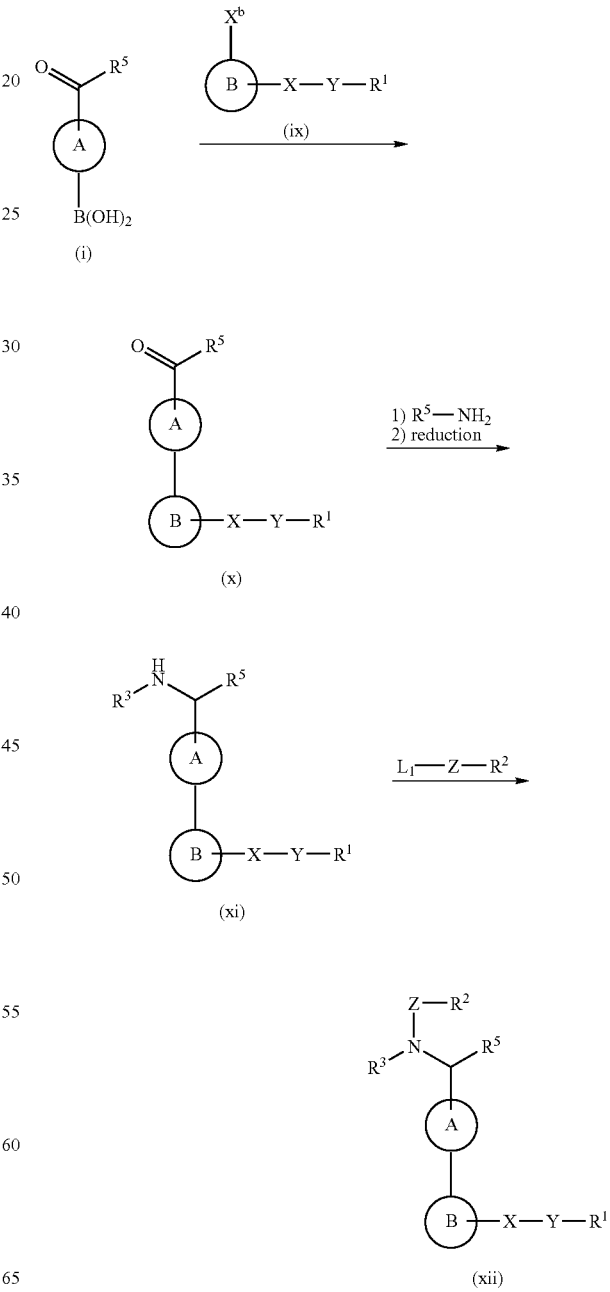

wherein $X^b$ is a leaving group (for example, halogen (fluorine, chlorine, bromine, iodine), trifluoromethanesulfonyloxy group and the like), $L_1$ is a leaving group (for example, halogen (fluorine, chlorine, bromine, iodine), trifluoromethanesulfonyloxy group and the like) or a hydroxy group, and the other symbols are the same as defined above.

The compound represented by the formula (x) or a salt thereof can be prepared by reacting the compound represented by the formula (i) or a salt thereof, and the compound represented by the formula (ix) or a salt thereof. This reaction may be carried out using the same condition as in the above-mentioned Reaction Scheme 1 in which the compound represented by the formula (iii) or a salt thereof is prepared by reacting the compound represented by the formula (i) or a salt thereof, and the compound represented by the formula (ii) or a salt thereof.

The compound represented by the formula (xi) or a salt thereof can be prepared by the conditions of reductive amination using the compound represented by the formula (x) or a salt thereof, and the amine represented by the formula $R^3NH_2$ or a salt thereof. This reaction may be carried out using the same condition as in the above-mentioned Reaction Scheme 1 in which the compound represented by the formula (iv) or a salt thereof is prepared by reacting the compound represented by the formula (iii) or a salt thereof, and the amine represented by the formula $R^3NH_2$ or a salt thereof.

The compound represented by the formula (xii) or a salt thereof can be prepared by reacting the compound represented by the formula (xi) or a salt thereof and an acidic compound represented by the formula $L_1$-Z—$R^2$, a reactive derivative thereof or salts thereof in a solvent using a condensing agent, if necessary, in presence of base. This reaction may be carried out using the same condition as in the above-mentioned Reaction Scheme 1 in which the compound represented by the formula (v) or a salt thereof is prepared by reacting the compound represented by the formula (iv) or a salt thereof, and the acidic compound represented by the formula $L_1$-Z—$R^2$, a reactive derivative thereof or salts thereof.

The compounds represented by the formula (iii), (iv) and (v) or a salt thereof which are used in Reaction Scheme 1 can be prepared based on the following preparation method.

Reaction Scheme 3:

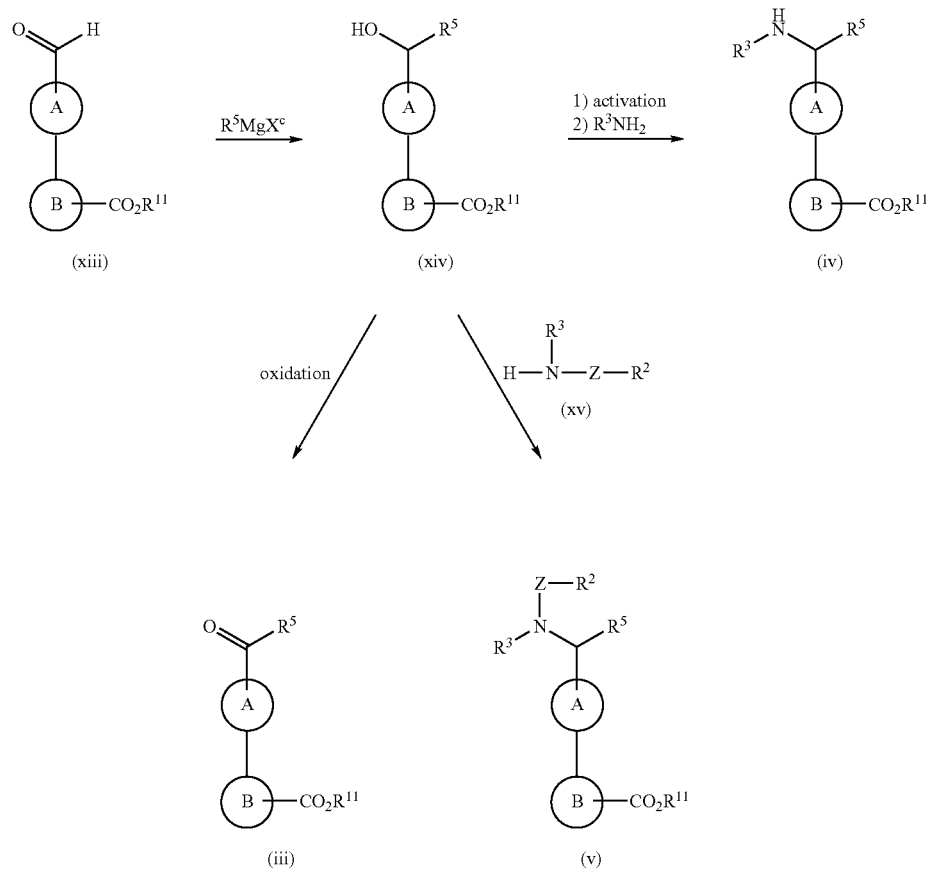

wherein $X^c$ is halogen (fluorine, chlorine, bromine, iodine), and the other symbols are the same as defined above.

The compound represented by the formula (xiv) or a salt thereof can be prepared by reacting the compound represented by the formula (xiii) or a salt thereof and the compound represented by the formula $R^5MgX^c$ or a salt thereof. Specifically, the compound represented by the formula (xiv) or a salt thereof can be prepared by reacting the compound represented by the formula (xiii) or a salt thereof and, about 1 to 10 equivalents, preferably about 1 to 5 equivalents of the compound represented by the formula $R^5MgX^c$ or a salt thereof in a solvent. Examples of the solvent used include ether solvent (for example, diethyl ether, tetrahydrofuran and the like), hydrocarbon solvent (benzene, toluene, hexane, heptane and the like) and halogen solvent (dichloromethane and the like). These solvents may be used alone, or if necessary, in a mixture of two or more kinds in appropriate ratio. The reaction temperature is about −100 to 20° C., preferably −80 to −20° C.

The compound represented by the formula (iv) or a salt thereof can be prepared by activating the compound represented by the formula (xiv) or a salt thereof followed by reacting it with the amine represented by the formula $R^3NH_2$ or a salt thereof. The activation for the compound represented by the formula (xiv) or a salt thereof can be carried out in a solvent using about 1 to 10 equivalents, preferably about 1 to 5 equivalents of a halogenating agent such as thionyl chloride, phosphorous trichloride, phosphorous pentachloride, phosphorous tribromide, phosphorous pentabromide, carbon tetrabromide-triphenylphosphine and the like, or using about 1 to 10 equivalents, preferably about 1 to 5 equivalents of p-toluene sulfonyl chloride, methanesulfonyl chloride and trifluoromethanesulfonic acid anhydride in presence of a base (organic base such as triethylamine, 4-dimethylaminopyridine, N,N-diisopropylethylamine, triethylenediamine and 4-methyl morpholine, or alkali metal or alkali earth metal carbonate (for example, sodium carbonate, potassium carbonate and the like), alkali metal or alkali earth metal bicarbonate (for example, sodium bicarbonate, potassium bicarbonate and the like), alkali metal or alkali earth metal hydroxide (for example, sodium hydroxide, potassium hydroxide and the like) and the like). Examples of the solvent used include acetonitrile, halogen solvent (dichloromethane, chloroform and the like), ether solvent (diethyl ether, tetrahydrofuran and the like), hydrocarbon solvent (for example, benzene, toluene, hexane, heptane and the like), and the like. The reaction temperature is about −20 to 100° C., preferably about 0 to 60° C. Furthermore, the activated compound represented by the formula (xiv) or a salt thereof may be iodated using potassium iodide, sodium iodide and the like in a solvent such as acetonitrile and N,N-dimethylformamide. This activated compound represented by the formula (xiv) or a salt thereof can be reacted with about 1 to 10 equivalents, preferably about 1 to 5 equivalents of the amine represented by the formula $R^3NH_2$ or a salt thereof in a solvent to prepare the compound represented by the formula (iv) or a salt thereof. Examples of the solvent to be used include acetonitrile, halogen solvent (dichloromethane, chloroform and the like), ether solvent (diethyl ether, tetrahydrofuran and the like), hydrocarbon solvent (for example, benzene, toluene, hexane, heptane and the like), N,N-dimethylformamide, N,N-dimethyl acetamide and the like, and the reaction temperature is about −20 to 150° C., preferably about 0 to 100° C. In this reaction, a base (organic base such as triethylamine, 4-dimethylaminopyridine, N,N-diisopropylethylamine, triethylenediamine and 4-methyl morpholine, or alkali metal or alkali earth metal carbonate (for example, sodium carbonate, potassium carbonate and the like), alkali metal or alkali earth metal bicarbonate (for example, sodium bicarbonate, potassium bicarbonate and the like), alkali metal or alkali earth metal hydroxide (for example, sodium hydroxide, potassium hydroxide and the like), and the like may or may not be present.

The compound represented by the formula (iii) or a salt thereof can be prepared by oxidation of the compound represented by the formula (xiv) or a salt thereof. Specifically, the compound represented by the formula (iii) can be prepared by treating the compound represented by the formula (xiv) or a salt thereof with 1 to 10 equivalents, preferably 1 to 3 equivalents of manganese dioxide, pyridinium chlorochromate, dimethyl sulfoxide-anhydrous trifluoroacetic acid (Swern method), dimethyl sulfoxide-acetic anhydride (Albright-Goldman method) and the like, in an appropriate solvent such as halogen solvent (dichloromethane, chloroform and the like). The reaction temperature is about −70 to 100° C., preferably about −40 to 60° C., and the reaction time is about 1 or 24 hours, preferably about 1 to 15 hours.

The compound represented by the formula (v) or a salt thereof can be prepared by Mitsunobu Reaction (Synthesis, 1981, pages 1 to 27) or a modified method thereof using the compound represented by the formula (xiv) or a salt thereof, and the compound represented by the formula (xv) or a salt thereof. The reaction maybe carried out by reacting the compound represented by the formula (xiv) or a salt thereof, and the compound represented by the formula (xv) or a salt thereof in presence of azodicarboxylate (for example, diethylazodicarboxylate, 1,1'-(azodicarbonyl)dipiperidine and the like) and phosphine (for example, triphenylphosphine, tributylphosphine and the like). To 1 mole of the compound represented by the formula (xiv) or a salt thereof, the compound represented by the formula (xv) or a salt thereof is used in an amount of preferably about 1 to 5 moles, more preferably about 1 or 2 moles of, and the "azodicarboxylate" and "phosphine" in an amount of about 1 to 5 moles, preferably about 1 or 2 moles. This reaction is favorably carried out in an inert solvent for the reaction. Such solvent is not limited if it does not affect the reaction, and include, for example, ether solvent (for example, diethyl ether, tetrahydrofuran, dioxane and the like), hydrocarbon solvent (for example, benzene, toluene, hexane, heptane and the like), halogen solvent (for example, dichloromethane, dichloroethane, chloroform, carbon tetrachloride and the like), acetonitrile, N,N-dimethylformamide and the like.

Alternatively, the compound of the present invention can be prepared by the following method.

Reaction Scheme 4:

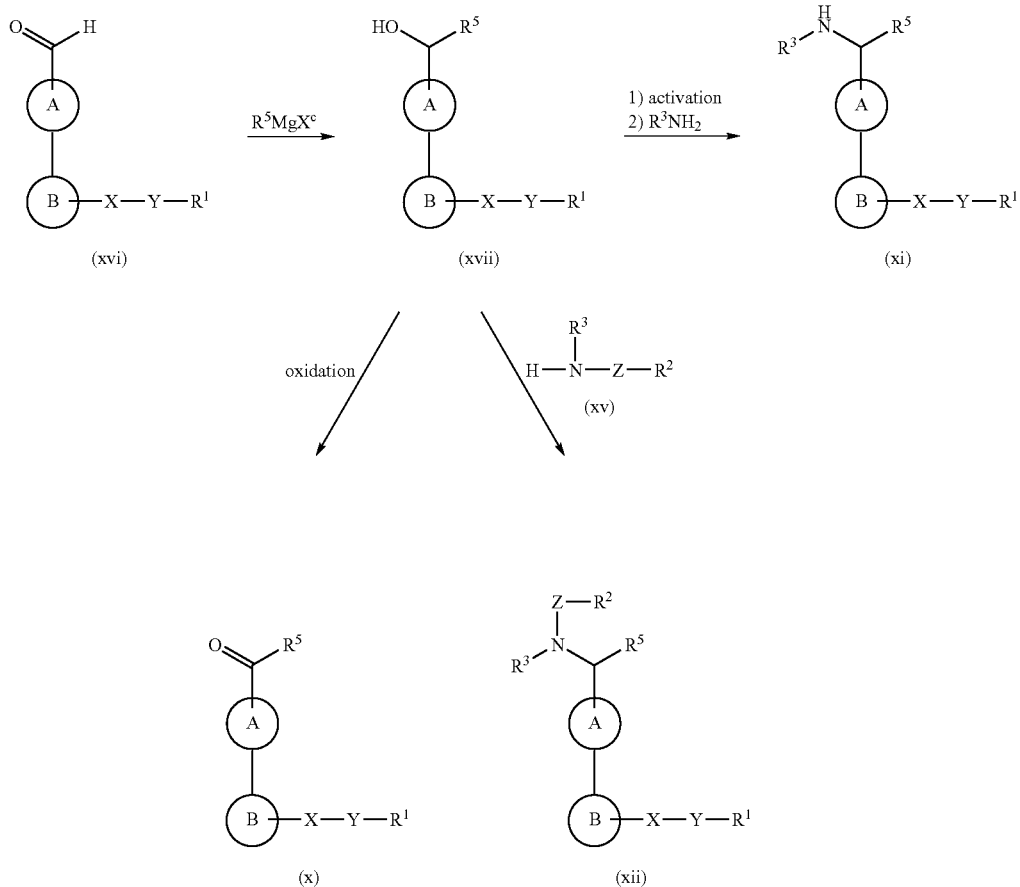

wherein $X^c$ is halogen (fluorine, chlorine, bromine, iodine), and the other symbols are the same as defined above.

The compound represented by the formula (xvii) or a salt thereof can be prepared by reacting the compound represented by the formula (xvi) or a salt thereof and the compound represented by the formula $R^5MgX^c$ or a salt thereof. This reaction may be carried out using the same conditions as in the above-mentioned Reaction Scheme 3 in which the compound represented by the formula (xiv) or a salt thereof is prepared by reacting the compound represented by the formula (xiii) or a salt thereof, and the compound represented by the formula $R^5MgX^c$ or a salt thereof.

The compound represented by the formula (xi) or a salt thereof can be prepared by activating the compound represented by the formula (xvii) or a salt thereof followed by reacting it with the amine represented by the formula $R^3NH_2$ or a salt thereof. This reaction may be carried out using the same conditions as in the above-mentioned Reaction Scheme 3 in which the compound represented by the formula (iv) or a salt thereof is prepared by reacting the compound represented by the formula (xiv) or a salt thereof, and the amine represented by the formula or a salt thereof.

The compound represented by the formula (x) or a salt thereof used in Reaction Scheme 2 also may be prepared by oxidation of the compound represented by the formula (xvii) or a salt thereof. This reaction may be carried out using the same conditions as in the above-mentioned Reaction Scheme 3 in which the compound represented by the formula (xiv) or a salt thereof is oxidized to prepare the compound represented by the formula (iii) or a salt thereof.

The compound represented by the formula (xii) or a salt thereof can be prepared by Mitsunobu Reaction using the compound represented by the formula (xvii) or a salt thereof and the compound represented by the formula (xv) or a salt thereof. This reaction may be carried out using the same conditions as in the above-mentioned Reaction Scheme 3 in which the compound represented by the formula (v) or a salt thereof is prepared by reacting the compound represented by the formula (xiv) or a salt thereof, the compound represented by the formula (xv) or a salt thereof.

The compound represented by the formula (v) or a salt thereof which is used in Reaction Scheme 1 can be prepared based on the following preparation method.

Reaction Scheme 5

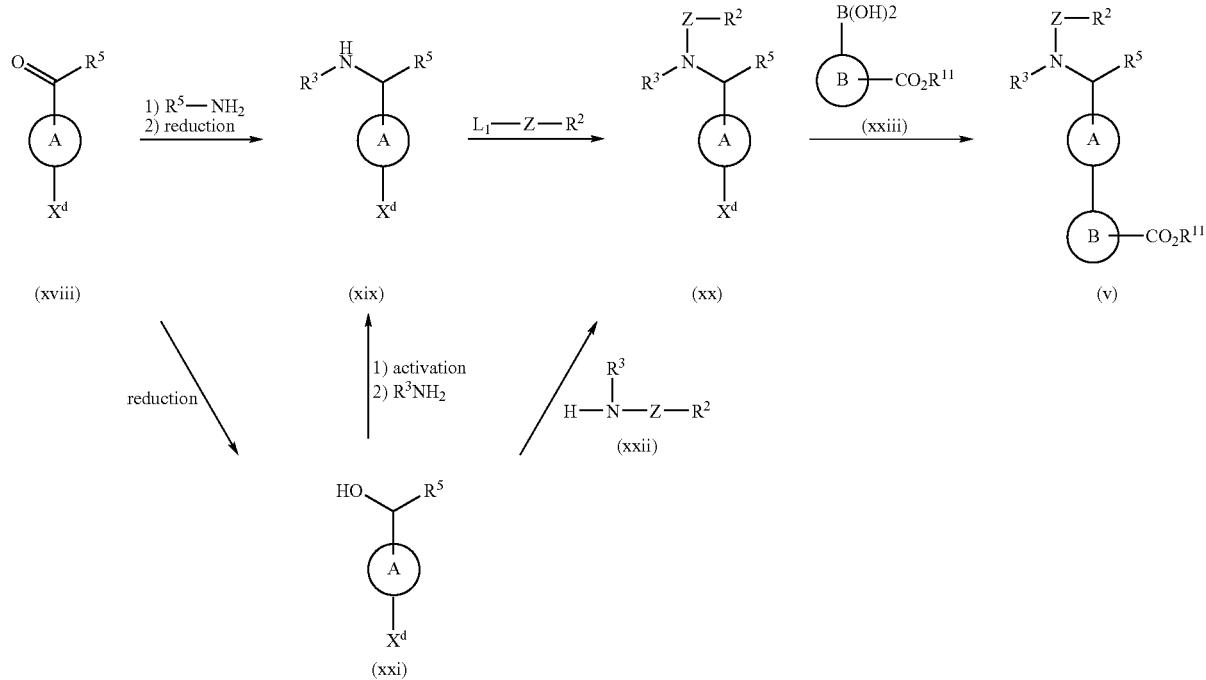

wherein $X^d$ is halogen (fluorine, chlorine, bromine, iodine), $L_1$ is a leaving group (for example, halogen (fluorine, chlorine, bromine, iodine), trifluoromethanesulfonyloxy group and the like) or a hydroxy group, $R^{11}$ is $C_{1-4}$alkyl, and the other symbols are the same as defined above.

The compound represented by the formula (xix) or a salt thereof can be prepared by the conditions of reductive amination using the compound represented by the formula (xviii) or a salt thereof, and the amine represented by the formula $R^3NH_2$ or a salt thereof. This reaction may be carried out using the same conditions as in the above-mentioned Reaction Scheme 1 in which the compound represented by the formula (iv) or a salt thereof is prepared by reacting the compound represented by the formula (iii) or a salt thereof, and the amine represented by the formula $R^3NH_2$ or a salt thereof.

The compound represented by the formula (xx) or a salt thereof can be prepared by reacting the compound represented by the formula (xix) or a salt thereof and an acidic compound represented by the formula $L_1$-Z—$R^2$, a reactive derivative thereof or salts thereof in a solvent using a condensing agent, if necessary, in presence of base. This reaction may be carried out using the same conditions as in the above-mentioned Reaction Scheme 1 in which the compound represented by the formula (v) or a salt thereof is prepared by reacting the compound represented by the formula (iv) or a salt thereof, and the acidic compound represented by the formula $L_1$-Z—$R^2$ or a reactive derivative thereof, or a salt thereof.

In addition, the compound represented by the formula (xix) or a salt thereof and the compound represented by the formula (xx) or a salt thereof may be prepared from the compound represented by the formula (xxi) or a salt thereof.

The compound represented by the formula (xxi) or a salt thereof can be prepared by reduction of the compound represented by the formula (xviii) or a salt thereof. For example, the compound represented by the formula (xxi) or a salt thereof can be prepared by reacting the compound represented by the formula (xviii) or a salt thereof, with metal hydrogen complex (for example, sodium borohydride, sodium cyanoborohydride, sodium triacetoxyborohydride, aluminum diisobutyl hydride, sodium lithium hydride and the like) in a solvent such as ether solvent (for example, diethyl ether, tetrahydrofuran, dioxane and the like), hydrocarbon solvent (for example, benzene, toluene, hexane, heptane and the like), halogen solvent (for example, dichloromethane, dichloroethane, chloroform, carbon tetrachloride and the like), acetonitrile, N,N-dimethylformamide, acetic acid and the like or a mixed solvent thereof. To 1 mole of the compound represented by the formula (xviii) or a salt thereof, metal hydrogen complex is used in an amount of about 0.5 to 10 molar equivalents, preferably about 1 to 5 molar equivalents. The reaction temperature is about 0 to 200° C., preferably about 20 to 100° C. and the reaction time is about 0.5 to 96 hours, preferably about 1 or 24 hours.

The compound represented by the formula (xix) or a salt thereof can be prepared by activating the compound represented by the formula (xxi) or a salt thereof followed by reacting it with the amine represented by the formula $R^3NH_2$ or a salt thereof. This reaction may be carried out using the same conditions as in the above-mentioned Reaction Scheme 3 in which the compound represented by the formula (iv) or a salt thereof is prepared by reacting the compound represented by the formula (xiv) or a salt thereof, and the amine represented by the formula $R^3NH_2$ or a salt thereof.

The compound represented by the formula (xx) or a salt thereof can be prepared by Mitsunobu Reaction using the compound represented by the formula (xxi) or a salt thereof and the compound represented by the formula (xxii) or a salt thereof. This reaction may be carried out using the same conditions as in the above-mentioned Reaction Scheme 3 in which the compound represented by the formula (v) or a salt thereof is prepared by reacting the compound represented by the formula (xiv) or a salt thereof, the compound represented by the formula (xv) or a salt thereof.

The compound represented by the formula (v) or a salt thereof may be prepared by reacting the compound represented by the formula (xx) or a salt thereof with boronic acid derivative (xxiii), in a solvent under basic condition in the presence of transitional metal catalyst. This reaction may be carried out using the same conditions as in the above-mentioned Reaction Scheme 1 in which the compound represented by the formula (iii) or a salt thereof is prepared by reacting the compound represented by the formula (i) or a salt thereof, and the formula (ii) represented by compound or a salt thereof.

The compound represented by the formula (xii) or a salt thereof can be also prepared by the following method.

Reaction Scheme 6:

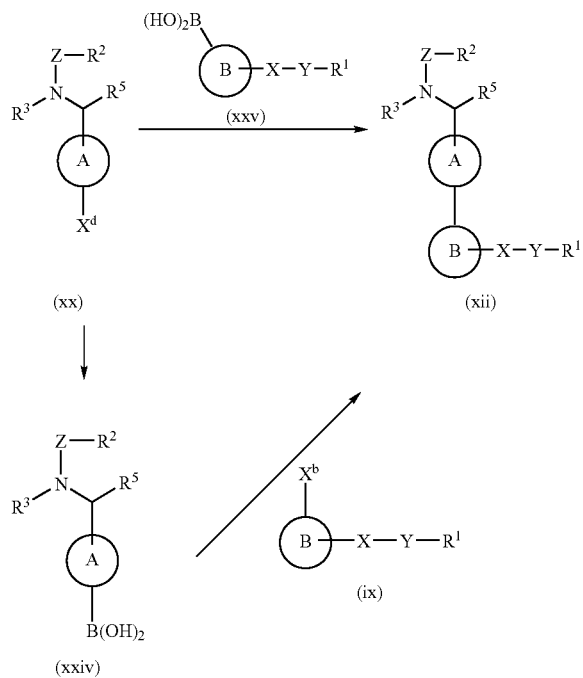

wherein $X^b$ and $X^d$ are halogen (fluorine, chlorine, bromine, iodine), and the other symbols are the same as defined above.

The compound represented by the formula (xxiv) or a salt thereof can be prepared by converting the compound represented by the formula (xx) or a salt thereof to a boronic acid thereof. Specifically, the compound represented by the formula (xx) or a salt thereof is treated with a strong base in a solvent to produce carbon anion, which is reacted with about 1 to 10 equivalents, preferably about 1 to 5 equivalents of a boronic acid derivative such as trimethoxyboronic acid and triisopropoxyboronic acid, and then treated with an acid such as hydrochloric acid, to prepare the compound represented by the formula (xxiv) or a salt thereof. Examples of the solvent used include ether solvent (for example, diethyl ether, tetrahydrofuran and the like), hydrocarbon solvent (benzene, toluene, hexane, heptane and the like) and halogen solvent (dichloromethane and the like). As the strong base, about 1 to 5 molar equivalents, preferably about 1 to 3 equivalents of a lithium agent such as n-butyllithium, sec-butyllithium, tert-butyllithium and lithium diisopropylamide is used. The reaction temperature is about −100 to 0° C., preferably about −100 to −20° C.

The compound represented by the formula (xii) or a salt thereof can be prepared by reacting (1) the compound represented by the formula (xx) or a salt thereof, and the compound represented by the formula (xxv) or a salt thereof, or (2) the compound represented by the formula (xxiv) or a salt thereof, and the compound represented by the formula (ix) or a salt thereof. This reaction may be carried out using the same conditions as in the above-mentioned Reaction Scheme 1 in which the compound represented by the formula (iii) or a salt thereof is prepared by reacting the compound represented by the formula (i) or a salt thereof, and the formula (ii) represented by compound or a salt thereof.

The resulting compound according to the present invention can be isolated and purified by the known separation and purification methods such as concentration, concentration under reduced pressure, solvent extraction, crystallization, recrystallization, solvent convert, chromatography, etc.

The compounds used in each of the above-described preparation methods may form a salt corresponding to the salt of the compound according to the present invention unless it adversely affects the reaction.

In addition, in each reaction, when the starting compounds have an amino group, a carboxyl group and/or a hydroxy group as substituents, these groups may be protected by protective groups such as those generally employed in peptide chemistry, etc. After the reaction, if necessary, the protective groups may be removed to obtain the desired compound.

Examples of an amino protective group include an optionally substituted $C_{1-6}$alkylcarbonyl (for example, acetyl, propionyl, and the like), formyl, phenylcarbonyl, $C_{1-6}$alkyloxycarbonyl (for example, methoxycarbonyl, ethoxycarbonyl, tert-butoxycarbonyl, and the like), phenyloxycarbonyl (for example, benzoxycarbonyl, and the like), $C_{7-14}$aralkyloxycarbonyl (for example, benzyloxycarbonyl, 9-fluorenylmethoxycarbonyl and the like), trityl, phthaloyl, and the like. These substituents may be substituted by 1 to 3 substituents such as halogen (for example, fluorine, chlorine, bromine, iodine, and the like), $C_{1-6}$alkylcarbonyl (for example, acetyl, propionyl, butyryl, and the like), nitro group, and the like.

Examples of a carboxyl protective group include an optionally substituted $C_{1-6}$alkyl (for example, methyl, ethyl, propyl, isopropyl, butyl, tert-butyl, and the like), phenyl, trityl, silyl, and the like. These substituents may be substituted by 1 to 3 substituents such as halogen (for example, fluorine, chlorine, bromine, iodine, and the like), $C_{1-6}$alkylcarbonyl (for example, acetyl, propionyl, butyryl, and the like), formyl, nitro group, and the like.

Examples of a hydroxy protective group include an optionally substituted $C_{1-6}$alkyl (for example, methyl, ethyl, propyl, isopropyl, butyl, tert-butyl, and the like), phenyl, $C_{7-10}$aralkyl (for example, benzyl, and the like), $C_{1-6}$alkylcarbonyl (for example, acetyl, propionyl, and the like), formyl, phenyloxycarbonyl, $C_{7-10}$aralkyloxycarbonyl (for example, benzyloxycarbonyl, and the like), pyranyl, furanyl, silyl, and the like. These substituents may be substituted by 1 to 4 substituents such as halogen (for example, fluorine, chlorine, bromine, iodine, and the like), $C_{1-6}$alkyl, phenyl, $C_{7-10}$aralkyl, nitro group, and the like.

These protective groups may be introduced or removed by per se known methods (for example a method described in Protective Groups in Organic Chemistry (J. F. W. McOmie et al.; Plenum Press Inc.) or a similar method thereto. For example, employable methods for removing the protective groups include a method using an acid, a base, reduction, ultraviolet ray, hydrazine, phenylhydrazine, sodium N-methyldithiocarbamate, tetrabutylammonium fluoride, palladium acetate, and the like.

Because the compound according to the present invention has strong melanocortin receptor agonist or antagonist activity, it can be used as an agent for preventing or treating a variety of diseases caused by or related to melanocortin. Among others, the compound according to the present invention is useful as an agent for preventing or treating inflammatory diseases (for example, diabetic complications such as pain and fever, proliferative retinopathy, nephrotic syndrome, neural disorder and great-vessel disorder, arthritis such as rheumatism, chronic articular rheumatism, osteoarthritis, rheumatoid spondylitis, gouty arthritis and periostitis, backache, gout, post-operative and/or post-traumatic inflammation, alleviation of swelling, neuralgia, sore throat, cystitis, chronic hepatitis, acute pancreatitis, chronic pancreatitis, inflammatory bowel diseases such as Crohn's disease and ulcerative colitis, meningitis, inflammatory optic disease, inflammatory pulmonary diseases such as pneumonia, silicotis, pulmonary sarcoidosis, and pulmonary tuberculosis, and the like), AIDS, obesity, bulimia, anorexia and the like or as an agent for improving affective disorder or sexual dysfunction, and the like.

In particular, the compound according to the present invention can be used usefully as an agent for preventing or treating obesity since melanocortin receptor agonist has an action of feeding suppression, and as an agent for preventing or treating anorexia since melanocortin receptor antagonist has an action of feeding increasing.

Because the compound according to the present invention has dominant activity as melanocortin receptor agonist, it is especially useful as an agent for preventing or treating obesity.

Furthermore, the compound according to the present invention has sufficiently low toxicity to be safe, and is useful as an agent for preventing or treating bulimia and the like in mammal (for example, rat, mouse, guinea pig, rabbit, sheep, horse, pig, bovine, and simian, human and the like).

The compound according to the present invention can be formulated by a per se known method, and can be safely administered orally or parenterally (for example, topical, rectal, intravenous administration, and the like) as itself or as a pharmaceutical composition, which is produced by compounding with a pharmaceutically acceptable suitable carrier in an suitable amount, for example, in the form of a tablet (including a sugar-coated tablet and a film-coated tablet), a powder, a granule, a capsule (including a soft capsule), a liquid and solution, an injection, a suppository, a sustained-release formulation, or the like.

The content of the compound according to the present invention is usually about 0.1 to 100% by weight based on the total weight of the formulation. The dosage may vary depending on the administration subject, the administration route, the disease to be treated, and the like, but, for example, in case that it is administered orally to an adult (body weight about 60 kg) as an agent for treating bullimia, an unit dosage of the compound of the present invention as the active ingredient is about 0.01 to 500 mg, preferably, about 0.1 to 100 mg, more preferably about 1 to 100 mg, and the dosage can be administered once a day, or multiple times per day.

Though the compound according to the present invention can be used alone to exert excellent melanocortin receptor agonist or antagonist activity, the compound according to the present invention may be also combined with other drug components in addition to the compound of the present invention (hereinafter, briefly referred to as a concomitant drug) (multiple combination).

Such concomitant drugs include a drug for chronic obstructive pulmonary disease (for example, β-stimulant: fenoterol, salbutamol, terbutaline, formoterol and salmeterol; a mucolytic agent: ambroxol, erdosteine and carbocysteine; an expectorant: fudostein; an antioxidant: N-acetylcystein; and the like), antiasthmatics (for example, fluticarsone propionic acid, beclometasone propionic acid, theophylline, aminophylline, procaterol, ketotiphene, aselastin, seratrodast and the like), antiallergics (for example, fexofenadine, epinastine, ebastine and the like), anticholinergics (for example, thiotropium bromide, ipratropium bromide, flutropium bromide, oxytropium bromide and the like), anti-inflammatics (for example, sodium diclofenac, ibuprofen, indomethacin, sodium loxoprofen and the like), antiseptic (for example, cefixime, cefdinyl, ofloxacin, tosfloxacin tosyl acid, levofloxocin and the like), anti-fungal agents (for example, fluconazole, itraconazole and the like), anti-diabetics (for example, pioglitazone, nateglinide, voglibose, acarbose and the like) and the like.

In combining of the compound according to the present invention and the concomitant drug, the compound of the present invention and the concomitant drug may be administered simultaneously or separately at an interval, to a patient. The dosage of the concomitant drug may be in accordance of the conventional dosage clinically used, and may be selected appropriately depending on the administration subject, the administration route, the disease to be treated, a combination thereof, and the like.

Administration forms of the compound of the present invention and the concomitant drug are not particularly limited if the compound of the present invention and the concomitant drug are combined when administered. Such administration forms include (1) administration of single formulation obtained by formulating the compound of the present invention and the concomitant drug together, (2) simultaneous administration of two formulations obtained by formulating the compound of the present invention and the concomitant drug separately via the same administration route, (3) separate administration at a time interval of two formulations obtained by formulating the compound of the present invention and the concomitant drug separately via the same administration route (4) simultaneous administration of two formulations obtained by formulating the compound of the present invention and the concomitant drug separately via different administration routes, (5) separate administration at a time interval of two formulations obtained by formulating the compound of the present invention and the concomitant drug separately via different administration routes (for example, administration of the compound of the present invention first, the concomitant drug later, or vice versa) and the like. Hereinafter, all these administration forms are briefly referred to as the combination drugs according to the present invention.

The combination drugs according to the present invention have low toxicity and can be safely administered orally or parenterally (for example, topical, rectal, intravenous administration, and the like) as a pharmaceutical composition, which is produced by compounding the compound of the present invention or (and) the concomitant drug with a pharmaceutically acceptable carrier according to a per se known method, for example, in the form of a tablet (including a sugar-coated tablet, a film-coated tablet), a powder, a granule, a capsule (including a soft capsule), a liquid and solution, an injection, a suppository, a sustained-release formulation, or the like.

Examples of pharmaceutically acceptable carriers used in the preparation of the drug according to the present invention and the combination drug according to the present invention include various organic or inorganic carriers which are generally used in this field. For example, an excipient, a lubricant, a binder, a disintegrating agent, and the like are used in solid formulations; and a solvent, a solubilizer, a suspending agent, an isotonizing agent, a buffer, a soothing agent, and the like are used in liquid formulations. In addition, if desired, an appropriate additive such as a preservative, antioxidant, a colorant, a sweetener, an adsorbent, a wetting agent and the like may be used.

Suitable examples of the excipient include lactose, sucrose, D-mannitol, starch, corn starch, crystalline cellulose, light silicic acid anhydride, and the like.

Suitable examples of the lubricant include magnesium stearate, calcium stearate, talc, colloidal silica, and the like.

Suitable examples of the binder include crystalline cellulose, sucrose, D-mannitol, dextrin, hydroxypropyl cellulose, hydroxypropylmethyl cellulose, polyvinyl-pyrrolidone, starch, cane sugar, gelatine, methyl cellulose, sodium carboxymethylcellulose and the like.

Suitable examples of the disintegrating agent include starch, carboxymethyl cellulose, carboxymethyl cellulose calcium, croscarmellose sodium, sodium carboxymethyl starch, L-hydroxypropylcellulose and the like.

Suitable examples of the solvent include water for injection, alcohol, propylene glycol, macrogol, sesame oil, corn oil, and the like.

Suitable examples of the solubilizer include polyethylene glycol, propylene glycol, D-mannitol, benzyl benzoate, ethanol, trisaminomethane, cholesterol, triethanolamine, sodium carbonate, sodium citrate, and the like.

Suitable examples of the suspending agent include surfactants such as stearyl triethanolamine, sodium laurylsulfate, laurylaminopropionic acid, lecithin, benzalkonium chloride, benzetonium chloride, glycerin monostearate, and the like; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, and the like.

Suitable examples of the isotonizing agent include dextrose, D-sorbitol, sodium chloride, glycerin, D-mannitol, and the like.

Suitable examples of the buffer include a buffer solution of phosphate, acetate, carbonate, citrate, and the like.

Suitable examples of the soothing agent include benzyl alcohol, and the like.

Suitable examples of the preservative include paraoxybenzoic acid esters, chlorobutanol, benzylalcohol phenethylalcohol, dehydroacetic acid, sorbic acid, and the like.

Suitable examples of the antioxidant include sulfites, ascorbic acid, and the like.

The Sequence Nos. of the sequence list of the present specification represent the following sequences.

[Sequence No.: 1]

Represents the base sequence of primer-1 which is used in the Experimental Example.

[Sequence No.: 2]

Represents the base sequence of primer-2 which is used in the Experimental Example.

BEST MODE FOR CARRYING OUT THE INVENTION

The present invention is hereinafter described in more detail by means of the following Reference Examples, Examples, Experimental Example, and Formulation Example, but these examples are merely illustrative, which are not intended to limit the present invention.

$^1$H-NMR spectra were measured using a Varian GEMINI 200(200 MHz) type spectrometer, a JEOL LAMBDA300 (300 MHz) type spectrometer or a Burker AM 500 (500 MHz) type spectrometer using tetramethylsilane as an internal standard. All "δ" values are shown as ppm. Unless other stated, "%" indicates the percent by weight. However, the % in yield represents mol/mol %. Other symbols used in the specification represent as follows:

s: singlet d: doublet t: triplet q: quartet m: multiplet br: broad

THF: tetrahydrofuran

DMF: N,N-dimethylformamide

HOBt: 1-hydroxybenzotriazole monohydrate

WSC: 1-ethyl-3-(3-dimethylaminopropyl)carbodiimide hydrochloride

Me: methyl group

Room temperature herein refers to the range from about 15 to 25° C., but it is not strictly limited to this range.

The genetic engineering procedures described in the Experimental Example were based on the methods described in a textbook (Maniatis, et al., Molecular Cloning, Cold Spring Harbor Laboratory, 1989) or methods described in the protocols attached to the reagents.

EXAMPLES

Reference Example 1

3'-acetyl-1,1'-biphenyl-2-carboxylic acid ethyl ester

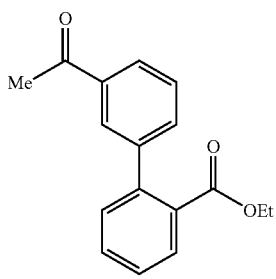

To a suspension of ethyl 2-bromobenzoic acid (10.0 g) and 3-acetylphenylboric acid (7.87 g) in dimethoxyethane (200 ml) was added 2 N sodium carbonate solution (50 ml), and the mixture was deaerated and argon-substituted. To this mixture was added tetrakis(triphenylphosphine) palladium (0) (5.04 g), and the mixture was heated to reflux for 15 hours. The obtained reaction mixture was subjected to cooling, and distributed between ethyl acetate (400 ml) and saturated sodium bicarbonate solution (400 ml). The aqueous layer was further extracted with ethyl acetate (200 ml), and the combined organic layer was washed with saturated brine, dried with magnesium sulfate, and the solvent was distilled off under reduced pressure. The residue was purified by silica gel chromatography to give the title compound as a yellow oil (11.08 g, 95%).

$^1$H-NMR (CDCl$_3$) δ: 1.03 (3H, t), 2.61 (3H, s), 4.09 (2H, q), 7.36 (1H, d), 7.40-7.60 (4H, m), 7.80-8.00 (3H, m).

Reference Example 2

3'-[1-{N-(1-benzylpiperidin-4-yl)amino}ethyl][1,1'-biphenyl]-2-carboxylic acid ethyl ester

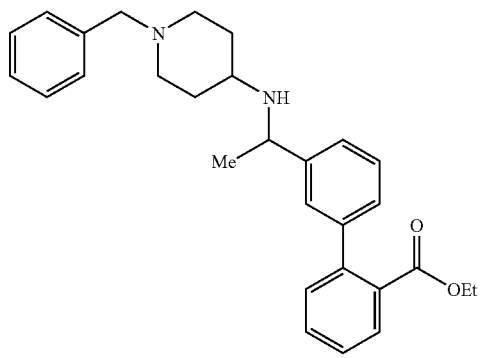

A solution of the compound obtained in Reference Example 1 (2.0 g) and 4-amino-i-benzylpiperidine (4.26 g), and p-toluene sulfonic acid monohydrate (425 mg) in toluene (60 ml) was heated to reflux for 20 hours using Dean Stark apparatus. The reaction mixture was cooled, and concentrated under reduced pressure. The residue was dissolved in methanol (30 ml), sodium borohydride (282 mg) was added under ice-cooling, and the mixture was stirred for 2 hours. The obtained reaction mixture was distributed between ethyl acetate (300 ml) and saturated sodium bicarbonate solution (300 ml). The aqueous layer was further extracted with ethyl acetate (200 ml), the combined organic layer was washed with saturated brine, dried with magnesium sulfate, and the solvent was distilled off under reduced pressure. The residue was purified by silica gel chromatography to give the title compound as a pale brown oil (3.39 g, 100%).

$^1$H-NMR (CDCl$_3$) δ: 0.94 (3H, t), 1.30-1.40 (5H, m), 1.70 (1H, dd), 1.88-1.95 (3H, m), 2.30-2.45 (1H, m), 2.75-2.81 (2H, m), 3.45 (2H, s), 3.96-4.08 (3H, m), 7.18-7.51 (11H, m), 7.50 (1H, t), 7.79 (1H, d)

Reference Example 3

3'-[1-{N-(1-benzylpiperidin-4-yl)-N-(2-naphthylacetyl)amino}ethyl][1,1'-biphenyl]-2-carboxylic acid hydrochloride

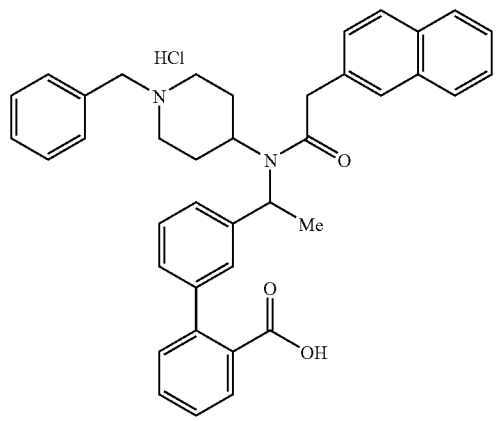

1) 3'-[1-{N-(1-benzylpiperidin-4-yl)-N-(2-naphthylacetyl)amino}ethyl][1,1'-biphenyl]-2-carboxylic acid ethyl ester To a solution of the compound obtained in Reference Example 2 (3.81 g) and triethylamine (2.61 g) in THF (100 ml) was added a solution of 2-naphthylacetyl chloride (5.28 g) in THF (30 ml) under ice-cooling, and the mixture was stirred at room temperature for 16 hours. The reaction mixture was diluted with saturated sodium bicarbonate solution (200 ml) and extracted with ethyl acetate (150 ml) twice. The extracted solutions were combined, washed with saturated brine, dried with magnesium sulfate, and the solvent was distilled off under reduced pressure. The residue was purified by silica gel chromatography to give the title compound as a colorless amorphous substance (3.69 g, 70%).

2) 3'-[1-{N-(1-benzylpiperidin-4-yl)-N-(2-naphthylacetyl)amino}ethyl][1,1'-biphenyl]-2-carboxylic acid hydrochloride The compound obtained in 1) (3.69 g) was dissolved in a mixed solvent of ethanol (75 ml) and THF (30 ml), to this solution was added 4 N sodium hydroxide solution (75 ml), and the mixture was stirred at 50° C. for 4 hours. The reaction mixture was cooled, 1 N hydrochloric acid (350 ml) was added, and extracted with ethyl acetate (100 ml) twice. The extracted solutions were combined, washed with saturated brine, dried with magnesium sulfate, and the solvent was distilled off under reduced pressure. To a solution of the residue in ethanol (10 ml) was added diethyl ether (300 ml), and this solution was purified by reprecipitation to give the title compound as a white powder (3.33 g, 89%).

$^1$H-NMR (CDCl$_3$) δ: 1.44 (3H, d), 1.63 (1H, d), 2.70-3.49 (6H, m), 3.70 (2H, m), 4.13 (2H, s), 4.24 (2H, d), 5.35 (1H, q), 6.66 (1H, br), 7.10-7.26 (3H, m), 7.39-7.58 (11H, m), 7.83-7.93 (4H, m), 8.05 (2H, d), 10.90 (1H, br).

Reference Example 4

3'-acetyl-N-{2-(tert-butoxycarbonylamino)ethyl}-1,1'-biphenyl-2-carboxamide

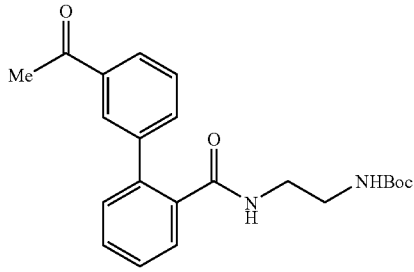

From 2-bromo-N-{2-(tert-butoxycarbonylamino)ethyl}benzamide (0.98 g) was obtained the title compound as a white powder (1.04 g) in the same manner as in Reference Example 1.

$^1$H-NMR (CDCl$_3$) δ: 1.39 (9H, s), 2.64 (3H, s), 3.08 (2H, m), 3.32 (2H, m), 4.70 (1H, br), 5.96 (1H, br), 7.43 (2H, m), 7.53 (2H, q), 7.64 (2H, t), 7.96 (1H, d), 8.03 (1H, s).

Reference Example 5

3'-[1-{N-(1-benzylpiperidin-4-yl)amino}ethyl]-N-{2-(tert-butoxycarbonylamino)ethyl}[1,1'-biphenyl]-2-carboxamide

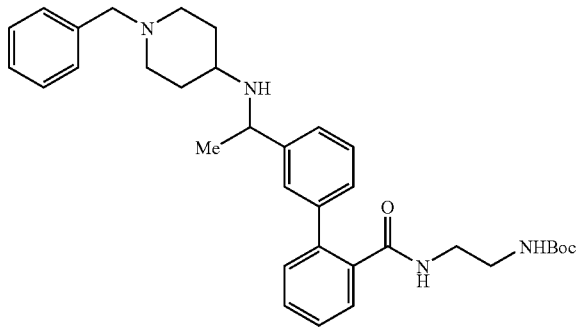

From the compound obtained in Reference Example 4 (2.50 g) was obtained the title compound as a colorless oil (2.59 g) in the same manner as in Reference Example 2.

$^1$H-NMR (CD$_3$OD) δ: 1.29-1.47 (2H, m), 1.36 (3H, d), 1.41 (9H, s), 1.67-1.73 (1H, m), 1.84-1.98 (3H, m), 2.26-2.37 (1H, m), 2.80-2.86 (2H, br), 2.99 (2H, t), 3.18 (2H, t), 3.45 (2H, s), 3.97 (1H, q), 7.21-7.52 (13H, m).

Reference Example 6

N-{2-(tert-butoxycarbonylamino)ethyl}-3'-[1-{N-(2-naphthylacetyl)-N-(piperidin-4-yl)amino)ethyl][1,1'-biphenyl]-2-carboxamide hydrochloride

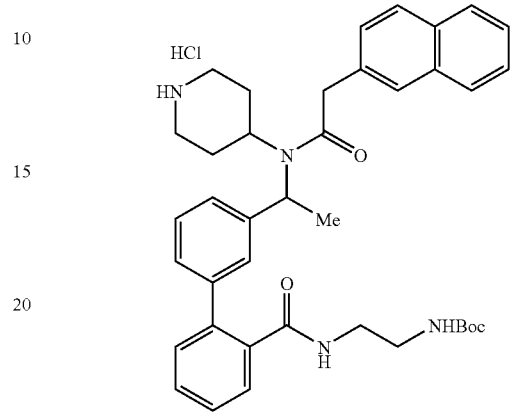

1) 3'-[1-{N-(1-benzylpiperidin-4-yl)-N-(2-naphthylacetyl)amino}ethyl]-N-{2-(tert-butoxycarbonylamino)ethyl}[1,1'-biphenyl]-2-carboxamide To a solution of the compound obtained in Reference Example 3 (1.20 g) in DMF (40 ml) were added N-(2-aminoethyl)carbamic acid tert-butyl ester (310 mg), HOBt (262 mg) and triethylamine (196 mg). WSC (372 mg) was further added to this mixture under ice-cooling, and the mixture was stirred for 18 hours at room temperature. The obtained reaction mixture was diluted with saturated sodium bicarbonate solution (200 ml), and extracted with ethyl acetate (100 ml) twice. The extracted solutions were combined, washed with saturated brine, dried with magnesium sulfate, and the solvent was distilled off under reduced pressure. The residue was purified by silica gel chromatography to give the title compound as a colorless amorphous substance (1.04 g, 74%).

2) N-{2-(tert-butoxycarbonylamino)ethyl}-3'-[1-{N-(2-naphthylacetyl)-N-(piperidin-4-yl)amino}ethyl][1,1'-biphenyl]-2-carboxamide hydrochloride To a solution of the compound obtained in 1) (800 mg) in THF (40 ml) was added α-chloroethyl chloroformic acid (240 μl) under ice-cooling, and the mixture was stirred at room temperature for 6 hours. The reaction mixture was concentrated under reduced pressure, and purified by silica gel chromatography to give a colorless amorphous substance. The obtained compound was dissolved in methanol (40 ml), and heated under reflux for 1 hour. The reaction mixture was cooled to room temperature, and concentrated under reduced pressure. To a solution of the residue in ethanol (3 ml) was added diethyl ether (100 ml), and this solution was purified by reprecipitation, to give the title compound as a white powder (459 mg, 68%).

$^1$H-NMR (CD$_3$OD) δ: 1.08 (1H, br), 1.42 (9H, s), 1.50 (3H, d), 1.70-1.80 (2H, br), 2.62-2.70 (2H, m), 2.99-3.37 (9H, m), 4.15 (2H, s), 5.48 (1H, q), 7.06 (1H, br), 7.13 (2H,br), 7.27 (2H, d), 7.39 (2H, t), 7.47-7.53 (4H, m), 7.79-7.88 (4H, m).

Reference Example 7

N-{2-(tert-butoxycarbonylamino)ethyl}-3'-[1-{N-(4-chlorophenylacetyl)-N-(piperidin-4-yl)amino}ethyl][1,1'-biphenyl]-2-carboxamide hydrochloride

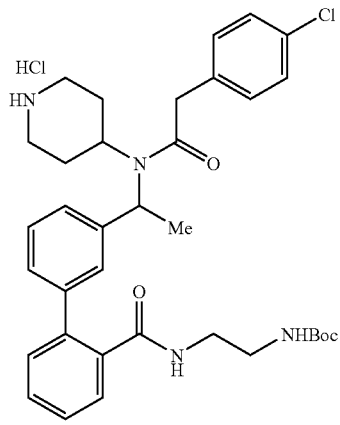

From the compound obtained in Reference Example 5 (4.05 g) was obtained 1.07 g of 3'-[1-{N-(1-benzylpiperidin-4-yl)-N-(4-chlorophenylacetyl)amino}ethyl]-N-(2-(tert-butoxycarbonyl amino)ethyl}[1,1'-biphenyl]-2-carboxamide as a colorless amorphous substance in the same manner as in 1) of Reference Example 3. Furthermore, from this colorless amorphous substance (800 mg) was obtained the title compound as a white powder (335 mg) in the same manner as in 2) of Reference Example 6.

$^1$H-NMR (CD$_3$OD) δ: 1.08 (1H, d) 1.43 (9H, s) 1.55 (3H, d) 1.70-1.80 (1H, br), 2.65 (2H, br) 2.89-3.37 (9H, m), 3.97 (2H, s), 5.35 (1H, q), 7.20-7.56 (12H, m).

Reference Example 8

2-bromobenzyl-carbamic acid tert-butyl ester

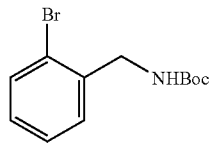

To a solution of 2-bromobenzylamine hydrochloride (5.00 g) and di-tert-butoxycarbonyl (5.39 g) in ethyl acetate (30 ml) was added saturated sodium bicarbonate solution (30 ml), and stirred at room temperature for 16 hours. The obtained reaction mixture was diluted with water, and extracted with ethyl acetate. The organic layer was washed with saturated brine, dried with magnesium sulfate, and the solvent was distilled off under reduced pressure. The residue was purified by silica gel chromatography to give the title compound as a colorless liquid (6.48 g, 95%).

$^1$H-NMR (CDCl$_3$) δ: 1.45 (9H, s), 4.38 (2H, d), 4.95-5.05 (1H, br), 7.13 (1H, t), 7.29 (1H, t), 7.38 (1H, d), 7.53 (1H, d)

Reference Example 9

2-(3-acetylphenyl)benzyl-carbamic acid tert-butyl ester

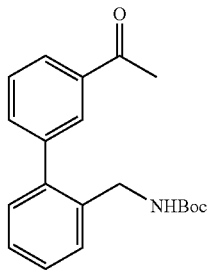

From the compound obtained in Reference Example 8 (6.0 g) was obtained the title compound as a pale brown oil (4.26 g) in the same manner as in Reference Example 1.

$^1$H-NMR (CDCl$_3$) δ: 1.43 (9H, s), 2.63 (3H, s), 4.14 (2H, d), 4.6-4.8 (1H, br), 7.23-7.47 (4H, m), 7.52 (2H, d), 7.94 (1H, s), 7.96 (1H, t).

Reference Example 10

2-[3-[1-{N-(1-benzylpiperidin-4-yl)aminoethyl}phenyl]]benzyl-carbamic acid tert-butyl ester

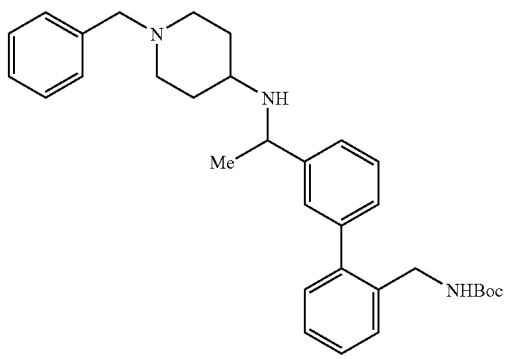

From the compound obtained in Reference Example 9 (2.0 g) as obtained the title compound as a colorless amorphous solid (2.0 g) in the same manner as in Reference Example 2.

$^1$H-NMR (CDCl$_3$) δ: 1.21 (3H, d), 1.41 (9H, m), 1.68 (2H, d), 1.88-1.94 (4H, m), 2.31-2.38 (1H, m), 2.78 (2H, t), 3.43 (2H, s), 3.97 (1H, q), 4.25 (2H, d), 4.91 (1H, t), 7.14-7.44 (13H, m).

Reference Example 11

N-(2-bromophenyl)-3-(tert-butoxycarbonylamino) propanecarboxamide

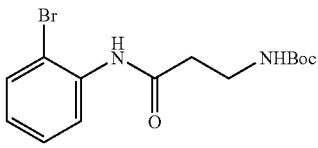

To a solution of 3-(tert-butoxycarbonylamino)propionic acid (4.3 g) and pyridine (3.6 ml) in THF (40 ml) were added oxalyl chloride (3.0 ml) and DMF (3 drops) under ice-cooling, and the mixture was stirred at room temperature for 1 hour. To the obtained reaction solution were added o-bromoaniline (2.6 g), triethylamine (6.3 ml) and a solution of 4-dimethylaminopyridine (0.37 g) in acetonitrile (50 ml) under ice-cooling, and the mixture was stirred at room temperature for 20 hours. The reaction mixture was diluted with saturated sodium bicarbonate solution (200 ml) and extracted with ethyl acetate (200 ml) twice. The extracted solutions were combined, washed with saturated brine, dried with magnesium sulfate, and the solvent was distilled off under reduced pressure. The residue was purified by silica gel chromatography to give the title compound as white crystals (0.91 g, 18%).

$^1$H-NMR (CD$_3$OD) δ: 1.43 (9H, s), 2.62 (2H, t), 3.41 (2H, t), 7.08-7.15 (1H, m), 7.31-7.37 (1H, m), 7.60-7.69 (2H, m).

Reference Example 12

N-{3'-acetyl-1,1'-biphenyl-2-yl}-3-(tert-butoxycarbonylamino)propanecarboxamide

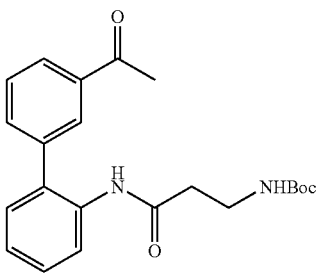

From the compound obtained in Reference Example 11 (0.8 g) was obtained the title compound as a colorless oil (0.77 g, 87%) in the same manner as in Reference Example 1.

$^1$H-NMR (CD$_3$OD) δ: 1.42 (9H, s), 2.37 (2H, t), 2.63 (3H, s), 3.23 (2H, t), 7.35-7.65 (6H, m), 7.96-8.00 (2H, m).

Reference Example 13

N-(3'-(1-(1-benzylpiperidin-4-yl)amino)ethyl-1,1'-biphenyl-2-yl)-3-(tert-butoxycarbonylamino) propanecarboxamide

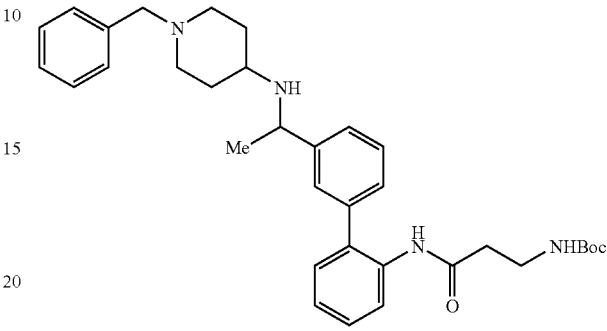

From the compound obtained in Reference Example 12 (0.7 g) was obtained the title compound as a colorless oil (0.65 g, 64%) in the same manner as in Reference Example 2.

$^1$H-NMR (CD$_3$OD) δ: 1.37 (3H, d), 1.42 (9H, s), 1.65-1.74 (2H, br), 1.82-2.00 (4H, br), 2.37 (2H, t), 2.84 (2H, br), 3.26 (2H, t), 3.46 (2H, s), 4.04 (1H, m), 7.23-7.53 (13H, m).

Example 1

N-(2-aminoethyl)-3'-[1-{N-(1-benzylpiperidin-4-yl)-N-(2-naphthylacetyl)amino}ethyl][1,1'-biphenyl)-2-carboxamide dihydrochloride

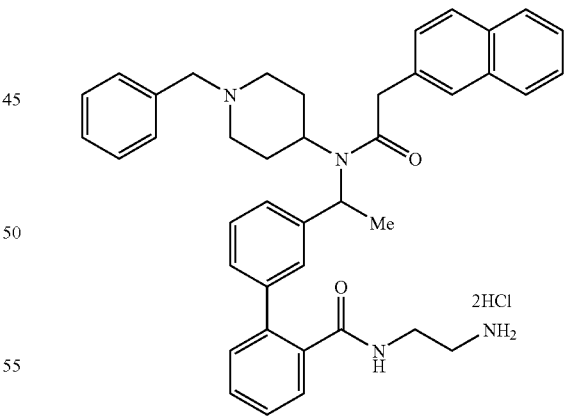

To a solution of the compound obtained in Reference Example 5 (70 mg) and triethylamine (38 mg) in THF (5 ml) was added a solution of 2-naphthylacetylchloride (77 mg) in THF (1 ml) under ice-cooling, and the mixture was stirred at room temperature for 4 hours. The reaction mixture was diluted with saturated sodium bicarbonate solution (100 ml) and extracted with ethyl acetate (50 ml) twice. The extracted solutions were combined, washed with saturated brine, dried with magnesium sulfate, and the solvent was distilled off under reduced pressure. The residue was purified by silica gel chromatography to give a colorless amorphous substance (40 mg). To a solution of this amorphous substance (30 mg) in ethyl acetate (3 ml) was added a solution of 4 N hydrochloric acid in ethyl acetate (3 ml), and the mixture was stirred for 2 hours at room temperature. The reaction mixture was concentrated under reduced pressure, and crystallized from methanol-diethyl ether to give the title compound as a white powder (22 mg).

$^1$H-NMR (CD$_3$OD) δ: 1.17 (1H, br), 1.52 (3H, d), 1.80 (1H, d), 2.70-2.76 (4H, m), 2.98 (2H, t), 3.05-3.30 (3H, m), 3.41 (2H, t), 4.13(2H, s), 4.24(2H, br), 5.46 (1H, q), 7.10(1H, br), 7.13(1H, s), 7.40-7.57(14H, m), 7.78-7.86(4H, m).

FAB-MS m/e: 625.4 (MH$^+$).

Elemental Analysis (Molecular formula C$_{41}$H$_{44}$N$_4$O$_2$.2HCl.1.4H$_2$O):

Calcd. C, 68.12; H, 6.80; N, 7.75; Cl, 9.81.
Found C,: 67.93; H, 6.87; N, 7.71; Cl, 9.68.

Example 2

N-(2-aminoethyl)-3'-[1-{N-(1-benzylpiperidin-4-yl)-N-(4-bromophenylacetyl)amino}ethyl][1,1'-biphenyl]-2-carboxamide dihydrochloride

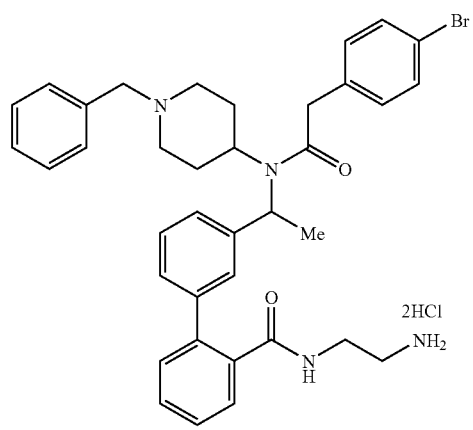

From the compound obtained in Reference Example 5 (150 mg) was obtained the title compound as a white powder (32 mg) in the same manner as in Example 1.

FAB-MS m/e: 653.1 (MH$^+$).

Elemental Analysis (Molecular formula C$_{37}$H$_{41}$N$_4$O$_2$Br.2HCl.2.8H$_2$O):

Calcd. C, 57.19; H, 6.30; N, 7.21.
Found C, 56.91; H, 6.08; N, 7.05.

Example 3

N-(2-aminoethyl)-3'-[1-{N-(1-benzylpiperidin-4-yl)-N-(4-chlorophenylacetyl)amino}ethyl][1,1'-biphenyl]-2-carboxamide dihydrochloride

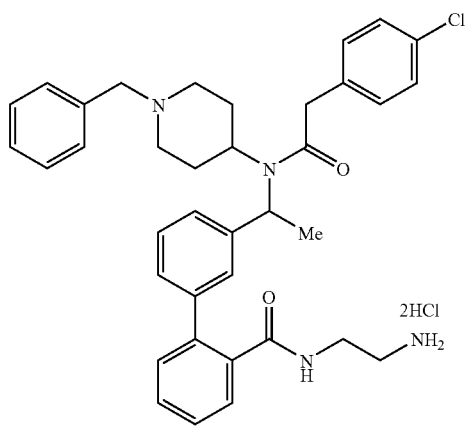

From the compound obtained in Reference Example 5 (150 mg) was obtained the title compound as a white powder (10 mg) in the same manner as in Example 1.

FAB-MS m/e: 609.3 (MH$^+$).

Elemental Analysis (Molecular formula C$_{37}$H$_{41}$N$_4$O$_2$Cl.2HCl.H$_2$O):

Calcd. C, 63.47; H, 6.48; N, 8.00; Cl, 15.19.
Found C, 63.60; H, 6.69; N, 7.82; Cl, 14.91.

Example 4

N-(2-aminoethyl)-3'-[1-(N-(1-benzylpiperidin-4-yl)-N-(3-chlorophenylacetyl)amino}ethyl][1,1'-biphenyl]-2-carboxamide dihydrochloride

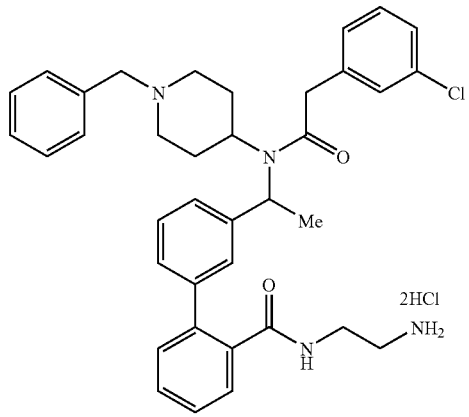

From the compound obtained in Reference Example 5 (150 mg) was obtained the title compound as a white powder (64 mg) in the same manner as in Example 1.

FAB-MS m/e: 609.3 (MH$^+$).

Elemental Analysis (Molecular formula C$_{37}$H$_{41}$N$_4$O$_2$Cl.2HCl.1.3H$_2$O):

Calcd. C, 62.99; H, 6.51; N, 7.94; Cl, 15.07.
Found C, 62.83; H, 6.46; N, 7.71; Cl, 14.97.

Example 5

N-(2-aminoethyl)-3'-[1-{N-(1-benzylpiperidin-4-yl)-N-(2-chlorophenylacetyl)amino}ethyl][1,1'-biphenyl]-2-carboxamide dihydrochloride

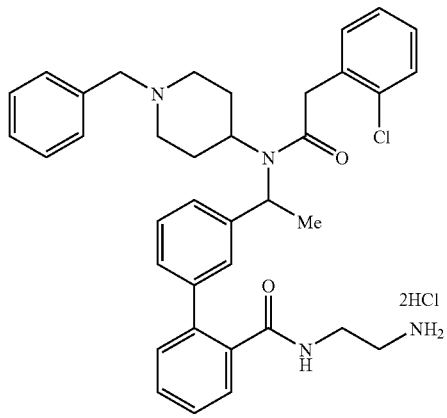

From the compound obtained in Reference Example 5 (150 mg) was obtained the title compound as a white powder (37 mg) in the same manner as in Example 1.

FAB-MS m/e: 609.2 (MH+).

Elemental Analysis (Molecular formula $C_{37}H_{41}N_4O_2Cl$, 2HCl.1.8H$_2$O):

Calcd. C, 62.19; H, 6.57; N, 7.84; Cl, 14.88.
Found C, 61.96; H, 6.58; N, 7.78; Cl, 14.78.

Example 6

N-(2-aminoethyl)-3'-[1-{N-(1-benzylpiperidin-4-yl)-N-(4-methoxyphenylacetyl)amino}ethyl][1,1'-biphenyl]-2-carboxamide dihydrochloride

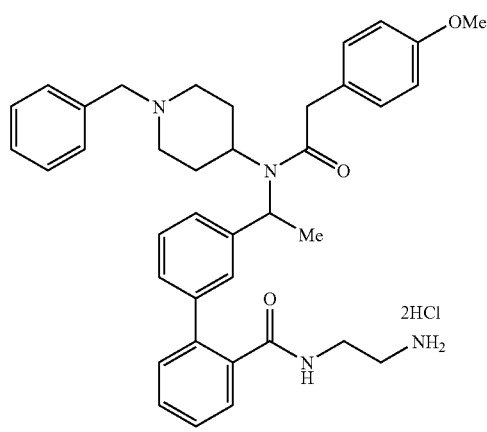

From the compound obtained in Reference Example 5 (150 mg) was obtained the title compound as a white powder (98 mg) in the same manner as in Example 1.

FAB-MS m/e: 605.3 (MH+).

Elemental Analysis (Molecular formula $C_{38}H_{44}N_4O_3$.2HCl.1.3H$_2$O):

Calcd. C, 65.08; H, 6.99; N, 7.99.
Found C, 65.00; H, 7.25; N, 7.90.

Example 7

N-(2-aminoethyl)-3'-[1-{N-(1-benzylpiperidin-4-yl)-N-(4-pyridylacetyl)amino}ethyl][1,1'-biphenyl]-2-carboxamide trihydrochloride

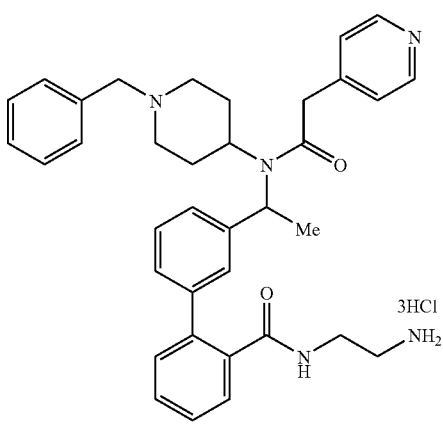

To a solution of the compound obtained in Reference Example 5 (150 mg) in DMF (3 ml) were added 4-pyridyl acetic acid (94 mg), HOBt (73 mg) and N-methyl morpholine (119 µl). To this mixture, WSC (103 mg) was added under ice-cooling, and the mixture was stirred for 18 hours at room temperature. The obtained reaction mixture was diluted with saturated sodium bicarbonate solution (100 ml) and extracted with ethyl acetate (100 ml) twice. The extracted solutions were combined, washed with saturated brine, dried with magnesium sulfate, and the solvent was distilled off under reduced pressure. The residue was purified by silica gel chromatography to give a colorless amorphous substance (140 mg). To a solution of this amorphous substance (140 mg) in ethyl acetate (1 ml) was added a solution of 4 N hydrochloric acid in ethyl acetate (3 ml), and the mixture was stirred for 2 hours at room temperature. The reaction mixture was concentrated under reduced pressure, and reprecipitated from methanol-diethyl ether to give the title compound as a white powder (130 mg).

FAB-MS m/e: 576.2 (MH+).

Elemental Analysis (Molecular formula $C_{36}H_{41}N_5O_2$.3HCl.1.5H$_2$O.0.5MeOH):

Calcd. C: 60.21; H: 6.78; N: 9.62.
Found C: 60.25; H: 6.99; N: 9.59.

Example 8

N-(2-aminoethyl)-3'-[1-{N-(1-benzylpiperidin-4-yl)-N-(4-fluorophenylacetyl)amino}ethyl][1,1'-biphenyl]-2-carboxamide dihydrochloride

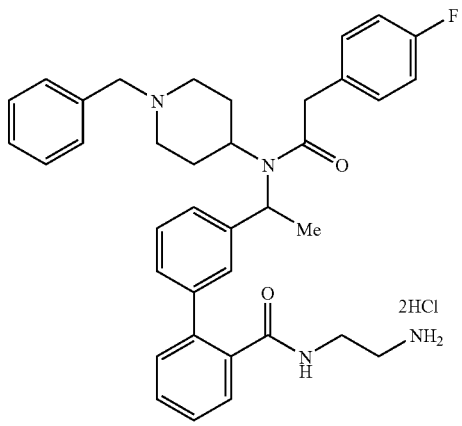

From the compound obtained in Reference Example 5 (150 mg) was obtained the title compound as a pale yellow powder (54 mg) in the same manner as in Example 1.
FAB-MS m/e: 593.2 (MH$^+$).
Elemental Analysis (Molecular formula C$_{37}$H$_{41}$N$_4$O$_2$F.2HCl.0.5H$_2$O.1.4MeOH):
Calcd. C, 64.10; H, 6.95; N, 7.79.
Found C, 64.25; H, 6.77; N, 7.55.

Example 9

N-(2-aminoethyl)-3'-[1-{N-(1-benzylpiperidin-4-yl)-N-(3,4-dichlorophenylacetyl)amino}ethyl][1,1'-biphenyl]-2-carboxamide dihydrochloride

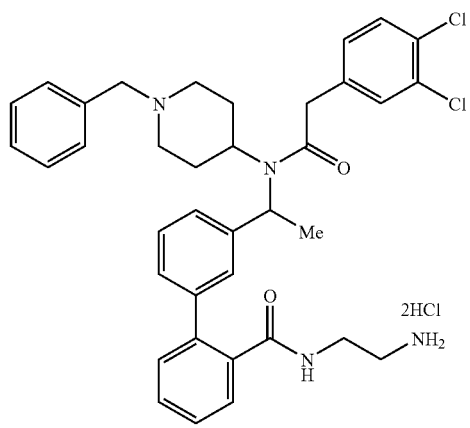

From the compound obtained in Reference Example 5 (150 mg) was obtained the title compound as a white powder (135 mg) in the same manner as in Example 1.
FAB-MS m/e: 643.1 (MH$^+$).
Elemental Analysis (Molecular formula C$_{37}$H$_{40}$N$_4$O$_2$Cl$_2$.2HCl.H$_2$O.1.5MeOH):
Calcd. C, 59.08; H, 6.44; N, 7.16.
Found C, 59.16; H, 6.26; N, 6.99.

Example 10

N-(2-aminoethyl)-3'-[1-{N-(1-benzylpiperidin-4-yl)-N-(1-naphthylacetyl)amino}ethyl][1,1'-biphenyl]-2-carboxamide dihydrochloride

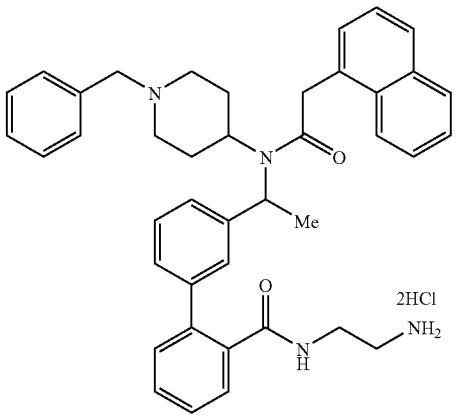

From the compound obtained in Reference Example 5 (150 mg) was obtained the title compound as a pale yellow powder (67 mg) in the same manner as in Example 1.
FAB-MS m/e: 625.3 (MH$^+$).
Elemental Analysis (Molecular formula C$_{41}$H$_{44}$N$_4$O$_2$.2HCl.0.6H$_2$O.0.2MeOH):
Calcd. C, 66.85; H, 7.20; N, 7.25.
Found C, 66.87; H, 7.22; N, 7.00.

Example 11

N-(2-aminoethyl)-3'-[1-{N-(1-benzylpiperidin-4-yl)-N-phenylacetylamino}ethyl][1,1'-biphenyl]-2-carboxamide dihydrochloride

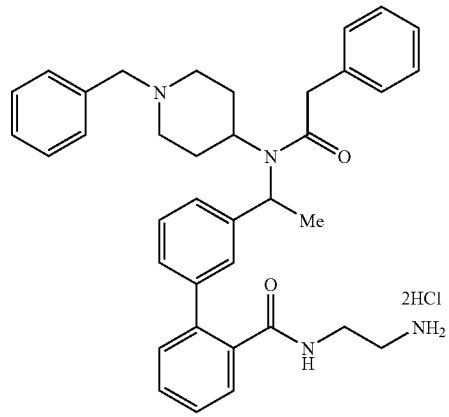

From the compound obtained in Reference Example 5 (150 mg) was obtained the title compound as a white powder (73 mg) in the same manner as in Example 1.
FAB-MS m/e: 575.2 (MH$^+$).
Elemental Analysis (Molecular formula C$_{37}$H$_{42}$N$_4$O$_2$.2HCl.1.5H$_2$O):
Calcd. C, 65.87; H, 7.02; N, 8.30.
Found C, 65.74; H, 7.23; N, 8.15.

Example 12

N-(2-aminoethyl)-3'-[1-{N-benzoyl-N-(1-benzylpiperidin-4-yl)amino}ethyl][1,1'-biphenyl]-2-carboxamide dihydrochloride

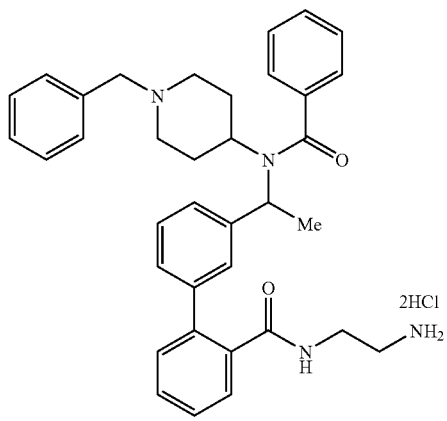

From the compound obtained in Reference Example 5 (150 mg) was obtained the title compound as a white powder (79 mg) in the same manner as in Example 1.
FAB-MS m/e: 561.3 (MH$^+$).
Elemental Analysis (Molecular formula $C_{36}H_{40}N_4O_2.2HCl.1.2H_2O.0.5MeOH$):
Calcd. C, 65.31; H, 6.97; N, 8.35.
Found C, 65.44; H, 7.12; N, 8.38.

Example 13

N-(2-aminoethyl)-3'-[1-{N-(1-benzylpiperidin-4-yl)-N-phenoxyacetylamino}ethyl][1,1'-biphenyl]-2-carboxamide dihydrochloride

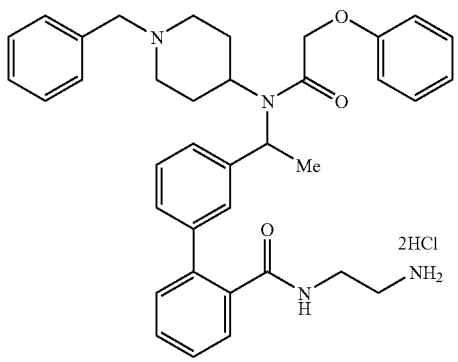

From the compound obtained in Reference Example 5 (150 mg) was obtained the title compound as a white powder (107 mg) in the same manner as in Example 1.
FAB-MS m/e: 591.2 (MH$^+$).
Elemental Analysis (Molecular formula $C_{37}H_{42}N_4O_3.2HCl.1.1H_2O$):
Calcd. C, 65.02; H, 6.81; N, 8.20.
Found C, 65.08; H, 6.91; N, 8.26.

Example 14

N-(2-aminoethyl)-3'-[1-{N-(1-benzylpiperidin-4-yl)-N-cyclohexylacetylamino}ethyl][1,1'-biphenyl]-2-carboxamide dihydrochloride

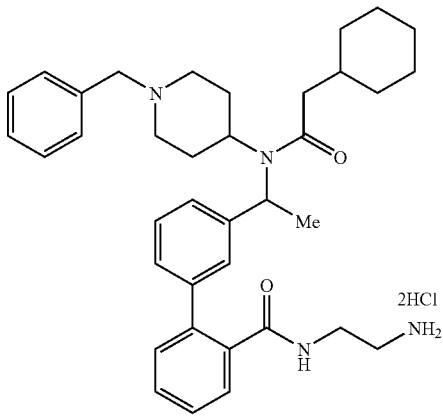

From the compound obtained in Reference Example 5 (150 mg) was obtained the title compound as a white powder (97 mg) in the same manner as in Example 1.
FAB-MS m/e: 581.3 (MH$^+$).
Elemental Analysis (Molecular formula $C_{37}H_{48}N_4O_2.2HCl.1.2H_2O$):
Calcd. C, 65.80; H, 7.82; N, 8.30.
Found C, 65.78; H, 7.95; N, 8.39.

Example 15

N-(2-aminoethyl)-3'-[1-(N-(1-benzylpiperidin-4-yl)-N-((4-methylcyclohexan-1-yl)acetyl)amino}ethyl][1,1'-biphenyl]-2-carboxamide dihydrochloride

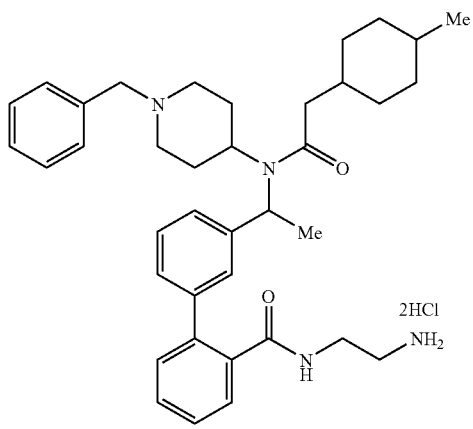

From the compound obtained in Reference Example 5 (150 mg) was obtained the title compound as a white powder (111 mg) in the same manner as in Example 1.
FAB-MS m/e: 595.2 (MH$^+$).
Elemental Analysis (Molecular formula $C_{38}H_{50}N_4O_2.2HCl.1.4H_2O.0.3MeOH$):
Calcd. C, 65.47; H, 8.03; N, 7.97.
Found C, 65.40; H, 8.27; N, 7.89.

Example 16

N-(2-aminoethyl)-3'-[1-(N-(2-naphthylacetyl)-N-(piperidin-4-yl)amino}ethyl][1,1'-biphenyl]-2-carboxamide dihydrochloride

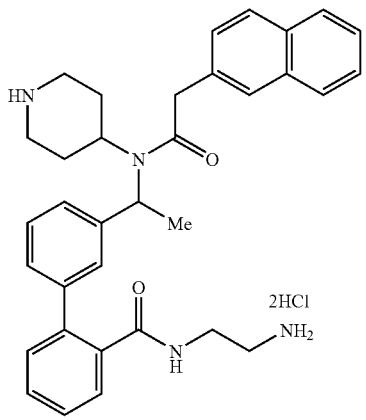

The compound obtained in Reference Example 6 (60 mg) was dissolved in a mixed solution of ethanol (0.3 ml) and ethyl acetate (2 ml), to this solution was added a solution of 4 N hydrochloric acid in ethyl acetate (2 ml), and the mixture was stirred at room temperature for 3 hours. The reaction mixture was concentrated under reduced pressure, and reprecipitated from ethanol-diethyl ether to give the title compound as a white powder (56 mg).

FAB-MS m/e: 535.2 (MH$^+$).

Elemental Analysis (Molecular formula $C_{34}H_{38}N_4O_2 \cdot 2HCl \cdot 1.7H_2O$):
  Calcd. C, 63.98; H, 6.85; N, 8.78.
  Found C, 63.71; H, 6.95; N, 8.66.

Example 17

N-(2-aminoethyl)-3'-[1-{N-(1-isobutylpiperidin-4-yl)-N-(2-naphthylacetyl)amino}ethyl][1,1'-biphenyl]-2-carboxamide dihydrochloride

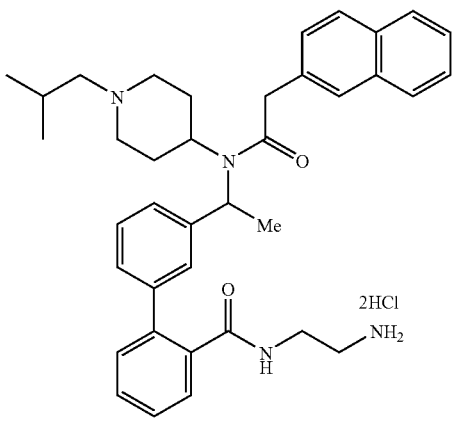

To a solution of the compound obtained in Reference Example 6 (100 mg) in acetonitrile (10 ml), isobutylbromide (162 μl), potassium carbonate (41 mg) and potassium iodide (24 mg) were added, and the mixture was stirred at room temperature for 96 hours. The reaction mixture was diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (70 mg). To a mixed solution of this amorphous substance (70 mg) in ethyl acetate (3 ml) and ethanol (0.5 ml), a solution of 4 N hydrochloric acid in ethyl acetate (3 ml) was added, and the mixture was stirred for 2 hours at room temperature. The reaction mixture was concentrated under reduced pressure, and reprecipitated from ethanol-diethyl ether to give the title compound as a white powder (57 mg).

FAB-MS m/e: 591.4 (MH$^+$).

Elemental Analysis (Molecular formula $C_{38}H_{46}N_4O_2 \cdot 2HCl \cdot 1.4H_2O$):
  Calcd. C, 66.25; H, 7.43; N, 8.13.
  Found C, 65.97; H, 7.42; N, 7.95.

Example 18

N-(2-aminoethyl)-3'-[1-{N-(1-isobutyrylpiperidin-4-yl)-N-(2-naphthylacetyl)amino}ethyl][1,1'-biphenyl]-2-carboxamide hydrochloride

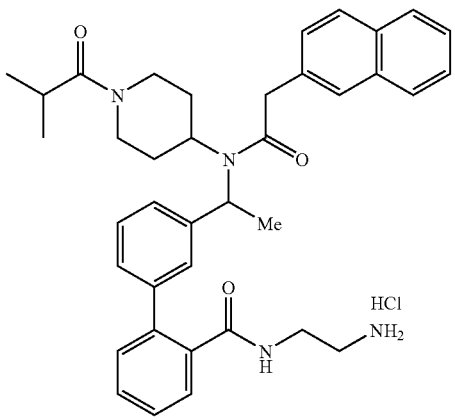

To a solution of the compound obtained in Reference Example 6 (60 mg) and triethylamine (20 mg) in THF (5 ml) was added isobutyryl chloride (11 μl), and the mixture was stirred for 2 hours at room temperature. The reaction mixture was diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (70 mg). To a solution of this amorphous substance (70 mg) in ethyl acetate (3 ml), a solution of 4 N hydrochloric acid in ethyl acetate (3 ml) was added, and the mixture was stirred for 2 hours at room temperature. The reaction mixture was concentrated under reduced pressure, and reprecipitated from ethanol-diethyl ether to give the title compound as a white powder (41 mg).

FAB-MS m/e: 605.4 (MH$^+$).

Elemental Analysis (Molecular formula $C_{38}H_{44}N_4O_3 \cdot HCl \cdot 1.2H_2O$):
  Calcd. C, 68.85; H, 7.21; N, 8.45.
  Found C, 68.68; H, 7.22; N, 8.41.

Example 19

N-(2-aminoethyl)-3'-[1-{N-(1-benzoylpiperidin-4-yl)-N-(2-naphthylacetyl)amino}ethyl][1,1'-biphenyl]-2-carboxamide hydrochloride

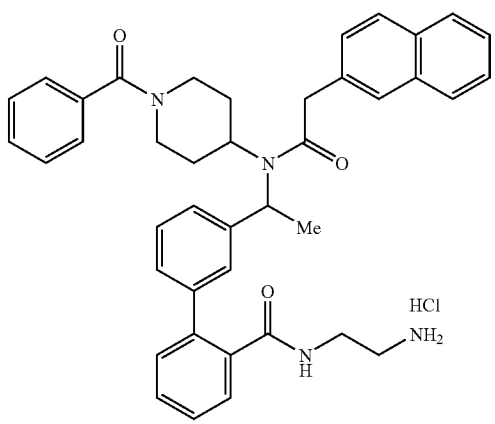

From the compound obtained in Reference Example 6 (60 mg) was obtained the title compound as a white powder (47 mg) in the same manner as in Example 18.

FAB-MS m/e: 639.3 (MH⁺).

Elemental Analysis (Molecular formula $C_{41}H_{42}N_4O_3 \cdot HCl \cdot 1.5H_2O$):

Calcd. C, 70.12; H, 6.60; N, 7.98.
Found C, 69.80; H, 6.64; N, 8.06.

Example 20

N-(2-aminoethyl)-3'-[1-{N-(2-naphthylacetyl)-N-(1-phenylaminocarbonylpiperidin-4-yl)amino}ethyl][1,1'-biphenyl]-2-carboxamide hydrochloride

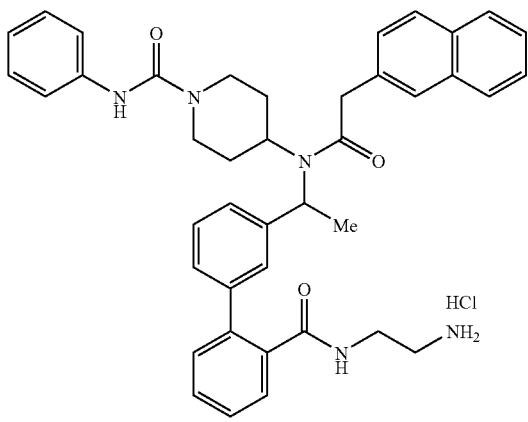

To a solution of the compound obtained in Reference Example 6 (60 mg) in pyridine (2 mg) was added phenyl isocyanate (53 mg), and the mixture was stirred at room temperature for 16 hours. The reaction mixture was concentrated under reduced pressure, and the residue was purified by silica gel chromatography to give a colorless amorphous substance (80 mg). To a solution of this amorphous substance (80 mg) in ethyl acetate (3 ml), a solution of 4 N hydrochloric acid in ethyl acetate (3 ml) was added, and the mixture was stirred for 2 hours at room temperature. The reaction mixture was concentrated under reduced pressure, and reprecipitated from ethanol-diethyl ether to give the title compound as a white powder (57 mg).

FAB-MS m/e: 654.4 (MH⁺).

Elemental Analysis (Molecular formula $C_{41}H_{43}N_5O_3 \cdot HCl \cdot 1.4H_2O$):

Calcd. C, 68.82; H, 6.59; N, 9.79.
Found C, 68.65; H, 6.52; N, 9.82.

Example 21

N-(2-aminoethyl)-3'-[1-{N-(2-naphthylacetyl)-N-(1-(2-pyridylcarbonyl)piperidin-4-yl)amino}ethyl][1,1'-biphenyl]-2-carboxamide dihydrochloride

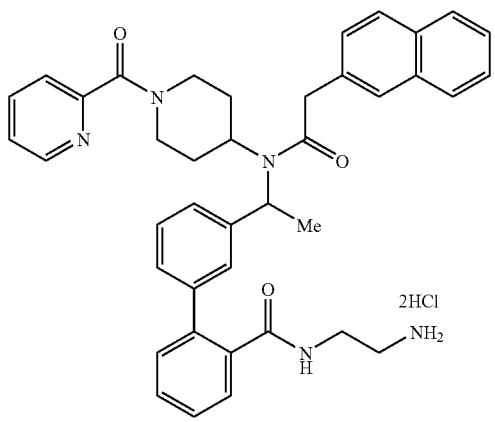

To a solution of the compound obtained in Reference Example 6 (60 mg) in DMF (3 ml) were added 2-pyridine carboxylic acid (12 mg), HOBt (13 mg) and triethylamine (9 mg). To this mixture was added WSC (19 mg) under ice-cooling, and the mixture was stirred at room temperature for 16 hours. The reaction mixture was diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (50 mg) To a solution of this amorphous substance (50 mg) in ethyl acetate (3 ml) was added a solution of 4 N hydrochloric acid in ethyl acetate (3 ml), and the mixture was stirred for 2 hours at room temperature. The reaction mixture was concentrated under reduced pressure, and reprecipitated from ethanol-diethyl ether to give the title compound as a white powder (37 mg).

FAB-MS m/e: 640.3 (MH⁺).

Elemental Analysis (Molecular formula $C_{40}H_{41}N_5O_3 \cdot 1.6HCl \cdot 1.8H_2O$):

Calcd. C, 65.76; H, 6.37; N, 9.59.
Found C, 65.45; H, 6.29; N, 9.54.

Example 22

N-(2-aminoethyl)-3'-[1-{N-(4-chlorophenylacetyl)-N-(1-phenylaminocarbonylpiperidin-4-yl)aminoethyl}][1,1'-biphenyl]-2-carboxamide hydrochloride

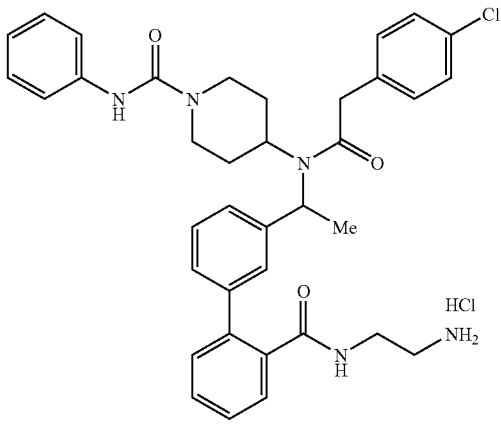

From the compound obtained in Reference Example 7 (60 mg) was obtained the title compound as a white powder (61 mg) in the same manner as in Example 20.

FAB-MS m/e: 638.2 (MH+).

Elemental Analysis (Molecular formula $C_{37}H_{40}N_5O_3Cl.HCl.H_2O$):

Calcd. C, 64.16, H: 6.26; N, 10.11; Cl, 10.24.

Found C, 63.87, H: 6.36; N, 9.94; Cl, 10.12.

Example 23

N-(2-aminoethyl)-3'-[1-{N-(4-chlorophenylacetyl)-N-(1-(2-phenylethyl)piperidin-4-yl)amino}ethyl][1,1'-biphenyl]-2-carboxamide dihydrochloride

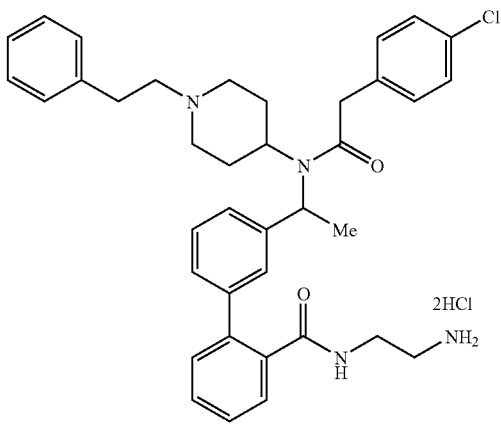

To a solution of the compound obtained in Reference Example 7 (60 mg) in ethanol (3 ml) were added a solution of phenyl acetaldehyde (26 mg) in 50% diethyl phthalate and triethylamine (10 mg). Furthermore, sodium triacetoxyborohydride (23 mg) was added to the mixture, and the mixture was stirred at room temperature for 3 hours. The reaction mixture was diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (40 mg). To a solution of this amorphous substance (40 mg) in ethyl acetate (2 ml) was added a solution of 4 N hydrochloric acid in ethyl acetate (2 ml) and the mixture was stirred for 2 hours at room temperature. The reaction mixture was concentrated under reduced pressure, and reprecipitated from ethanol-diethyl ether to give the title compound as a white powder (21 mg).

FAB-MS m/e: 623.4 (MH+).

Elemental Analysis (Molecular formula $C_{38}H_{43}N_4O_2Cl.2HCl.1.9H_2O$):

Calcd. C, 62.49; H, 6.73; N, 7.67.

Found C, 62.82; H, 6.70; N, 7.67.

Example 24

N-(2-aminoethyl)-3'-[1-{N-(4-chlorophenylacetyl)-N-(1-cyclohexylmethylpiperidin-4-yl)amino}ethyl][1,1'-biphenyl]-2-carboxamide dihydrochloride

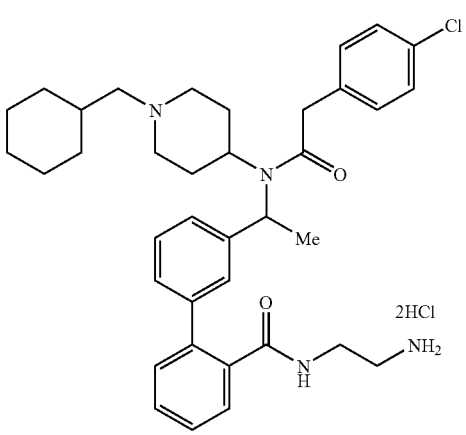

From the compound obtained in Reference Example 7 (60 mg) was obtained the title compound as a white powder (40 mg) in the same manner as in Example 17.

FAB-MS m/e: 615.3 (MH+).

Elemental Analysis (Molecular formula $C_{37}H_{47}N_4O_2Cl.2HCl.2H_2O$):

Calcd. C, 61.52; H, 7.38; N, 7.76; Cl, 14.72.

Found C, 61.73; H, 7.63; N, 7.76; Cl, 14.48.

Example 25

3'-[1-{N-(1-benzylpiperidin-4-yl)-N-(2-naphthylacetyl)amino}ethyl]-N-(2-dimethylaminoethyl)[1,1'-biphenyl]-2-carboxamide dihydrochloride

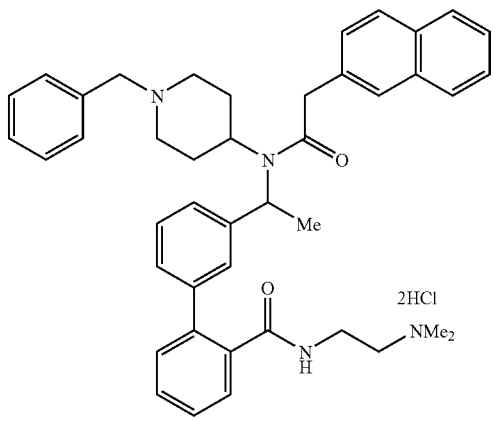

From the compound obtained in Reference Example 3 (0.20 g) was obtained a colorless amorphous substance (0.10 g) in the same manner as in 1) of Reference Example 6. To a solution of this amorphous substance (0.10 g) in ethyl acetate (5 ml) was added a solution of 1 N hydrochloric acid in ether (0.30 ml) under ice-cooling, and the mixture was stirred at the same temperature for 30 minutes. The reaction mixture was concentrated under reduced pressure, and reprecipitated from methanol-diethyl ether to give the title compound as a white powder (87 mg).

FAB-MS m/e: 653.3 (MH$^+$).

Elemental Analysis (Molecular formula $C_{43}H_{48}N_4O_2 \cdot 2HCl \cdot 2H_2O$):

Calcd. C, 67.79; H, 7.14; N, 7.35; Cl, 9.31.
Found C, 68.01; H, 7.44; N, 7.24; Cl, 9.28.

Example 26

3'-[1-{N-(1-benzylpiperidin-4-yl)-N-(2-naphthylacetyl)amino}ethyl]-N-{2-(1-pyrrolidinyl)ethyl)[1,1'-biphenyl]-2-carboxamide dihydrochloride

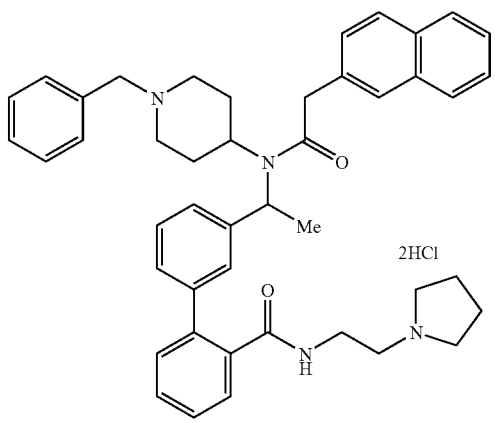

From the compound obtained in Reference Example 3 (0.20 g) was obtained the title compound as a white powder (0.15 g) in the same manner as in Example 25.

FAB-MS m/e: 679.2 (MH$^+$).

Elemental Analysis (Molecular formula $C_{45}H_{50}N_4O_2 \cdot 2HCl \cdot 2H_2O$):

Calcd. C: 68.60; H, 7.16; N, 7.11; Cl, 9.00.
Found C: 68.45; H, 7.27; N, 7.09; Cl, 8.66.

Example 27

N-(3-aminopropyl)-3'-[1-{N-(1-benzylpiperidin-4-yl)-N-(2-naphthylacetyl)amino}ethyl][1,1'-biphenyl]-2-carboxamide dihydrochloride

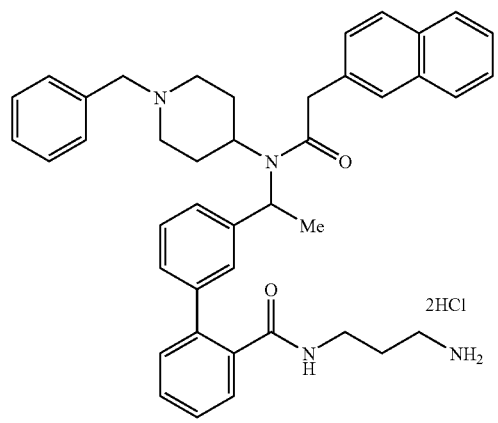

From the compound obtained in Reference Example 3 (0.20 g) was obtained a colorless amorphous substance (0.15 g) in the same manner as in 1) of Reference Example 6. To a solution of this amorphous substance (0.15 g) in ethyl acetate (10 ml) was added a solution of 4 N hydrochloric acid in ethyl acetate (5 ml) under ice-cooling, and the mixture was stirred at room temperature for 2 hours. The reaction mixture was concentrated under reduced pressure, and reprecipitated from methanol-diethyl ether to give the title compound as a white powder (73 mg).

FAB-MS m/e: 639.2 (MH$^+$).

Elemental Analysis (Molecular formula $C_{42}H_{46}N_4O_2 \cdot 2HCl \cdot 1.5H_2O$):

Calcd. C, 68.28; H, 6.96; N, 7.58; Cl, 9.60.
Found C, 67.97; H, 7.08; N, 7.34; Cl, 9.51.

Example 28

N-(4-aminobutyl)-3'-[1-{N-(1-benzylpiperidin-4-yl)-N-(2-naphthylacetyl)amino}ethyl][1,1'-biphenyl]-2-carboxamide dihydrochloride

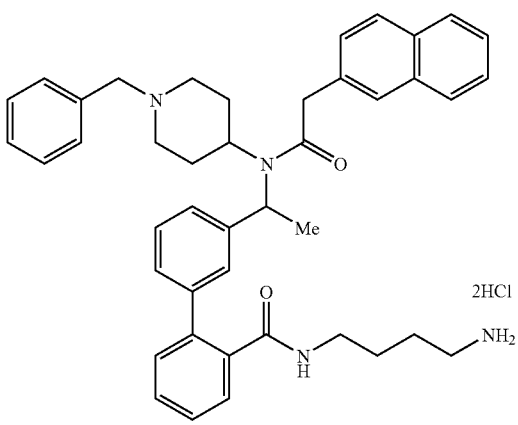

From the compound obtained in Reference Example 3 (0.20 g) was obtained the title compound as a white powder (94 mg) in the same manner as in Example 27.
FAB-MS m/e: 653.2 (MH$^+$).
Elemental Analysis (Molecular formula $C_{43}H_{48}N_4O_2 \cdot 2HCl \cdot 2H_2O$):
Calcd. C, 67.79; H, 7.14; N, 7.35; Cl, 9.31.
Found C, 68.00; H, 7.34; N, 7.39; Cl, 9.23.

Example 29

3'-[1-{N-(1-benzylpiperidin-4-yl)-N-(2-naphthylacetyl)amino}ethyl]-2-{(1-piperazinyl)carbonyl)[1,1'-biphenyl]dihydrochloride

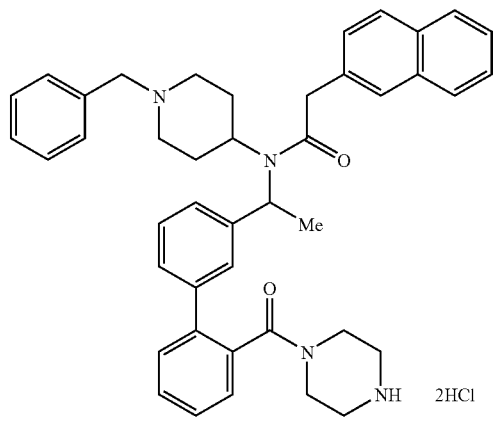

From the compound obtained in Reference Example 3 (0.20 g) was obtained the title compound as a white powder (0.11 g) in the same manner as in Example 27.
FAB-MS m/e: 651.2 (MH$^+$).
Elemental Analysis (Molecular formula $C_{43}H_{46}N_4O_2 \cdot 2HCl \cdot 2H_2O$)
Calcd. C, 67.97; H, 6.90; N, 7.37; Cl, 9.33.
Found C: 67.76; H, 6.94; N, 7.44; Cl, 9.35.

Example 30

3'-[1-{N-(1-benzylpiperidin-4-yl)-N-(2-naphthylacetyl)amino}ethyl][1,1'-biphenyl]-2-carboxylic acid (2-amino) ethyl ester dihydrochloride

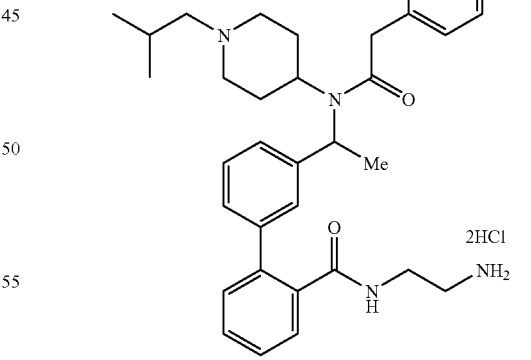

From the compound obtained in Reference Example 3 (0.20 g) was obtained the title compound as a white powder (14 mg) in the same manner as in Example 27.
FAB-MS m/e: 626.3 (MH$^+$).
Elemental Analysis (Molecular formula $C_{41}H_{43}N_3O_3 \cdot 2HCl \cdot 3.5H_2O$):
Calcd. C, 64.64; H, 6.88; N, 5.52.
Found C, 64.74; H, 6.49; N, 5.61.

Example 31

N-(2-aminoethyl)-3'-[1-{N-(4-chlorophenylacetyl)-N-(1-isobutylpiperidin-4-yl)amino}ethyl][1,1'-biphenyl]-2-carboxamide dihydrochloride From the compound obtained in Reference Example 7 (100 mg) was obtained the title compound as a white powder (39 mg) in the same manner as in Example 17.
FAB-MS m/e 575.3 (MH$^+$).
Elemental Analysis (Molecular formula $C_{34}H_{43}N_4O_2Cl \cdot 2.0HCl \cdot 1.3H_2O$):
Calcd. C, 60.81; H, 7.14; N, 8.34.
Found C, 60.63; H, 7.09; N, 8.13.

Example 32

N-(2-aminoethyl)-3'-[1-{N-(4-chlorophenylacetyl)-N-(1-cyclopropylmethylpiperidin-4-yl)amino}ethyl][1,1'-biphenyl]-2-carboxamide dihydrochloride

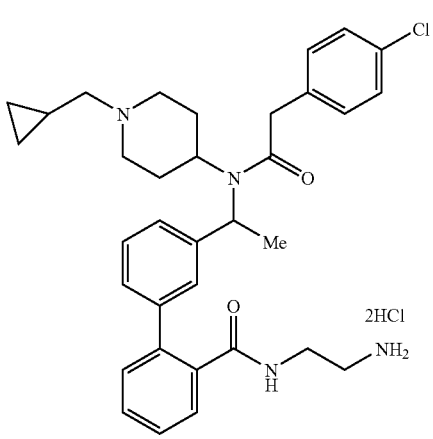

From the compound obtained in Reference Example 7 (100 mg) was obtained the title compound as a white powder (31 mg) in the same manner as in Example 17.
FAB-MS m/e 573.3 (MH⁺).
Elemental Analysis (Molecular formula $C_{34}H_{41}N_4O_2Cl.2.0HCl.1.9H_2O$):
Calcd. C, 60.03; H, 6.93; N, 8.24.
Found C, 60.34; H, 7.16; N, 7.87.

Example 33

N-(2-aminoethyl)-3'-[1-{N-(4-chlorophenylacetyl)-N-(1-isobutyrylpiperidin-4-yl)amino}ethyl][1,1'-biphenyl]-2-carboxamide trifluoroacetate

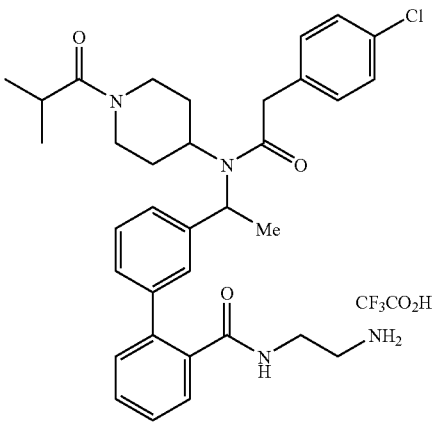

From the compound obtained in Reference Example 7 (100 mg) was synthesized a crude product of the title compound in the same manner as in Example 18, and this was purified by high speed liquid chromatography using acetonitrile-water-trifluoroacetic acid as eluting solution to give the title compound as a white powder (6 mg).
FAB-MS m/e 589.2 (MH⁺).

Example 34

N-(2-aminoethyl)-3'-[1-{N-(4-chlorophenylacetyl)-N-(1-(pyrrol-2-ylcarbonyl)piperidin-4-yl)amino}ethyl][1,1'-biphenyl]-2-carboxamide trifluoroacetate

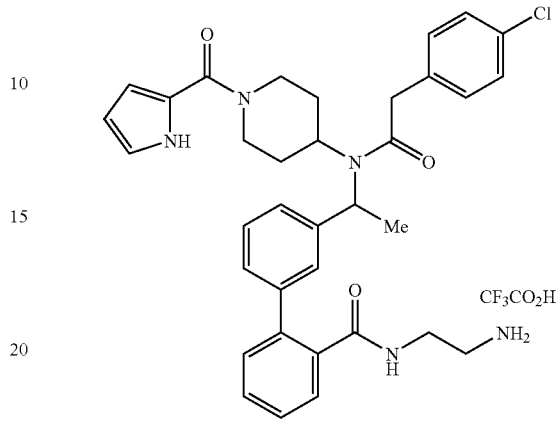

From the compound obtained in Reference Example 7 (100 mg) was synthesized a crude product of the title compound in the same manner as in Example 21, and this was purified by high speed liquid chromatography using acetonitrile-water-trifluoroacetic acid as eluting solution to give the title compound as a white powder (69 mg).
FAB-MS m/e 612.3 (MH⁺).
Elemental Analysis (Molecular formula $C_{35}H_{38}N_5O_3Cl.1.0CF_3CO_2H.0.8H_2O$):
Calcd. C, 60.01; H, 5.53; N, 9.46.
Found C, 59.78; H, 5.60; N, 9.11.

Example 35

N-(2-aminoethyl)-3'-[1-{N-(4-chlorophenylacetyl)-N-(1-(pyrrol-3-ylcarbonyl)piperidin-4-yl)amino}ethyl][1,1'-biphenyl]-2-carboxamide trifluoroacetate

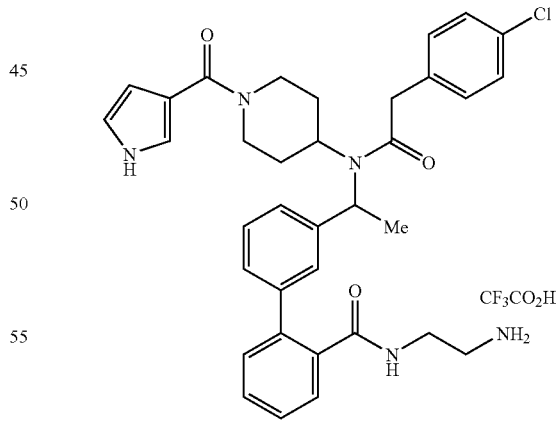

From the compound obtained in Reference Example 7 (100 mg) was obtained the title compound as a white powder (34 mg) in the same manner as in Example 34.
FAB-MS m/e 612.3 (MH⁺).
Elemental Analysis (Molecular formula $C_{35}H_{38}N_5O_3Cl.1.0CF_3CO_2H.0.8H_2O$):
Calcd. C, 60.01; H, 5.53; N, 9.46
Found C, 60.01; H, 5.51; N, 9.29

Example 36

N-(2-aminoethyl)-3'-[1-{N-(4-chlorophenylacetyl)-
N-(1-(3-hydroxybenzoyl)piperidin-4-yl)
amino}ethyl][1,1'-biphenyl]-2-carboxamide trifluoroacetate

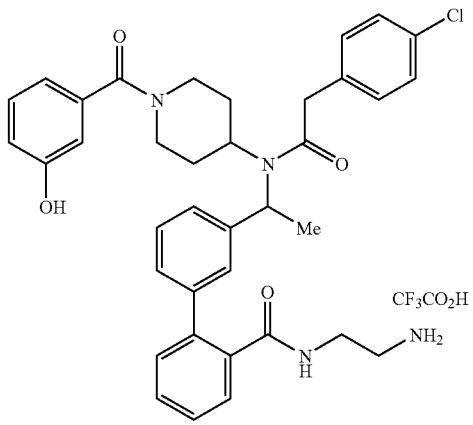

To a solution of the compound obtained in Reference Example 7 (100 mg) in DMF (10 ml) were added 3-acetoxy benzoic acid (30 mg), HOBt (23 mg) and triethylamine (15 mg) under ice-cooling and was further added WSC (32 mg). The reaction mixture was stirred at room temperature for 16 hours, diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (40 mg, 34%). To a solution of this amorphous substance (40 mg) in ethyl acetate (3 ml) and ethanol (1 ml) was added a solution of 4 N hydrochloric acid in ethyl acetate (3 ml), and the mixture was stirred for 2 hours at room temperature. The reaction mixture was concentrated under reduced pressure, and purified by high speed liquid chromatography using acetonitrile-water-trifluoroacetic acid as eluting solution to give the title compound as a white powder (11 mg).

FAB-MS m/e 639.3 (MH+).

Example 37

N-(2-aminoethyl)-3'-[1-{N-(4-chlorophenylacetyl)-
N-(1-(4-hydroxybenzoyl)piperidin-4-yl)
amino}ethyl][1,1'-biphenyl]-2-carboxamide hydrochloride

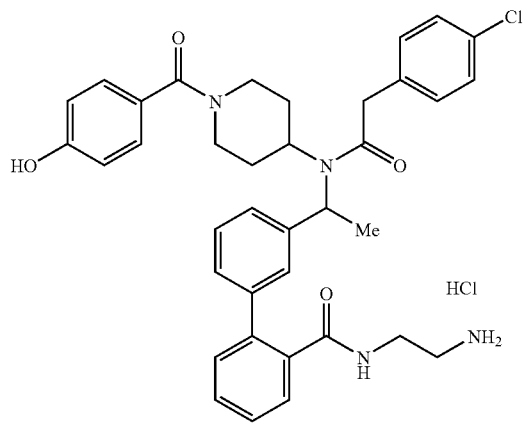

From the compound obtained in Reference Example 7 (100 mg) was obtained the title compound as a white powder (15 mg) in the same manner as in Example 21.

FAB-MS m/e 639.3 (MH+).

Elemental Analysis (Molecular formula $C_{37}H_{39}N_4O_4Cl.1.0HCl.2.0H_2O$):
Calcd. C, 62.45; H, 6.23; N, 7.87
Found C, 62.31; H, 6.28; N, 7.74

Example 38

N-(2-aminoethyl) -3'-[1-{N-(4-chlorophenylacetyl)-
N-(1-cyclohexanecarbonylpiperidin-4-yl)
amino}ethyl][1,1'-biphenyl]-2-carboxamide trifluoroacetate

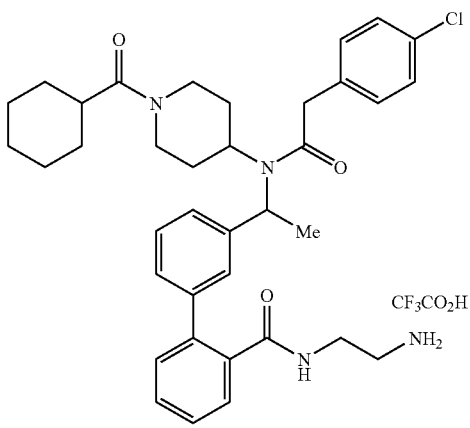

From the compound obtained in Reference Example 7 (100 mg) was obtained the title compound as a white powder (71 mg) in the same manner as in Example 33.

FAB-MS m/e 629.2 (MH+).

Elemental Analysis (Molecular formula $C_{37}H_{45}N_4O_3Cl.1.0CF_3CO_2H.0.6H_2O$):
Calcd. C, 62.12; H, 6.31; N, 7.43.
Found C, 61.85; H, 6.28; N, 7.33.

Example 39

N-(2-aminoethyl)-3'-[1-{N-(4-chlorophenylacetyl)-
N-(1-(1-methylcyclohexanecarbonyl)piperidin-4-yl)
amino}ethyl][1,1'-biphenyl]-2-carboxamide hydrochloride

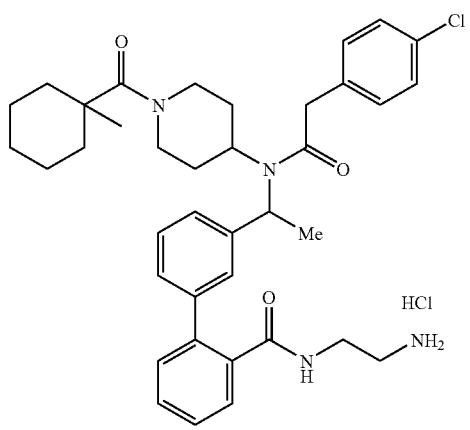

From the compound obtained in Reference Example 7 (100 mg) was obtained the title compound as a white powder (8 mg) in the same manner as in Example 21.
FAB-MS m/e 642.8 (MH+).

Example 40

N-(2-aminoethyl)-3'-[1-{N-(4-chlorophenylacetyl)-N-(1-(indol-2-ylcarbonyl)piperidin-4-yl)amino}ethyl][1,1'-biphenyl]-2-carboxamide trifluoroacetate

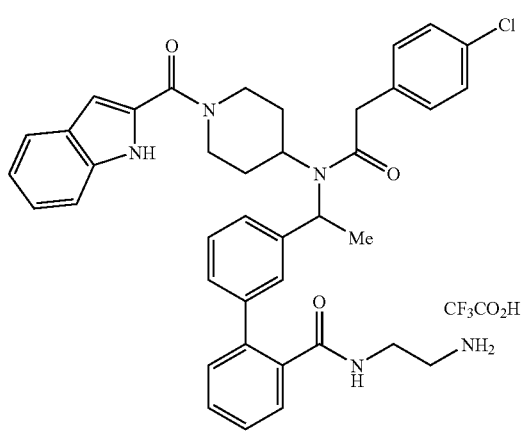

From the compound obtained in Reference Example 7 (100 mg) was obtained the title compound as a white powder (73 mg) in the same manner as in Example 34.
FAB-MS m/e 662.4 (MH+).

Example 41

N-(2-aminoethyl)-3'-[1-(N-(4-chlorophenylacetyl)-N-(1-(2-hydroxybenzoyl)piperidin-4-yl)amino}ethyl]l1,1'-biphenyl]-2-carboxamide trifluoroacetate

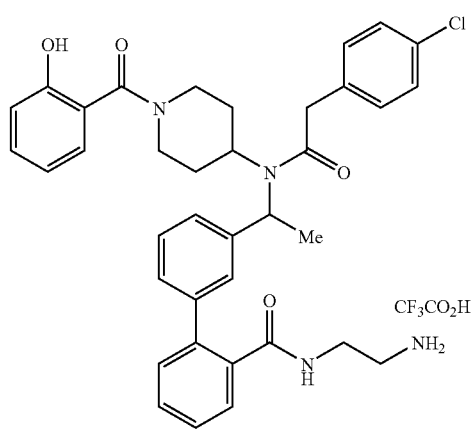

From the compound obtained in Reference Example 7 (100 mg) was obtained the title compound as a white powder (75 mg) in the same manner as in Example 34.
FAB-MS m/e 639.3 (M+).

Example 42

N-(2-aminoethyl)-3'-[1-{N-(1-(benzofuran-2-ylcarbonyl)piperidin-4-yl)-N-(4-chlorophenylacetyl)amino}ethyl][1,1'-biphenyl]-2-carboxamide hydrochloride

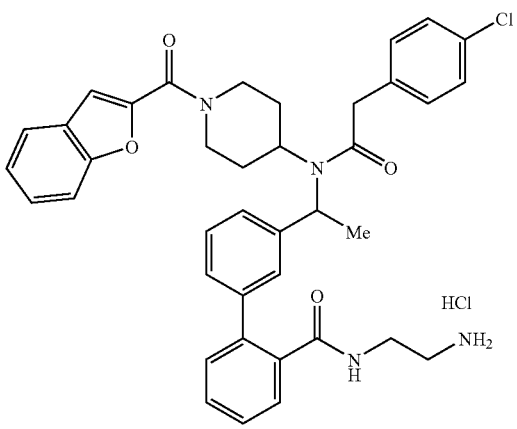

From the compound obtained in Reference Example 7 (100 mg) was obtained the title compound as a white powder (73 mg) in the same manner as in Example 21.
FAB-MS m/e 663.1 (MH+).

Example 43

N-{1-(2'-(aminomethyl)-1,1'-biphenyl-3-yl)ethyl}-N-(1-benzylpiperidin-4-yl)-4-chlorophenylacetamide dihydrochloride

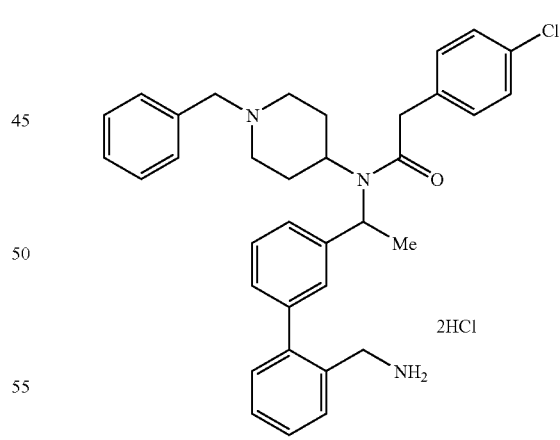

From the compound obtained in Reference Example 10 (1.0 g) was obtained N-{1-(2'-(tert-butoxycarbonylaminomethyl)-1,1'-biphenyl-3-yl)ethyl}-N-(1-benzylpiperidin-4-yl)-4-chlorophenylacetamide as a yellow amorphous solid (0.77 g) in the same manner as in Reference Example 3.

From this compound was obtained the title compound as a white powder (631 mg) in the same manner as in Example 16.
FAB-MS m/e 552.3 (MH+).

Example 44

2-amino-N-[[3'-[1-{N'-(1-benzylpiperidin-4-yl)-N'-(4-chlorophenylacetyl)amino}ethyl]-1,1'-biphenyl-2-yl]methyl]acetamide dihydrochloride

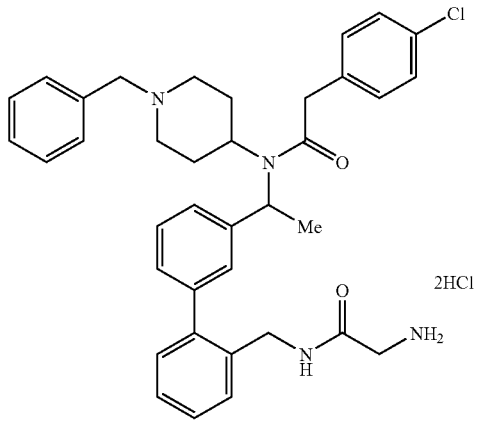

To a solution of the compound obtained in Example 43 (100 mg) in DMF (10 ml) were added Boc-glycine (31 mg), HOBt (24 mg) and triethylamine (32 mg) under ice-cooling, and was further added WSC (34 mg). The reaction mixture was stirred at room temperature for 72 hours, diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (90 mg, 79%). To a solution of this amorphous substance (90 mg) in ethyl acetate (4 ml) was added a solution of 4 N hydrochloric acid in ethyl acetate (4 ml), and the mixture was stirred for 2 hours at room temperature. The reaction mixture was concentrated under reduced pressure, and purified by reprecipitation from ethanol-diethyl ether to give the title compound (71 mg) as a white powder.

FAB-MS m/e 608.8 (MH$^+$).

Example 45

2-[[[3'-[1-{N-(1-benzylpiperidin-4-yl)-N-(4-chlorophenylacetyl)amino}ethyl]-1,1'-biphenyl-2-yl]methyl)amino)acetamide dihydrochloride

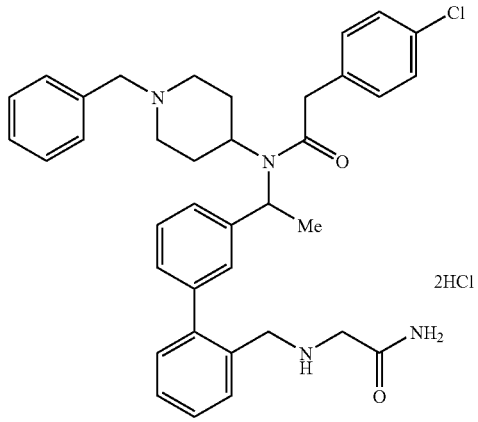

To a solution of the compound obtained in Example 43 (100 mg) in acetonitrile (10 ml) was added 2-chloroacetic acid amide (22 mg) and potassium carbonate (66 mg), and the mixture was stirred at room temperature for 72 hours, and at 60° C. for 6 hours. The reaction mixture was diluted with saturated sodium bicarbonate (100 ml), and extracted with ethyl acetate (50 ml) twice. The extracted solutions were combined, washed with saturated brine, dried with magnesium sulfate, and concentrated under reduced pressure. The residue was purified by silica gel chromatography to give a colorless amorphous substance (60 mg, 62%). To a solution of this amorphous substance (60 mg) in ethyl acetate (10 ml) was added 1 M hydrochloric acid in ether (0.5 ml), and the mixture was concentrated under reduced pressure, and purified by reprecipitation from ethanol-diethyl ether to give the title compound (42 mg) as a white powder.

FAB-MS m/e 609.0 (MH$^+$).

Example 46

N-[3'-[1-(N'-(1-benzylpiperidin-4-yl)-N'-(4-chlorophenylacetyl)amino}ethyl]-1,1'-biphenyl-2-yl]-3-aminopropionamide dihydrochloride

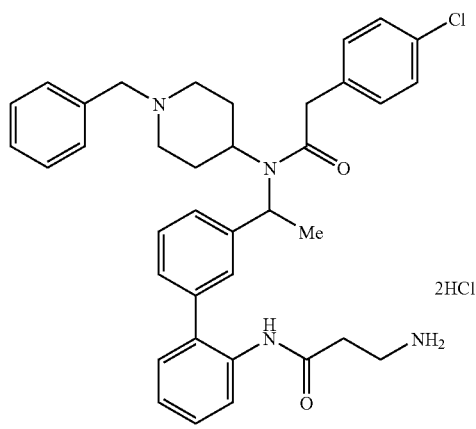

From the compound obtained in Reference Example 13 (88 mg) was obtained N-[3'-[1-{N'-(1-benzylpiperidin-4-yl)-N'-(4-chlorophenylacetyl)amino}ethyl]-1,1'-biphenyl-2-yl]-3-(tert-butoxycarbonylamino)propionamide in the same manner as in Example 1, and from this was obtained the title compound as a white powder (71 mg, 85%) in the same manner as in Example 16.

FAB-MS m/e 609.4 (MH$^+$).

Experimental Example (1) Cloning of Human MC4R

Cloning of MC4R gene was conducted from human brain cDNA by PCR method. Using 0.5 ng of brain cDNA (Clontech, Quick-lone cDNA) as a genetic template, primer sets prepared by referring to MC4R gene base sequence described in Birkenbach M. et al. (J. Virol, 67(4),2209-2220(1993)), i.e., primer-1: 5'-actggaattctcctgccagcatggtg-3' [Sequence No.:1] and primer-2: 5'-catgtcgacatattgcgtgctctgtccc-3' [Sequence No.:2] were added in amounts of 50 pmol, respectively, and the PCR reaction was carried out using TaKaRa LA Taq(Takara Shuzo)in Gene Amp PCR System 9600 (Applied Biosystems)(Reaction conditions: 35 cycles of 95° C. for 1 minute, 62° C. for 1 minute, and 72° C. for 3 minutes).

(2) Preparation of Expression Plasmid for Human MC4R

After the PCR fragments obtained above were digested by restriction enzymes Eco RI (Takara Shuzo) and Sal I (Takara Shuzo), DNA fragments were collected by agarose gel electrophoresis. The DNA fragments and an expression plasmid for animal cells pMSR a neo (Japanese Unexamined Patent Application Publication No. 2000-281685, WO 00/44756), which was previously digested by Eco RI and Sal I, were mixed and ligated using a DNA Ligation Kit Ver. 2 (Takara Shuzo). Transformation of E. coli JM109 competent cells gave plasmid pMC4R.

(3) Introduction of the Expression Plasmid for Human MC4R into CHO-K1 Cells and Expression thereof CHO-KI cells grown in 150 cm² of a cell culture flask (Corning Costar) using Ham F12 medium (GIBCO BRL) containing 10% fetal bovine serum (GIBCO BRL) were collected by using 0.5 g/L trypsin-0.2 g/L EDTA (GIBCO BRL). The cells were washed with PBS (GIBCO BRL), centrifuged (1000 rpm, 5 minutes), and were suspended in PBS. Then, the DNA was introduced into the cells using Gene Pulser (Bio-Rad) according to the following conditions. Namely, $1 \times 10^7$ cells and 15 µg of human MC4R expression plasmid pMC4R were placed in a 0.4-cm gap cuvette, and the mixture was electropolated under 0.25 kV of electric voltage, and 960 µF of capacitance. Cells were then transferred to Ham F12 medium containing 10% fetal bovine serum. After incubation for 24 hours, cells were collected, centrifuged, and suspended in Ham F12 medium containing 10% fetal bovine serum and Geneticin (GIBCO BRL) at a concentration of 500 µg/ml. Cells were diluted to a concentration of 104 cells/ml, and inoculated in 96-well plate (Corning Costar) to obtain Geneticin-resistant strains.

The Geneticin-resistant strains were grown in 96-well plates (OPAQUE PLATE 3917, Costar), and MC4R-expressing cells were selected from the resistant strains. Namely, in an assay buffer (20 mM HEPES (Dojindo Laboratories, Inc.), 0.5% BSA, 0.05% NaN$_3$) containing 200 pM [$^{125}$I]-[Nle4,D-Phe7]-α-Melanocyte Stimulating Hormone (Daiichi Pure Chemicals Co., Ltd.), the cells were subjected to binding reaction at room temperature for 60 minutes. After the assay buffer was removed by inspiration, the cells were washed with ice-cooled PBS, and then stirred after adding 100 µl/well of MicroScint-20 (Packard Industry Company, Inc.) to each well. Subsequently, the cells were counted for radioactivity using a Top Count (Packard) to select CHO/MC4R strains, the cells to which [$^{125}$I]-[Nle4,D-Phe7]-α-Melanocyte Stimulating Hormone bound specifically.

(4) Evaluation of Compounds

The CHO/MC4R strains were inoculated in 96 well microplate at a concentration of $1 \times 10^4$ cells/well, and grown for 72 hours. After removal of the medium by inspiration, to each well were added an assay buffer containing the test compound (10 µM), and then [$^{125}$I]-[Nle4,D-Phe7]-α-Melanocyte Stimulating Hormone (Daiichi Pure Chemicals Co., Ltd.) to a concentration of 100 pM. The mixture was subjected to the reaction at room temperature for 60 minutes. After removal of the assay buffer by inspiration, each well was washed with cooled PBS twice. Then, 100 µl MicroScint 20 (Packerd) was added to each well, and the radioactivity of each well was measured by Top Count (Packard).

According to the method above, binding inhibitory ratios of the test compounds were measured. The results are shown in Table 1.

TABLE 1

| Compound No. | Binding Inhibitory Ratio |
| --- | --- |
| Example 1 | 96% |
| Example 2 | 97% |
| Example 3 | 97% |
| Example 4 | 92% |
| Example 9 | 100% |

Formulation Example

A drug containing the compound of the present invention as an active ingredient may be prepared, for example, according to the following formulations.

1. Capsule

| | |
| --- | --- |
| (1) The compound obtained in Example 1 | 40 mg |
| (2) Lactose | 70 mg |
| (3) Microcrystalline cellulose | 9 mg |
| (4) Magnesium stearate | 1 mg |
| 1 capsule | 120 mg |

(1), (2), (3) and half of (4) are mixed to be granulated. To this mixture is added the rest of (4), and is used to fill a gelatin capsule.

2. Tablet

| | |
| --- | --- |
| (1) The compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

(1), (2), (3), two thirds of (4) and half of (5) are mixed to be granulated. To this is added the rest of (4) and (5), and is pressed into a tablet.

Industrial Applicability

The compound represented by the formula (I) or (I') according to the present invention has strong activity as melanocortin receptor (MC-R) agonist or antagonist, and so is useful as an agent for preventing or treating melanocortin receptor-based diseases (for example, inflammatory diseases, AIDS, obesity, bulimia, anorexia, and the like) or as an agent for improving affective disorder or sexual dysfunction.

What is claimed is:

1. A compound represented by the formula (I):

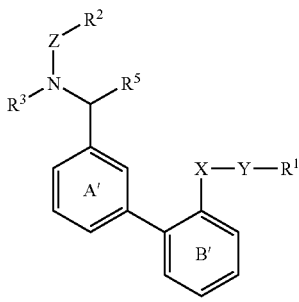

wherein ring A' and ring B' are optionally further substituted benzene rings;

X is —$CONR^4$—, —$SO_2NR^4$—, —$CH_2NR^4$—, —$NR^4CO$—, —$NR^4SO_2$—, —$NR^4$—CO—NH—, —O—, —S—, —SO—, —$SO_2$—, —CO—, —$CO_2$—, —CH=CH— or a bond ($R^4$ is a hydrogen atom, an optionally substituted hydrocarbon group lo or an optionally substituted heterocyclic group);

Y is a saturated divalent group selected from (1) —$(CH_2)_{f1}$— (f1 is an integer of 1 to 12), (2) —$(CH_2)_{g1}$—$Y^1$—$(CH_2)_{g2}$— (g1 and g2 are the same or different and an integer of 0 to 11, provided that the sum of g1 and g2 is 0 to 11, and $Y^1$ is NH, O, S, SO or $SO_2$) and (3) -$(CH_2)_{h1}$—$Y^1$—$(CH_2)_{h2}$—$Y^2$—$(CH_2)_{h3}$— (h1, h2 and h3 are the same or different and an integer of 0 to 10, provided that the sum of h1, h2 and h3 is 0 to 10, and $Y^1$ and $Y^2$ are independently NH, O, S, SO or $SO_2$, provided that when h2 is 0, at least one of $Y^1$ and $Y^2$ is NH) or a divalent group thereof wherein some bonds of the divalent group are converted to unsaturated bonds, each of divalent group may have substituent(s);

Z is —$CONR^6$—, —$CSNR^6$—, —CO— or —$SO_2$— ($R^6$ is a hydrogen atom, an optionally substituted hydrocarbon group or an optionally substituted heterocyclic group);

$R^1$ is an optionally substituted amino group or an optionally substituted heterocyclic group;

$R^2$ is a hydrogen atom, an optionally substituted hydrocarbon group or an optionally substituted heterocyclic group;

$R^3$ is an optionally substituted piperidinyl group; and $R^5$ is methyl;

or a salt thereof.

2. The compound according to claim 1, wherein ring A and ring B are optionally further substituted benzene rings.

3. The compound according to claim 1, wherein $R^1$ is (1) amino optionally substituted with (1') $C_{1-10}$alkyl optionally substituted with carbamoyl or (2') $C_{1-10}$alkylcarbonyl optionally substituted with amino or (2) cyclic amino; $R^2$ is (1) $C_{1-10}$alkyl optionally substituted with pyridyl or $C_{6-14}$aryloxy, (2) $C_{3-8}$cycloalkyl-$C_{1-6}$alkyl optionally substituted with $C_{1-4}$alkyl, (3) $C_{6-14}$aryl, or (4) $C_{6-14}$aryl-alkyl optionally substituted with a substituent selected from (i) halogen, (ii) $C_{1-4}$alkyl optionally halogenated and (iii) $C_{1-4}$alkoxy; $R^3$ is (1) piperidinyl optionally substituted with a substituent selected from (1') phenyl-$C_{1-4}$alkyl, (2') mono-$C_{1-6}$alkyl carbamoyl, (3') $C_{3-8}$cycloalkyl carbamoyl, (4') heterocyclic carbamoyl, (5') mono-$C_{6-14}$aryl carbamoyl, (6') $C_{1-4}$alkyl optionally substituted with $C_{3-8}$cycloalkyl, (7') $C_{2-4}$alkanoyl, (8') $C_{3-8}$cycloalkylcarbonyl, (9') $C_{6-14}$arylcarbonyl optionally substituted with a hydroxy group and (10') aromatic nitrogen-containing or aromatic oxygen-containing heterocyclic carbonyl or (2) pyrrolidinyl optionally substituted with a substituent selected from (1') phenyl-$C_{1-4}$alkyl, (2') mono-$C_{1-6}$alkyl carbamoyl, (3') $C_{3-8}$cycloalkyl carbamoyl, (4') heterocyclic carbamoyl, (5') mono-$C_{6-14}$aryl carbamoyl, (6') $C_{1-4}$alkyl optionally substituted with $C_{3-8}$cycloalkyl, (7') $C_{2-4}$alkanoyl, (8') $C_{3-8}$cycloalkylcarbonyl, (9') $C_{6-14}$arylcarbonyl Optionally substituted with a hydroxy group and (10') aromatic nitrogen-containing or aromatic oxygen-containing heterocyclic carbonyl; $R^5$ is $C_{1-4}$alkyl; X is a bond, —CONH—, —NHCO— or —CO$_2$—; Y is C$_{2-4}$alkylene optionally substituted with C$_{1-6}$alkyl; Z is —CO—, or, X, Y and R$^1$ form piperazylcarbonyl together.

4. The compound according to claim 1, wherein R$^1$ is amino.

5. N-(2-aminoethyl)-3'-[1-{N-(1-benzylpiperidin-4-yl)-N-(2-naphthylacetyl)amino}ethyl][1,1'-biphenyl]-2-carboxamide, N-(2-aminoethyl)-3'-[1-{N-(1-benzylpiperidin-4-yl)-N-(4-chlorophenylacetyl)amino}ethyl][1,1'-biphenyl]-2-carboxamide,N-(2-aminoethyl)-3'-[1-{N-(1-benzylpiperidin-4-yl)-N-(3-chlorophenylacetyl)amino}ethyl][1,1'-biphenyl]-2-carboxamide, N-(2-aminoethyl)-3'-[1-{N-(1-benzylpiperidin-4-yl)-N-(4-bromophenylacetyl)amino}ethyl][1,1'-biphenyl]-2-carboxamide, N-(2-aminoethyl)-3'-[1-{N-(1-benzylpiperidin-4-yl)-N-(3,4-dichlorophenylacetyl)amino}ethyl][1,1'-biphenyl]-2-carboxamide, N-(2-aminoethyl)-3'-[1-{N-(4-chlorophenylacetyl)-N-(1-(2-indolecarbonyl)piperidin-4-yl)amino}ethyl][1,1'-biphenyl]-2-carboxamide, N-(2-aminoethyl)-3'-[1-{N-(1-(2-benzofurancarbonyl)piperidin-4-yl)-N-(4-chlorophenylacetyl)amino}ethyl][1,1'-biphenyl]-2-carboxamide, N-(2-aminoethyl)-3'-[1-{N-(4-chlorophenylacetyl)-N-(1-(4-hydroxybenzoyl)piperidin-4-yl)amino}ethyl][1,1'-biphenyl]-2-carboxamide or salts thereof.

6. A pharmaceutical composition comprising (i) a therapeutically effective amount of at least one of the compound according to claim 1 and a salt thereof and (ii) at least one pharmaceutically acceptable carrier.

* * * * *

UNITED STATES PATENT AND TRADEMARK OFFICE
CERTIFICATE OF CORRECTION

PATENT NO. : 7,507,753 B2 Page 1 of 1
APPLICATION NO. : 10/499903
DATED : March 24, 2009
INVENTOR(S) : Nobuo Cho et al.

It is certified that error appears in the above-identified patent and that said Letters Patent is hereby corrected as shown below:

Title Page In SECTION 73:

Please change the assignee's name to read as follows:

TAKEDA PHARMACEUTICAL COMPANY LIMITED

Please change Claim 1, at col. 87, line 51 to read as follows:

After "group" delete "lo"

Signed and Sealed this

Seventeenth Day of November, 2009

David J. Kappos
*Director of the United States Patent and Trademark Office*

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
actggaattc tcctgccagc atggtg                26

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
catgtcgaca tattgcgtgc tctgtccc              28